US008835117B2

(12) United States Patent
Mitchell et al.

(10) Patent No.: US 8,835,117 B2
(45) Date of Patent: Sep. 16, 2014

(54) NUCLEIC ACIDS FOR DETECTION AND DISCRIMINATION OF GENOTYPES OF *CHLAMYDOPHILA PSITTACI*

(75) Inventors: Stephanie L. Mitchell, Somerville, MA (US); Jonas M. Winchell, Lilburn, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 82 days.

(21) Appl. No.: 13/322,787

(22) PCT Filed: May 28, 2010

(86) PCT No.: PCT/US2010/036742
§ 371 (c)(1), (2), (4) Date: Nov. 28, 2011

(87) PCT Pub. No.: WO2010/138926
PCT Pub. Date: Dec. 2, 2010

(65) Prior Publication Data

US 2012/0082984 A1 Apr. 5, 2012

Related U.S. Application Data

(60) Provisional application No. 61/182,628, filed on May 29, 2009.

(51) Int. Cl.
*C12Q 1/68* (2006.01)
*C07H 21/04* (2006.01)

(52) U.S. Cl.
CPC .................................... *C12Q 1/689* (2013.01)
USPC .... 435/6.12; 435/6.15; 536/24.32; 536/24.33

(58) Field of Classification Search
None
See application file for complete search history.

(56) References Cited

U.S. PATENT DOCUMENTS 6,884,784 B1 * 4/2005 Mitchell et al. ................. 514/31
2006/0008828 A1 1/2006 Vanrompay

OTHER PUBLICATIONS

Nazarenko, I. Methods in Molecular Biology (2006) 335: 95-114.*

Jeffrey et al. Microbiology (2007) 153: 2679-2688.*

Geens et al. Journal of Clinical Microbiology (2005) 43(5): 2456-2461.*

Geens et al., "Development of a *Chlamydophila psittaci* species-specific and genotype-specific real-time PCR," *Vet. Res.*, 36: 787-797, 2005.

Geens et al., "Sequencing of the *Chlamydophila psittaci ompA* Gene Reveals a New Genotype, E/B, and the Need for a Rapid Discriminatory Genotyping Method," *J. Clin. Microbiol.*, 43(5): 2456-2461, 2005.

Heddema, "Genotyping of *Chlamydophila psittaci* in Human Samples," *Emerging Infectious Diseases*, 12(12): 1989-1990, 2006.

Menard, "Development of a real-time PCR for the detection of *Chlamydia psittaci*," *J. Med. Microbiol.*, 55(Pt. 4): 471-473, 2006.

Mitchell et al., "Genotyping of *Chlamydophila psittaci* by Real-Time PCR and High-Resolution Melt Analysis," *Journal of Clinical Microbiology*, 47(1): 175-181, 2009.

Sachse et al., "Genotyping of *Chlamydophila psittaci* using a new DNA microarray assay based on sequence analysis of ompA genes," *BMC Microbiology*, 8:63, pp. 1-12, 2008.

* cited by examiner

*Primary Examiner* — Angela M Bertagna
(74) *Attorney, Agent, or Firm* — Klarquist Sparkman, LLP

(57) ABSTRACT

Methods of detecting *Chlamydophila*, including differentiating between species of *Chlamydophila* and/or strains of *Chlamydophila psittaci* are disclosed, for example to detect and genotype a *Chlamydophila psittaci* infection. A sample suspected of containing a nucleic acid of a *Chlamydophila*, is screened for the presence of that nucleic acid. The presence of the *Chlamydophila* nucleic acid indicates the presence of the *Chlamydophila* bacterium. Determining whether a *Chlamydophila* nucleic acid is present in a sample can be accomplished by detecting hybridization between a *Chlamydophila* specific primer, a *Chlamydophila psittaci* specific primer, and/or a *Chlamydophila psittaci* genotype-specific primer and the *Chlamydophila* nucleic acid containing sample. Thus, primers for the detection, species-specific and/or genotype-specific identification of *Chlamydophila psittaci* are disclosed. Kits that contain the disclosed primers also are disclosed.

9 Claims, 10 Drawing Sheets

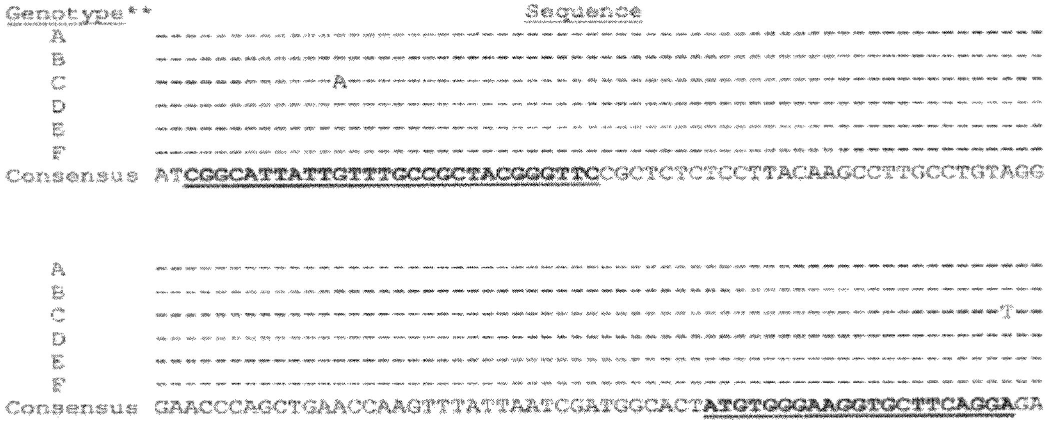

FIG. 4A

```
Genotype**                                                Sequence
    A        ------------------------------------------------------
    B        ------------------------------------------------------
    C        ----------------A-------------------------------------
    D        ------------------------------------------------------
    E        ------------------------------------------------------
    F        ------------------------------------------------------
Consensus    ATCGGCATTATTGTTTGCCGCTACGGGTTCCGCTCTCTCCTTACAAGCCTTGCCTGTAGG

    A        ------------------------------------------------------
    B        ------------------------------------------------------
    C        -----------------------------------------------------T
    D        ------------------------------------------------------
    E        ------------------------------------------------------
    F        ------------------------------------------------------
Consensus    GAACCCAGCTGAACCAAGTTTATTAATCGATGGCACTATGTGGGAAGGTGCTTCAGGAGA
```

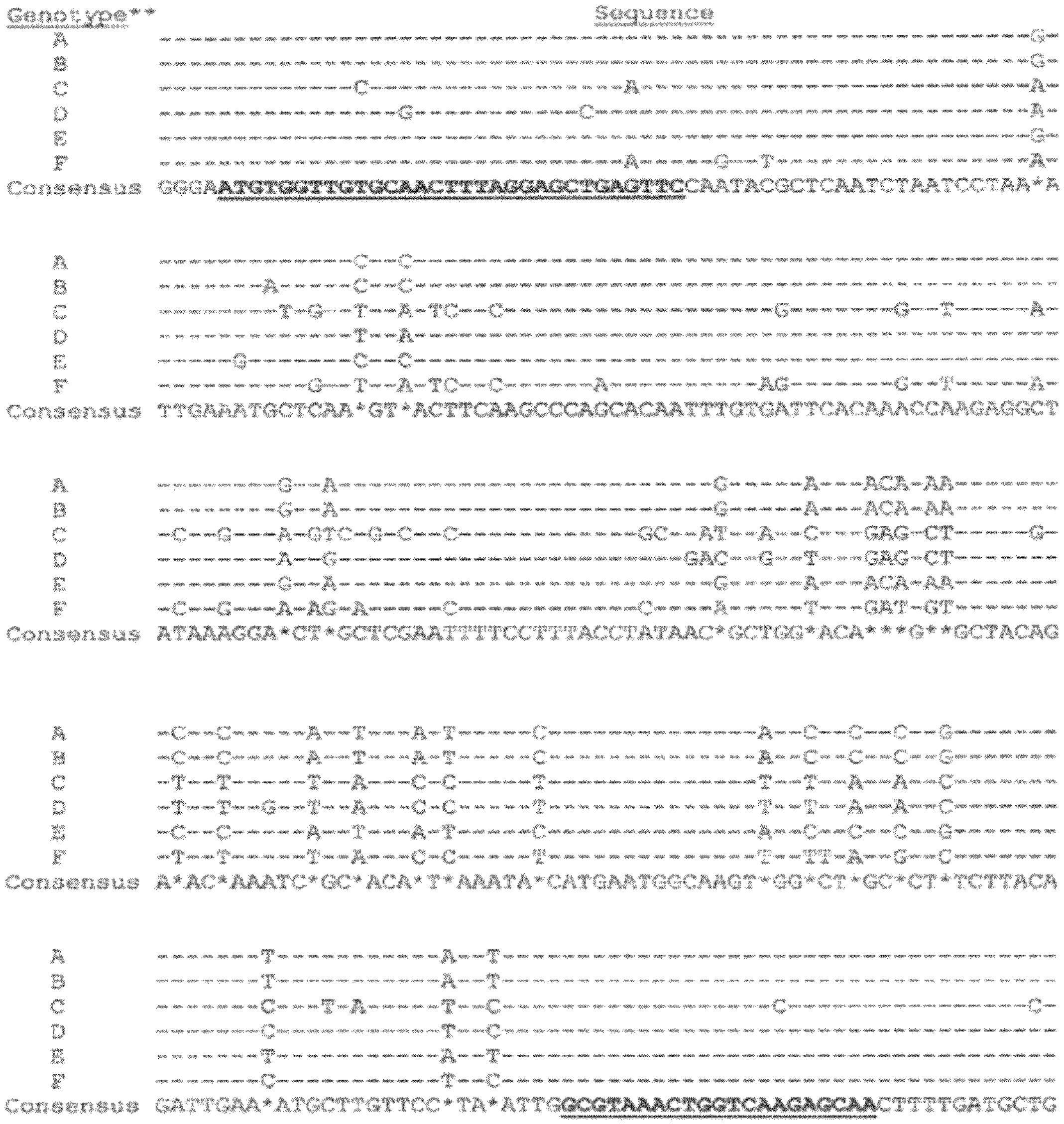

FIG. 4B

```
Genotype**                                                Sequence
    A        ---------------------------------------------------G-
    B        ---------------------------------------------------G-
    C        -------------C---------------A---------------------A-
    D        ----------------G------------C---------------------G-
    E        ---------------------------------------------------G-
    F        -----------------------------A------G--T-----------A-
Consensus    GGGAATGTGGTTGTGCAACTTTAGGAGCTGAGTTCCAATACGCTCAATCTAATCCTAA*A

    A        --------------C--C------------------------------------
    B        -----A--------C--C------------------------------------
    C        -----T-G--T--A-TC--C---------G---------G--T-------A---
    D        --------------T--A------------------------------------
    E        ----G---------C--C------------------------------------
    F        -----G--T--A-TC--C------A----------AG------G--T-----A-
Consensus    TTGAAATGCTCAA*GT*ACTTCAAGCCCAGCACAATTTGTGATTCACAAACCAAGAGGCT

    A        -----G--A--------------------G-----A----ACA-AA--------
    B        -----G--A--------------------G-----A----ACA-AA--------
    C        -C--G-----A-GTC-G-C--C------GC--AT--A--C---GAG-CT-----G-
    D        ----------A--G---------------GAC--G--T---GAG-CT-------
    E        ----G-----A------------------------A----ACA-AA--------
    F        -C--G-----A-AG-A------C------------A------T---GAT-GT----
Consensus    ATAAAGGA*CT*GCTCGAATTTTCCTTTACCTATAAC*GCTGG*ACA***G**GCTACAG

    A        -C--C----A--T---A-T----C---------A--C--C--C--G---
    B        -C--C----A--T---A-T----C---------A--C--C--C--G---
    C        -T--T----T--A---C-C----T---------T--T--A--A--C---
    D        -T--T--G--T--A---C-C----T---------T--T--A--A--C---
    E        -C--C----A--T---A-T----C---------A--C--C--C--G---
    F        -T--T-------T--A---C-C----T---------T--TT-A--G--C-----
Consensus    A*AC*AAATC*GC*ACA*T*AAATA*CATGAATGGCAAGT*GG*CT*GC*CT*TCTTACA

    A        ------T---------A---T---
    B        ------T---------A---T---
    C        -----C---T-A----T--C-----------C-----------C-
    D        -----C----------T--C---
    E        ------T---------A---T---
    F        -----C----------T--C---
Consensus    GATTGAA*ATGCTTGTTCC*TA*ATTGGCGTAAACTGGTCAAGAGCAACTTTTGATGCTG
```

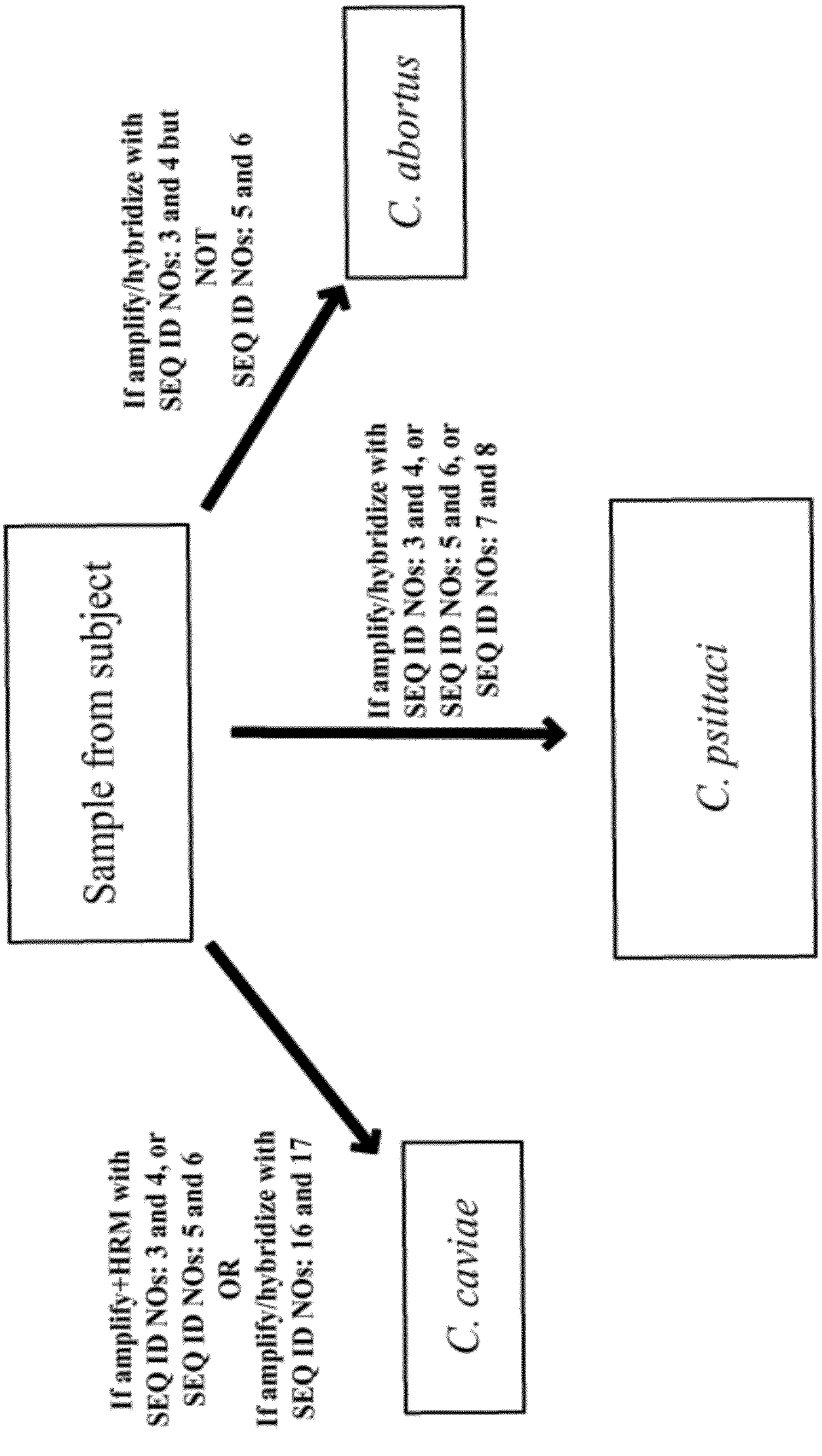

FIG. 6A

```
                    If amplify/hybridize with
                    SEQ ID NOs: 3 and 4 but
                             NOT
                    SEQ ID NOs: 5 and 6
Sample from subject ─────────────────────────→  C. abortus

                    If amplify/hybridize with
                    SEQ ID NOs: 3 and 4, or
                    SEQ ID NOs: 5 and 6, or
                    SEQ ID NOs: 7 and 8
Sample from subject ─────────────────────────→  C. psittaci

                    If amplify+HRM with
                    SEQ ID NOs: 3 and 4, or
                    SEQ ID NOs: 5 and 6
                             OR
                    If amplify/hybridize with
                    SEQ ID NOs: 16 and 17
Sample from subject ─────────────────────────→  C. caviae
```

*C. psittaci*

→ Amplify with SEQ ID NOs: 5 and 6 + HRM → Distinguish *C. psittaci* genotypes A, B, C, D/F or E If D/F curve, Amplify/hybridize with SEQ ID NOs: 7 and 8

If No → *C. psittaci* genotype D

If Yes ↓

If amplify/hybridize with SEQ ID NOs: 7 and 8 → *C. psittaci* genotype F

NUCLEIC ACIDS FOR DETECTION AND DISCRIMINATION OF GENOTYPES OF *CHLAMYDOPHILA PSITTACI*

CROSS REFERENCE TO RELATED APPLICATIONS

This is the U.S. National Stage of International Application No. PCT/US2010/036742, filed May 28, 2010, which was published in English under PCT Article 21(2), which in turn claims the benefit of U.S. Provisional Application No. 61/182,628, filed May 29, 2009, which is incorporated by reference herein in its entirety.

FIELD

This disclosure relates to nucleic acids for the detection and identification of *Chlamydophila psittaci*, as well as kits including primers and methods of using the primers to detect, diagnose and genotype *Chlamydophila psittaci*.

BACKGROUND

*Chlamydophila psittaci* (*C. psittaci*) is an intracellular pathogen and a member of the *Chlamydiaceae* family that is most frequently associated with Psittaciformes. *C. psittaci* can infect 465 avian species in 30 avian orders, but the at least 153 species in the order Psittaciformes can also infect a wide range of mammalian hosts. *C. psittaci* has the ability to remain infectious in the environment for months, which can cause economically devastating outbreaks in poultry farms and respiratory disease (psittacosis) in both mammals and birds. Transmission of this respiratory pathogen can occur through direct contact with infected birds, bird feces, nasal discharges, and aerosols. Zoonotic infections in humans usually result from close contact with infected captive birds, companion, or free-ranging birds; human-to-human transmission has also been suggested. Regardless of the transmission method, infection may lead to severe pneumonia and a wide spectrum of other medical complications. From 1988 through 2003, a total of 935 human cases of psittacosis were reported to the U.S. Centers for Disease Control and Prevention; most were related to contact with Psittaciformes. Approximately 100 psittacosis cases are reported annually in the United States, and one person may die of this disease each year. Individuals with occupations associated with commercial poultry as well as those with routine contact with companion or aviary birds are considered most at risk for infection. Laboratory-acquired infections also remain a concern.

*C. psittaci* is currently grouped into seven avian genotypes (A through F and the recently identified genotype, E/B) and two non-avian genotypes (M56 and WC). Recent reclassification of *C. psittaci* has resulted in the separation of *C. abortus* and *C. caviae* into distinct species, although these species are genetically closely related.

There is a need for methods to quickly and reliably detect *C. psittaci*. This will aid in treatment, as quick diagnosis will improve treatment outcomes.

SUMMARY

Disclosed herein are methods for the detection and identification of *C. psittaci*. In several embodiments, the methods can detect and identify each of the individual avian *C. psittaci* genotypes. In addition, the methods can be used to identify and discriminate between closely related strains, such as *C. caviae* and *C. abortus*. The methods are useful for determining the existence of genetic variants within the *C. psittaci* species. The versatility of the methods also makes it useful in many applications, such as, but not limited to, (i) improving the timely reporting of results to facilitate epidemiological investigations; (ii) pathogenicity and transmission studies; (iii) prospective screening of companion birds or livestock; (iv) current and retrospective analysis of specimens collected during an outbreak of *C. psittaci*; and (v) a greater characterization of this pathogen, leading to a better understanding of *C. psittaci* infection within human and avian populations. In some embodiments, the disclosed methods contribute to the development of an all-inclusive molecular typing system for this pathogen. In additional embodiments, these methods will also provide valuable information for designing public health measures during a *C. psittaci* outbreak.

In particular examples, the methods for the detection and identification of *Chlamydophila* involve direct dection of a hybridized primer or probe, such as by Southern blot or dot blot analysis. In other examples, hybridized primers or probes are further used to direct amplification of a target *Chlamydophila* nucleic acid, which is then detected using a label such as a self-quenching fluororophore or by hybridization of a labeled probe to the amplified product.

In some embodiments, primers are provided that are specific for the amplification of a *Chlamydophila* nucleic acid. In other embodiments, the present disclosure relates to primers that are specific for the amplification of a *C. psittaci* nucleic acid. These primers are 15 to 40 nucleotides in length and include a nucleic acid set forth as SEQ ID NO: 3, SEQ ID NO: 4, SEQ ID NO: 5, SEQ ID NO: 6, SEQ ID NO: 7, or SEQ ID NO: 8, and are capable of directing amplification of a *Chlamydophila psittaci* nucleic acid in a sample. In another embodiment, the primers include 15 to 40 nucleotides of a nucleic acid sequence at least 95% identical to SEQ ID NO: 3, SEQ ID NO: 4, SEQ ID NO: 5, SEQ ID NO: 6, SEQ ID NO: 7 or SEQ ID NO: 8. In yet another example, the primers include, or consist of a nucleic acid sequence that consists essentially of, SEQ ID NO: 3, SEQ ID NO: 4, SEQ ID NO: 5, SEQ ID NO: 6, SEQ ID NO: 7 or SEQ ID NO: 8.

The foregoing and other objects, features, and advantages of the invention will become more apparent from the following detailed description, which proceeds with reference to the accompanying figures.

BRIEF DESCRIPTION OF THE DRAWINGS

FIG. 3A is a HRM analysis curve obtained from the melting of a sample containing *Chlamydophila* nucleic acids with a *Chlamydophila*-specific primer. FIG. 3B is a HRM analysis curve obtained from the melting of a sample containing *C. psittaci* nucleic acids with a *C. psittaci*-specific primer. FIG. 3C is a HRM curve obtained from the melting of a sample containing *C. psittaci* nucleic acids with a *C. psittaci* genotype F-specific primer.

FIGS. 4A-4B is a sequence alignment of *C. psittaci* genotypes. FIG. 4A is a sequence alignment of Ppac amplicons and shows the consensus sequence (SEQ ID NO: 18). Only the sequence of the genotype C Ppac amplicon (SEQ ID NO: 19) was divergent from the consensus sequence. FIG. 4B is a sequence alignment of GTpc amplicons and shows the consensus sequence (SEQ ID NO: 20). The genotype A-F GTpc amplicon sequences (SEQ ID NOs 21-26) are also shown and are highly divergent from the consensus sequence. A dash (-) indicates identical sequences; a * indicates no consensus sequence. Each genotype (**) is presented by reference strains and, where applicable, specimen sequences. Genotype A includes DD34 and specimens 25 and 83; genotype B includes CP3 and specimens 30 and 31; genotype C includes CT1, genotype D includes NJ1, genotype E includes Vr-122 and specimens 3 and 5, and genotype F includes VS-225. Underscored and bold portions of the sequences are primer binding locations.

FIG. 5A is an amplification plot for the amplification of *C. psittaci* nucleic acids using *C. caviae* specific primers. All of the *C. psittaci* samples were observed to amplify below the threshold value considered sufficient for amplification of *C. caviae* nucleic acids. FIG. 5B discloses an amplification plot for samples that were archived with the University of Georgia as being *C. caviae* positive. The majority of samples were found to amplify above the threshold value sufficient to be positively identified as a *C. caviae* nucleic acid. It is likely that long-term storage conditions and/or solutions used during the preparation of some of the original samples adversely affected those test samples, resulting in amplification levels lower than the threshold value and thus no determination of bacterial source could be made.

SEQUENCE LISTING

Figure 1:
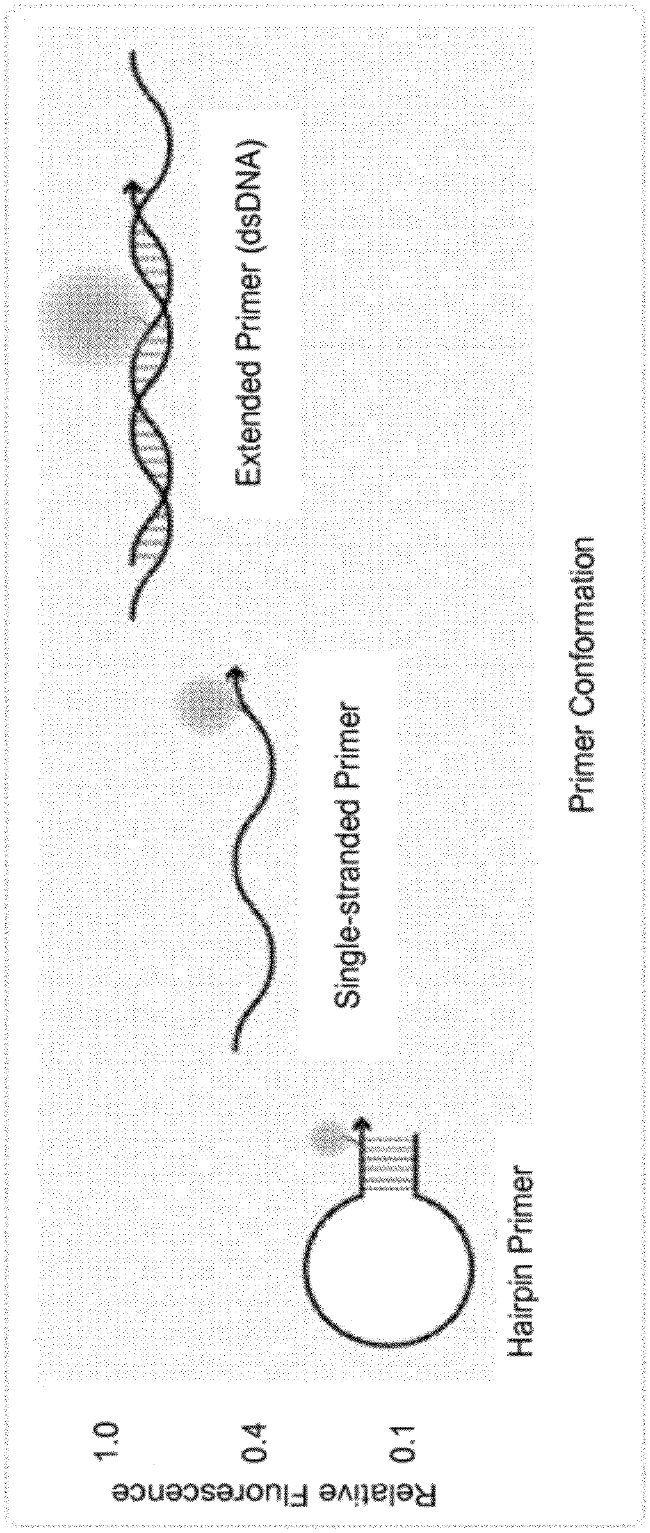
FIG. 1 is a schematic representation of a generalized procedure for hybridizing and amplifying *C. psittaci* nucleic acids with *C. psittaci* specific LUX™ primers.
Figure 2:
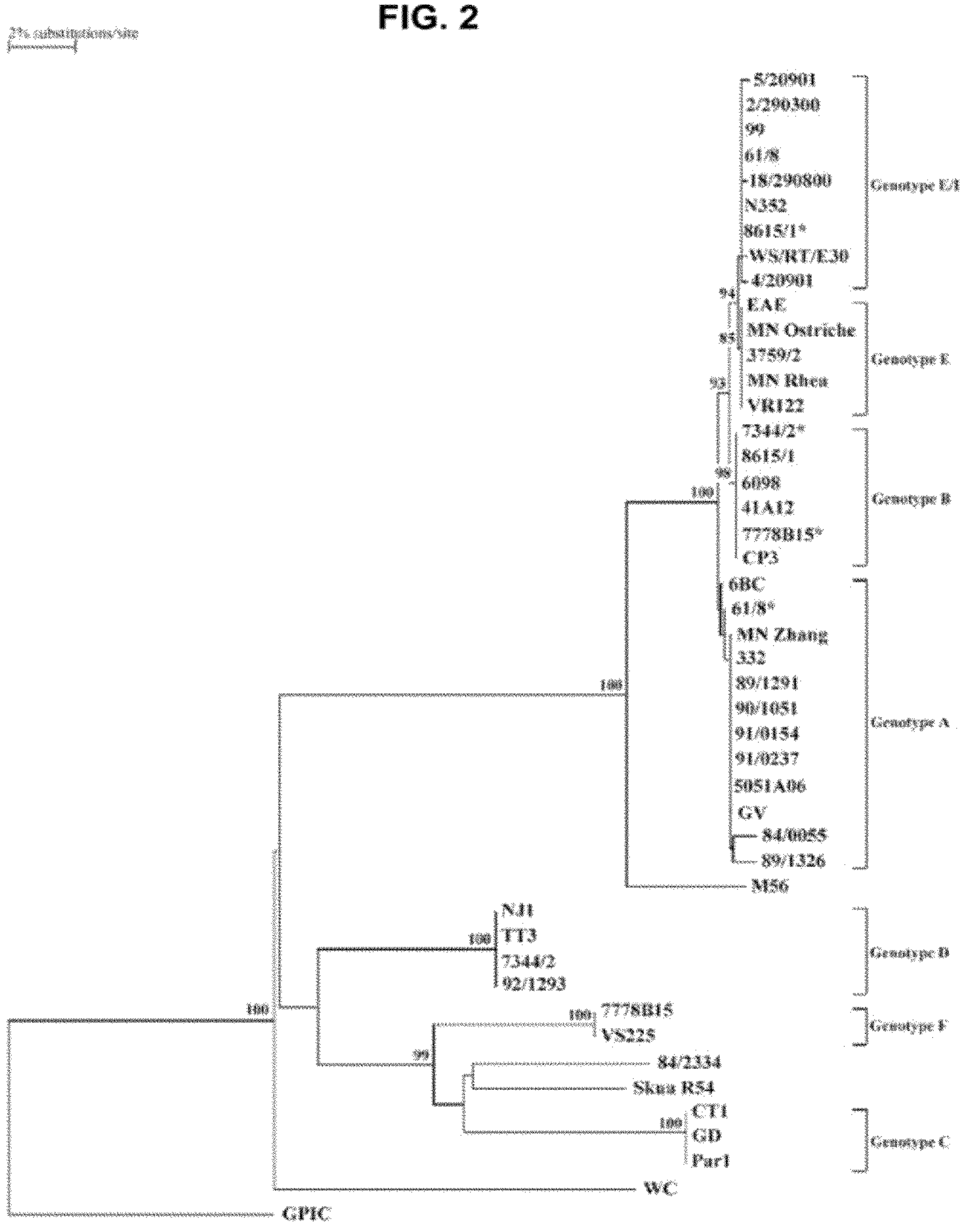
FIG. 2 is a phylogenetic tree of the ompA gene.

The nucleic and amino acid sequences listed in the accompanying sequence listing are shown using standard letter abbreviations for nucleotide bases, and one letter code for amino acids, as defined in 37 C.F.R. §1.822. If only one strand of each nucleic acid sequence is shown, the complementary strand is understood as included by any reference to the displayed strand. The Sequence Listing is submitted as an 18.9 KB ASCII text file named "seq listing_82676-02.txt," which was last modified on May 21, 2010, and which is incorporated by reference herein.

SEQ ID NO: 1 is the nucleotide sequence of a theoretical oligo.

SEQ ID NO: 2 is the nucleotide sequence of a theoretical oligo.

SEQ ID NO: 3 is the nucleotide sequence of a *C. psittaci* ompA (Ppac) forward real-time PCR primer.

SEQ ID NO: 4 is the nucleotide sequence of a *C. psittaci* ompA (Ppac) reverse real-time PCR primer.

SEQ ID NO: 5 is the nucleotide sequence of a *C. psittaci* ompA (GTpc) forward real-time PCR primer.

SEQ ID NO: 6 is the nucleotide sequence of a *C. psittaci* ompA (GTpc) reverse real-time PCR primer.

SEQ ID NO: 7 is the nucleotide sequence of a *C. psittaci* ompA (GT-F) forward real-time PCR primer.

SEQ ID NO: 8 is the nucleotide sequence of a *C. psittaci* ompA (GT-F) reverse real-time PCR primer.

SEQ ID NO: 9 is the nucleotide sequence of a *C. psittaci* ompA (ompA) forward real-time PCR primer.

SEQ ID NO: 10 is the nucleotide sequence of a *C. psittaci* ompA (ompA) reverse real-time PCR primer.

SEQ ID NO: 11 is an exemplary nucleotide sequence of the *C. psittaci* MOMP gene (GENBANK® Accession no. X56980).

SEQ ID NO: 12 is an exemplary nucleotide sequence of the *C. psittaci* ompA gene (GENBANK® Accession no. AY762608).

SEQ ID NO: 13 is an exemplary nucleotide sequence of *C. psittaci* ompA (GENBANK® Accession no. AY762612).

SEQ ID NO: 14 is an exemplary nucleotide sequence of *C. caviae* ompA (GENBANK® Accession no. AF269282).

SEQ ID NO: 15 is an exemplary nucleotide sequence of *C. abortus* ompA (GENBANK® Accession no. CR848038).

SEQ ID NO: 16 is the nucleotide sequence of a *C. caviae* ompA reverse real-time PCR reverse primer.

SEQ ID NO: 17 is the nucleotide sequence of a *C. caviae* ompA forward real-time PCR forward primer.

SEQ ID NO: 18 is the consensus nucleotide sequence of the Ppac amplicon of *C. psittaci.*

SEQ ID NO: 19 is the nucleotide sequence of the Ppac amplicon of *C. psittaci* Genotype C.

SEQ ID NO: 20 is the consensus nucleotide sequence of the GTpc amplicon of *C. psittaci.*

SEQ ID NO: 21 is the nucleotide sequence of the GTpc amplicon of *C. psittaci* Genotype A.

SEQ ID NO: 22 is the nucleotide sequence of the GTpc amplicon of *C. psittaci* Genotype B.

SEQ ID NO: 23 is the nucleotide sequence of the GTpc amplicon of *C. psittaci* Genotype C.

SEQ ID NO: 24 is the nucleotide sequence of the GTpc amplicon of *C. psittaci* Genotype D.

SEQ ID NO: 25 is the nucleotide sequence of the GTpc amplicon of *C. psittaci* Genotype E.

SEQ ID NO: 26 is the nucleotide sequence of the GTpc amplicon of *C. psittaci* Genotype F.

DETAILED DESCRIPTION

Several standard Polymerase Chain Reaction (PCR) techniques have been developed for the detection and identification of *C. psittaci*. Most of them target major outer membrane protein (MOMP) genes. Identification and genotyping of *C. psittaci* in avian samples and isolates is currently achieved by serological testing and molecular methods, such as outer membrane protein A (ompA) gene sequencing, restriction fragment length polymorphism (RFLP), and microarray analysis. Traditionally, sequence analysis of the ompA gene has been considered the most accurate method for identifying all known genotypes. For diagnosis in humans, serological testing is rarely performed because the procedure is labor-intensive and requires specialized laboratory expertise and equipment. Thus, accurate diagnosis of *C. psittaci* infection is often delayed or missed and may result in improper treatment for patients. Diagnosis by molecular techniques, such as real-time PCR, is not readily available in most public health laboratories, forcing them to rely upon insensitive complement fixation or micro-immunofluorescence tests for detecting *C. psittaci* antibodies in suspect cases. Since both complement fixation and micro-immunofluorescence require acute and convalescent-phase sera, they are retrospective assays that are considered inadequate for a timely diagnosis.

Other newly developed molecular methods have improved upon the traditional approaches of ompA sequencing and RFLP to genotype *C. psittaci*. These methods include DNA microarrays, real-time PCR assays for detecting amplified product using minor-groove binding probes and competitor oligonucleotides, and a multilocus variable-number tandem repeat analysis. However, there exists no rapid, simple and inexpensive procedure which can effectively discriminate among the known genotypes of *C. psittaci* and have the capability of identifying new strains in view of the significant genetic heterogeneity found within this species. Hence the need remains for a reliable and rapid assay for detecting and genotyping *C. psittaci*, so that diagnosis is completed in sufficient time to permit effective treatment of an infected subject.

The disclosed methods detect and identify *C. psittaci*. In particular examples, the methods for the detection and identification of *Chlamydophila* involve direct dection of a hybridized primer or probe, such as by Southern blot or dot blot analysis. In other examples, hybridized primers or probes are further used to direct amplification of a target *Chlamydophila* nucleic acid, which is then detected using a label such as a self-quenching fluororophore. In several embodiments, the methods can detect and identify each of the individual avian *C. psittaci* genotypes. In addition, the methods can identify and discriminate between closely related strains, such as *C. caviae* and *C. abortus*, and determine the existence of genetic variants within the *C. psittaci* species. An example of the methods of distinguishing between *Chlamydophila* species is presented in FIG. 6A.

In one aspect, the disclosure relates to primers that are specific for the hybridization to and amplification of a *Chlamydophila* nucleic acid. Primers are disclosed that are specific for the amplification of a *C. psittaci* nucleic acid. In some embodiments, these primers include a nucleic acid set forth as SEQ ID NO: 3, SEQ ID NO: 4, SEQ ID NO: 5, SEQ ID NO: 6, SEQ ID NO: 7, or SEQ ID NO: 8, which are capable of directing amplification of a *Chlamydophila psittaci* nucleic acid in a sample. In another embodiment, the primers are at least 95% or 98% identical to these disclosed sequences, or consist essentially of one of SEQ ID NOs: 3-8

In some embodiments, the primers are capable of hybridizing to and amplifying a *Chlamydophila* nucleic acid, such as a *C. psittaci* nucleic acid or the nucleic acid of a particular *C. psittaci* genotype. In several embodiments, the primers are between 15 and 40 nucleotides in length and are capable of hybridizing under very high stringency conditions to the complement of nucleic acids of *C. psittaci* genotypes A, B, C, D, E or F. In another aspect, the primers are capable of hybridizing under very high stringency conditions to the complement of nucleic acids of *Chlamydophila psittaci* genotypes A, B, C or E and include a nucleic acid sequence at least 95% identical to primers set forth as SEQ ID NO: 5 or SEQ ID NO: 6. In yet another aspect, the disclosure relates to primers that are capable of hybridizing under very high stringency conditions to a nucleic acid of *Chlamydophila psittaci* genotype F and include a nucleic acid sequence at least 95% identical to primers set forth as SEQ ID NO: 7 or SEQ ID NO: 8.

In some aspects, the *C. psittaci* species-specific primers are a pair of primers, and the pair of primers is capable of hybridizing to and directing the specific amplification of complementary *C. psittaci* nucleic acids. In one aspect, the pair of primers include one or more forward primers with a nucleic acid sequence set forth as SEQ ID NO: 3, SEQ ID NO: 5, or SEQ ID NO: 7; and one or more reverse primers with a nucleic acid sequence set forth as SEQ ID NO: 4, SEQ ID NO: 6, or SEQ ID NO: 8. In another aspect, the pair of primers include one or more forward primers with a nucleic acid sequence at least 95% identical to a nucleic acid sequence set forth as SEQ ID NO: 3, SEQ ID NO: 5, or SEQ ID NO: 7; and one or more reverse primers with a nucleic acid sequence at least 95% identical to a nucleic acid sequence set forth as SEQ ID NO: 4, SEQ ID NO: 6, or SEQ ID NO: 8. In yet another aspect, the pair of primers include one or more forward primers with a nucleic acid sequence that consists essentially of or consists of SEQ ID NO: 3, SEQ ID NO: 5, or SEQ ID NO: 7; and one or more reverse primers with a nucleic acid sequence that consists essentially of SEQ ID NO: 4, SEQ ID NO: 6, or SEQ ID NO: 8. In some embodiments, the pair of primers specific for the detection and identification of *C. psittaci* nucleic acids in a sample are 15 to 40 nucleotides in length and include a nucleic acid sequence at least 95% identical to the nucleotide sequence set forth as SEQ ID NO: 3, SEQ ID NO: 4, SEQ ID NO: 5, SEQ ID NO: 6, SEQ ID NO: 7, or SEQ ID NO: 8.

In another embodiment, the disclosure relates to primers capable of hybridizing to and amplifying a *Chlamydophila* nucleic acid, such as a *C. caviae* or *C. abortus* nucleic acid. In some embodiments, the primers are between 15 and 40 nucleotides in length and are capable of hybridizing under very high stringency conditions to a *C. caviae* or *C. abortus* nucleic acid in a sample. In one embodiment, the primers capable of hybridizing to and amplifying a *C. caviae* nucleic acid include or consist of a nucleic acid sequence set forth as SEQ ID NO: 16, or SEQ ID NO: 17. In another embodiment, the primers capable of hybridizing to and amplifying a *C. caviae* nucleic acid include a nucleic acid sequence at least 95% identical to a nucleic acid sequence set forth as SEQ ID NO: 16, or SEQ ID NO: 17, or consists essentially of SEQ ID NO: 16, or SEQ ID NO: 17.

In some embodiments, the nucleic acids are genotype-specific for the detection and identification of *C. psittaci* genotypes, and are used in methods of detecting and/or discriminating between *C. psittaci* genotypes. In one aspect, detecting hybridization of a nucleic acid sequence at least 95% identical to SEQ ID NO: 3 or SEQ ID NO: 4 with a sample suspected of containing a *Chlamydophila* nucleic acid indicates the presence of *C. psittaci, C. caviae* or *C. abortus* in the sample. In another example, detecting hybridization of a nucleic acid sequence at least 95% identical to SEQ ID NO: 5 or SEQ ID NO: 6 with a sample suspected of containing a *Chlamydophila* nucleic acid indicates the presence of *C. psittaci* in the sample, such as *C. psittaci* genotype A, B, C, D, E or F, or a combination thereof. In yet another example, detecting hybridization of a nucleic acid sequence at least 95% identical to SEQ ID NO: 7 or SEQ ID NO: 8 with a sample suspected of containing a *Chlamydophila* nucleic acid indicates the presence of *C. psittaci* genotype F. In one example, detecting hybridization of a nucleic acid sequence at least 95% identical to SEQ ID NO: 16 or SEQ ID NO: 17 with a sample suspected of containing a *Chlamydophila* nucleic acid indicates the presence of *C. caviae.*

As demonstrated by the example presented in FIGS. 6A and B, methods are also disclosed for detecting in a sample the presence of *Chlamydophila*, such as *Chlamydophila psittaci* (*C. psittaci*), for example in a biological sample obtained from a subject. The disclosed methods can be used for diagnosing a *C. psittaci* infection or confirming diagnosis of a *C. psittaci* infection in a subject by analyzing a biological specimen from the subject and detecting the presence of *C. psittaci* nucleic acids and/or the specific *C. psittaci* genotype in the sample. Alternatively, the method can be used to quickly discriminate between *Chlamydophila* species, such as *C. psittaci, C. caviae* and *C. abortus.*

In some embodiments, the detection method involves contacting a biological sample suspected of containing a *C. psittaci* nucleic acid with a *C. psittaci* species-specific or genotype-specific primer or probe, and detecting hybridization between the *C. psittaci* nucleic acid in the sample and the *C. psittaci* primer or probe. In some embodiments, the primer is detectably labeled for instance with a fluorophore. In one embodiment, the method involves amplifying *C. psittaci* nucleic acids present in a sample, for example by Polymerase Chain Reaction (PCR) techniques. In another aspect, the method involves amplifying *C. psittaci* nucleic acids present in a sample with a *C. psittaci* specific primer in combination with high-resolution melt (HRM) analysis to specifically detect, identify and genotype *C. psittaci* nucleic acids in the sample. In some embodiments, the primer is a *C. psittaci* species-specific primer with a nucleic acid sequence set forth as SEQ ID NO: 3, SEQ ID NO: 4, SEQ ID NO: 5, SEQ ID NO: 6, SEQ ID NO: 7, or SEQ ID NO: 8, or a nucleic acid sequence that is 95% identical thereto.

In a further embodiment, the detection method relates to primers or probes that are *C. psittaci* genotype specific. These methods include contacting a sample suspected of containing a *C. psittaci* nucleic acid with a primer or probe specific for a *C. psittaci* genotype and detecting hybridization between the *C. psittaci* nucleic acids in the sample and the *C. psittaci* genotype-specific primer. Detection of the hybridization between the *C. psittaci* genotype-specific primer or probe and the sample indicates that *C. psittaci* nucleic acids and at least one *C. psittaci* genotype is present in the sample. In some embodiments, the primer or probe is specific for the detection and identification of one or more *C. psittaci* genotypes. In another embodiment, the *C. psittaci* primer or probe is specific for the detection and identification of a single genotype selected from *C. psittaci* genotypes A, B, C, D, E or F. In other embodiments, the *C. psittaci* primer or probe is specific for the identification of *C. psittaci* genotypes A, B, C and E. In a further embodiment, the *C. psittaci* primer or probe is specific for the identification of *C. psittaci* genotype F.

The disclosure provides panels of primers that permit rapid evaluation of a subject with an apparent illness by quickly determining whether the illness is caused by *C. psittaci*. This rapid evaluation involves ruling out the presence of other bacterial, viral and *Chlamydophila* species (for example, by positively identifying a *C. psittaci* nucleic acid or *C. psittaci* genotype).

In one embodiment, the methods include amplifying the nucleic acids of a sample with at least one primer specific for *C. psittaci* to diagnose a *C. psittaci* infection. In some embodiments, the primer specific for *C. psittaci* is 15 to 40 nucleotides in length and includes a self-quenching detectable label. In one example, a pair of primers specific for the detection of *C. psittaci* or diagnosis of a *C. psittaci* infection includes a labeled primer and an unlabeled primer. In another example, nucleic acids amplified in a sample suspected of containing *Chlamydophila* with a *Chlamydophila* specific primer are subjected to high-resolution melt analysis to discriminate between the *Chlamydophila* species. In one example, high-resolution melt analysis of the amplified nucleic acids can be used to genotype *C. psittaci* nucleic acids in the sample. In another example, high-resolution melt analysis of the amplified nucleic acids can be used to discriminate between *C. psittaci, C. caviae*, or *C. abortus* nucleic acids in a sample.

In some embodiments, the primers of the disclosure are capable of hybridizing under very high stringency conditions to a *C. psittaci, C. caviae* or *C. abortus* nucleic acid. In one embodiment, the primer is capable of hybridizing under very high stringency conditions to a nucleic acid sequence set forth as SEQ ID NO:13, SEQ ID NO:14, or SEQ ID NO:15. In another embodiment, a *C. caviae* specific primer is capable of hybridizing under very high stringency conditions to a nucleic acid sequence set forth as SEQ ID NO: 14. In yet another embodiment, a *C. abortus* specific primer is capable of hybridizing under very high stringency conditions to a nucleic acid sequence set forth as SEQ ID NO: 15.

Additional methods for detecting or genotyping *C. psittaci* in a sample include amplifying the nucleic acids in the sample with at least one *C. psittaci* and/or *C. psittaci* genotype specific primer by PCR, real-time PCR, RT-PCR, rt RT-PCR, ligase chain reaction or transcription mediated amplification.

The disclosure also provides kits for detecting and/or genotyping *C. psittaci* in a sample suspected of containing a *C. psittaci* infection. In one embodiment, the kit includes one or more primers as set forth as SEQ ID NO: 3, SEQ ID NO: 4, SEQ ID NO: 5, SEQ ID NO: 6, SEQ ID NO: 7, or SEQ ID NO: 8. In another embodiment, the kit provides for the detection of *C. caviae* in a sample, the kit including one of more primers set forth as SEQ ID NO: 16, or SEQ ID NO: 17.

I. Abbreviations

| | |
|---|---|
| cDNA | complementary DNA |
| ds | double stranded |
| DNA | deoxyribonucleic acid |
| dNTP | deoxyribonucleotides |
| FAM | carboxyfluorescein |
| FRET | fluorescence resonance energy transfer |
| HRM | high-resolution melt |
| JOE | 2,'7'-dimethoxy-4',5'-dichloro-6-carboxyfluorescein |
| LLD | lower limit of detection |
| MEM | minimal essential medium |
| MOMP | major outer membrane protein |
| ompA | outer membrane protein A |
| PCR | polymerase chain reaction |
| RFLP | restriction fragment length polymorphism |
| RT-PCR | reverse transcriptase polymerase chain reaction |
| rt RT-PCR | real-time reverse transcriptase polymerase chain reaction |
| RNA | ribonucleic acid |
| UTR | untranslated regions |
| ss | single stranded |
| TMA | transcription-mediated amplification |

II. Explanation Of Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a primer" includes single or plural primers and can be considered equivalent to the phrase "at least one primer."

As used herein, the term "comprises" means "includes." Thus, "comprising a primer" means "including a primer" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Animal: A living multi-cellular vertebrate or invertebrate organism, a category that includes, for example, mammals and birds. The term mammal includes both human and non-human mammals. Similarly, the term "subject" includes both human and veterinary subjects, such as birds or guinea pigs.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR; real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from RNA.

Change: To become different in some way, for example to be altered, such as increased or decreased. A detectable change is one that can be detected, such as a change in the intensity, frequency or presence of an electromagnetic signal, such as fluorescence. In some examples, the detectable change is a reduction in fluorescence intensity. In some examples, the detectable change is an increase in fluorescence intensity. In some examples, the detectable change is a change in florescence intensity as a result of a DNA melting curve of a test sample.

*Chlamydophila abortus: Chlamydophila abortus* (*C. abortus*) are gram-negative intracellular bacteria belonging to the Chlamydiaceae family. *C. abortus* is a species in Chlamydiae that causes abortion and fetal death in mammals, including humans. *C. abortus* was previously classified as *Chlamydophila psittaci* along with all Chlamydiae except *Chlamydia trachomatis*. This was based on a lack of evident glycogen production and on resistance to the antibiotic sulfadiazine. In 1999, *C. psittaci* and *C. abortus* were recognized as distinct species based on differences of pathogenicity and DNA-DNA reassociation.

*C. abortus* is endemic among ruminants and has been associated with abortion in a horse, a rabbit, guinea pigs, mice, pigs and humans. Infected females shed bacteria near the time of ovulation, so *C. abortus* is transmitted orally and sexually among mammals. All *C. abortus* strains were isolated or PCR-amplified from placenta or fetal organs after spontaneous abortion. *C. abortus* infection generally remains unapparent until an animal aborts late in gestation or gives birth to a weak or dead fetus. *C. abortus* has not been isolated from birds.

*Chlamydophila caviae: Chlamydophila caviae* (*C. caviae*) are gram-negative intracellular bacteria belonging to the Chlamydiaceae family. *C. caviae* is markedly specific for guinea pigs. Attempts to infect rabbits, mice, and hamsters have been unsuccessful. *C. caviae* infects primarily the mucosal epithelium and is not invasive.

*Chlamydophila psittaci: Chlamydophila psittaci*(*C. psittaci*) are gram-negative intracellular bacteria belonging to the Chlamydiacea family. *C. psittaci* are classified on the basis of their genotypes designated A, B, C, D, E, F, and E/B in avian and two non-avian genotypes (M56 (rodents) and WC (cattle)). Within these broad classifications, the genotypes can be further characterized based on their serovars. Serovar A is endemic among psittacine birds and causes zoonotic disease in humans. Serovar B is endemic among pigeons, has been isolated from turkeys, and can cause abortion in a dairy herd. Serovar C isolates (GD, MT1, 91/1264, 91/1301, CT1 and Par1) were obtained from a German, Bulgarian and Belgian duck, a white swan, and a Californian turkey and a partridge, respectively. Serovar D has mainly been isolated from turkeys but also from a seagull, a budgerigar, and from humans. Serovars C and D are known occupational hazards for poultry workers. Serovar E isolates, known as Cal-10, MP, or MN (meningopneumonitis), were isolated during an outbreak of human pneumonitis in the late 1920s and early 1930s. Subsequently, MN isolates have been obtained from a variety of birds worldwide, including ducks, pigeons, ostriches, and rheas. A single serovar F isolate, was obtained from a parakeet.

Direct detection of *C. psittaci* by cell culture is hazardous and requires a level 3 laboratory, given its contagiousness. However, the interpretation of serodiagnosis is difficult because of cross-reactions with other species of *Chlamydia* and the high prevalence of *Chlamydia pneumoniae* in the general population.

Identification and genotyping of *C. psittaci* in avian samples and isolates is currently achieved by molecular methods such as outer membrane protein A (ompA) gene sequencing, restriction fragment length polymorphism (RFLP), real-time PCR and microarray analysis. There are obvious limitations to these techniques as substantial amounts of a PCR amplicon are needed to produce distinctive and reproducible RFLP patterns on ethidium bromide-stained agarose gels. Related genotypes tend to have quite similar patterns, which may be difficult to distinguish, and typing results based on different enzyme patterns (e.g. AluI vs. MboII) may be contradictory. For example, *C. psittaci* isolates were initially characterized by RFLP by Alul restriction mapping of the major outer membrane protein gene ompl obtained after amplification by the polymerase chain reaction. Digestion of *C. psittaci* ompl amplicons by Alul generated several of the known distinct restriction patterns (A, B, D, E and F). However, restriction pattern C was not observed. Additionally, genetically aberrant strains cannot be genotyped using the above-mentioned PCR-RFLP procedure. Sequencing of the ompA gene and alignment with type strain sequences can also be used to identify the genotype of *C. psittaci* strains, since genotype-specific sites are located in the gene's variable domains (VD) VD2 and VD4, however this technique is time intensive. While the above techniques have improved upon the traditional approaches to detect *C. psittaci*, they still lack specificity and/or sensitivity to rapidly and accurately detect and discriminate *C. psittaci* genotypes in a biological sample.

*C. psittaci* 6BC ompA gene (ompA): The ompA-encoded gene of *C. psittaci*. As used herein "ompA" refers to the nucleotide sequence of ompA, thus a probe or primer for ompA, such as those disclosed herein, capable of hybridizing to the nucleotide sequence of ompA, such as the ompA nucleotide sequence given below (or the complement thereof).

An exemplary nucleotide sequence of *C. psittaci* 6BC ompA as found at GENBANK® Accession number X56980 on Mar. 13, 2009 is shown below:

(SEQ ID NO: 11)

ttacactcttctacgagggtaattccaacttattctaagtggcataagaaataaaaatgtgtacaaaaatctgatagctcttta ttagcaagtataaggagttattgcttgaaatctatgcctgaaaacagtctttttttcttatcgtctttactataataagaaaagtttg ttatgttttcgaataatgaactgtatgttcatgcttaaggctgttttcacttgcaagacactcctcaaagccattaattgcctaca ggatatcttgtctggctttaacttggacgtggtgccgccagaagagcaaattagaatagcgagcacaaaaagaaaagata ctaagcataatctttagaggtgagtatgaaaaaactcttgaaatcggcattattgtttgccgctacgggttccgctctctcctt acaagccttgcctgtagggaacccagctgaaccaagtttattaatcgatggcactatgtgggaaggtgcttcaggagatc cttgcgatccttgcgctacttggtgtgacgccattagcatccgcgcaggatactacggagattatgttttcgatcgtgtattaa aagttgatgtgaataaaacttttagcggcatggctgcaactcctacgcaggctacaggtaacgcaagtaatactaatcagc cagaagcaaatggcagaccgaacatcgcttacggaaggcatatgcaagatgcagagtggttttcaaatgcagccttccta gccttaaacatttgggatcgcttcgacattttctgcaccttaggggcatccaatggatacttcaaagcaagttcggctgcatt caacttggttgggttaatagggttttcagctgcaagctcaatctctaccgatcttccaatgcaacttcctaacgtaggcattac ccaaggtgttgtggaattttatacagacacatcattttcttggagcgtaggtgcacgtggagctttatgggaatgtggttgtg caactttaggagctgagttccaatacgctcaatctaatcctaagattgaaatgctcaacgtcacttcaagcccagcacaattt gtgattcacaaaccaagaggctataaaggagctagctcgaattttcctttacctataacggctggaacaacagaagctaca gacaccaaatcagctacaattaaataccatgaatggcaagtaggcctcgccctgtcttacagattgaatatgcttgttccata tattggcgtaaactggtcaagagcaacttttgatgctgatactatccgcattgctcaacctaaattaaaatcggagattcttaa cattactacatggaacccaagccttataggatcaaccactgctttgcccaataatagtggtaaggatgttctatctgatgtctt gcaaattgcttcgattcagatcaacaaaatgaagtctagaaaagcttgtggtgtagctgttggtgcaacgttaatcgacgct gacaaatggtcaatcactggtgaagcacgcttaatcaatgaaagagctgctcacatgaatgctcaattcagattctaagga tttagtttatactatcctaacttttaaaccgctatcagaacctgggagtctccgggttctgatttttaaataccacccttttc.

*C. psittaci* 90/105 ompA gene (ompA): The ompA-encoded gene of *C. psittaci*. As used herein "ompA" refers to the nucleotide sequence of ompA, thus a probe or primer for ompA, such as those disclosed herein, capable of hybridizing to the nucleotide sequence of ompA, such as the ompA nucleotide sequence given below (or the complement thereof).

An exemplary nucleotide sequence of *C. psittaci* 90/105 ompA as found at GENBANK® Accession number AY762608 on Mar. 13, 2009 is shown below:

(SEQ ID NO: 12)

atgaaaaaactcttgaaatcggcattattgtttgccgctacgggttccgctctctccttacaagccttgcctgtagggaaccc agctgaaccaagtttattaatcgatggcactatgtgggaaggtgcttcaggagatccttgcgatccttgcgctacttggtgt gacgccattagcatccgcgcaggatactacggagattatgttttcgatcgtgtattaaaagttgatgtgaataaaacttttag cggcatggctgcaactcctacgcaggctacaggtaacgcaagtaatactaatcagccagaagcaaatggcagaccgaa catcgcttacggaaggcatatggaagatgcagagtggttttcaaatgcagccttcctagccttaaacatttgggatcgcttc gacattttctgcaccttaggggcatccaatggatacttcaaagcaagttcggctgcattcaacttggttgggttaatagggttt tcagctgcaagctcaatctctaccgatcttccaacgcaacttcctaacgtaggcattacccaaggtgttgtggaattttatac agacacatcattttcttggagcgtaggtgcacgtggagctttatgggaatgtggttgtgcaactttaggagctgagttccaat acgctcaatctaatcctaagattgaaatgctcaacgtcacttcaagcccagcacaatttgtgattcacaaaccaagaggcta taaaggagctagctcgaattttcctttacctataacggctggaacaacagaagctacagacaccaaatcagctacaattaa ataccatgaatggcaagtaggcctcgccctgtcttacagattgaatatgcttgttccatatattggcgtaaactggtcaagag caacttttgatgctgatactatccgcattgctcaacctaaattaaaatcggagattcttaacattactacatggaacccaagcc ttataggatcaaccactgctttgcccaataatagtggtaaggatgttctatctgatgtcttgcaaattgcttcgattcagatcaa caaaatgaagtctagaaaagcttgt

*C. psittaci* 7778B15 ompA gene (ompA): The ompA-encoded gene of *C. psittaci*. As used herein "ompA" refers to the nucleotide sequence of ompA, thus a probe or primer for ompA, such as those disclosed herein, is capable of hybridizing to the nucleotide sequence of ompA, such as the ompA nucleotide sequence given below (or the complement thereof). An exemplary nucleotide sequence of *C. psittaci* 7778B15 ompA as found at GENBANK® Accession number AY762612 on Mar. 13, 2009 is shown below:

```
                                                               (SEQ ID NO: 13)
atgaaaaaactcttgaaatcggcattattgtttgccgctacgggttccgctctctccttacaagccttgcctgtagggaaccc

agctgaaccaagtttattaatcgatggcactatgtgggaaggtgcttcaggagatccttgcgatccttgcgctacttggtgt

gacgccattagcatccgcgcaggatactacggagattatgttttcgatcgtgtattaaaagttgatgtgaataaaactatcag

cggtatgggtgcagctcctacaggaagcgcagcagccgattacaaaactcctacagatagacccaacatcgcttatggc

aaacacttgcaagacgctgagtggttcacgaatgcagctttcctcgcattaaatatctgggatcgctttgatattttctgcaca

ttaggtgcttccaatgggtacttcaaagctagttctgctgcattcaacctcgttggtttgattggtgttaaaggaacctccgta

gcagctgatcaacttccaaacgtaggcatcactcaaggtattgttgagttttacacagatacaacattctcttggagcgtag

gtgcacgtggtgctttatgggaatgtggttgtgcaactttaggagctgaattccagtatgctcaatctaatcctaaaattgaaa

tgctgaatgtaatctccagcccaacacaatttgtagttcacaagcctagaggatacaagggaacaggatcgaactttccttt

acctctaacagctggtacagatggtgctacagatactaaatctgcaacactcaaatatcatgaatggcaagttggtttagcg

ctctcttacagattgaacatgcttgttccttacattggcgtaaactggtcaagagcaacttttgatgctgactctatccgcatcg

ctcaacctaaattagccgctgctgttttgaacttgaccacatggaacccaactcttttaggggaagctacagctttagatgct

agcaacaaattctgcgacttcttacaaatcgcttcgattcagatcaacaaaatgaagtctagaaaagcttgt
```

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Consists essentially of: A transition phrase that limits the scope of a claim to the specified materials or steps, and to those that do not materially affect the basic and novel characteristics of the claimed invention. For example, a primer or probe that consists essentially of a specified sequence can vary by an insignificant number of nucleotides that do not affect the overall sequence specificity of the primer or probe, such as a variance by one, two, three or more nucleotides.

Detect: To determine if an agent (such as a signal or particular nucleotide or amino acid) is present or absent such as by detecting the presence or absence of a detectable label. In some examples, this can further include quantification. For example, use of the disclosed primers in particular examples permits detection of a fluorescent signal, for example detection of a signal from a fluorogenic primer, which can be used to determine if a nucleic acid corresponding to a nucleic acid of *C. psittaci* is present. Detection of a nucleic acid can be direct as in the case of detection of a hybridized labeled primer or probe. In other examples, detection of a nucleic acid is indirect as in the case of hybridization of a primer or probe followed by amplification and detection of a nucleic acid sequence.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example such that energy from the laser can excite a donor but not an acceptor fluorophore.

Emission or emission signal: The light of a particular wavelength generated from a fluorophore after the fluorophore absorbs light at its excitation wavelengths.

Excitation or excitation signal: The light of a particular wavelength necessary to excite a fluorophore to a state such that the fluorophore will emit a different (such as a longer) wavelength of light.

Fluorophore: A chemical compound, which when excited by exposure to a particular stimulus such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the primers and/or probes disclosed herein are known to those of skill in the art and include those provided in U.S. Pat. No. 5,866,366 to Nazarenko et al., such as 4-acetamido-4'-isothiocyanatostilbene-2,2' disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), ALEXA FLUOR® 546, fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LIGHTCYCLER® Red 640; Cy5.5; and Cy56-carboxyfluorescein; boron dipyrromethene difluoride (BODIPY); acridine; stilbene; 6-carboxy-X-rhodamine (ROX); Texas Red; Cy3; Cy5, VIC® (Applied Biosystems); LIGHTCYCLER® Red 640; LIGHTCYCLER® Red 705; and Yakima yellow, amongst others.

Other suitable fluorophores include those known to those skilled in the art, for example those available from Invitrogen (Carlsbad, Calif.) or MOLECULAR PROBES® (Eugene, Oreg.). In particular examples, a fluorophore is used as a donor fluorophore or as an acceptor fluorophore.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7™ (Molecular Probes), QSY33™ (Molecular Probes), BLACK HOLE QUENCHERS™ (Glen Research), ECLIPSE™ DARK QUENCHER™ (Epoch Biosciences), or IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore). In other examples, the fluorophore reaction can include a self-quenching moiety such as a hairpin configuration. In one such example, LUX™ (Invitrogen, Carlsbad, Calif.) primers can be used that incorporate a fluorophore. The LUX™ primer technology uses one primer labeled with a single fluorophore and containing a self-quenching moiety in conjunction with a corresponding unlabeled primer, both custom-synthesized according to the target nucleic acid of interest. Typically 15-40 bases in length, LUX™ primers are designed with a fluorophore, such as FAM or JOE, near the 3' end of the labeled primer. The 5' end of the labeled primer includes a sequence that when in single stranded conformation forms a hairpin structure. These properties of the labeled primer intrinsically render it with fluorescence quenching capability, making a separate quenching moiety unnecessary. When the labeled primer becomes incorporated into a double-stranded PCR product, the fluorophore is de-quenched, resulting in a significant increase in fluorescent signal (see FIG. 1).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule separated by 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule.

Examples of oligonucleotides using FRET that can be used to detect amplicons include linear oligoprobes, such as HybProbes, 5' nuclease oligoprobes, such as TAQMAN® probes, hairpin oligoprobes, such as molecular beacons, scorpion primers and UNIPRIMERS™, minor groove binding probes, and self-fluorescing amplicons, such as sunrise primers.

High-Resolution Melt Analysis: High-resolution separation of double-stranded nucleic acid material with heat (melting). The temperature at which a DNA strand separates and melts when heated can vary over a wide range, depending on the sequence, the length of the strand, and the GC content of the strand. For example, melting temperatures can vary for products of the same length but different GC/AT ratio, or for products with the same length and GC content, but with a different GC distribution. Even a single base difference in heterozygous DNA can result in melting temperature shifts. Because melting temperatures vary according to these differences melting temperature profiles can be used to identify, distinguish and genotype DNA products.

Conventional (standard) melt analysis is a fundamental property of DNA that is often monitored with fluorescence. Conventional melting is performed after Polymerase Chain Reaction (PCR) on any real-time instrument to monitor product purity (dsDNA dyes) and sequence (hybridization probes). Because PCR produces enough DNA for fluorescent melting analysis, both amplification and analysis can be performed in the same tube, thus providing a closed-tube system that requires no processing step, separation step or post-amplification manipulation. Dyes that stain double stranded DNA are commonly used to identify products by their melting temperature ($T_m$). The $T_m$ of a sample is defined as the point at which half the probes have melted off the DNA. Alternatively, hybridization primers allow genotyping by melting of product/primer duplexes.

The power of DNA melting analysis depends on its resolution. Recent advances include high-resolution melt (HRM) analysis that provide superior sensitivity and superiority between samples, such as allowing a user to perform mutation scanning of a sample. Conventional studies with ultraviolet absorbance often require hours to collect high-resolution data at rates of 0.1-1.0° C./min to ensure equilibrium. In contrast, fluorescent melting analysis is usually acquired at 0.1-1.0° C./s, equilibrium is not achieved, and resolution is limited to 2-4 points/° C. In contrast, high-resolution melting can be performed rapidly with 10-100 times the data density (50-100 points/° C.) of conventional real-time PCR instruments. HRM differs from conventional PCR product melting $T_m$ measurement in two ways. First, the accuracy of the melt curve is maximized by acquiring fluorescence data over small temperature increments (as low as 0.01° C.). Second, the precise shape of the HRM curve is a function of the DNA sequence being melted, allowing amplicons containing different sequences to be discriminated on the basis of melt curve shape, irrespective of whether the amplicons share the same $T_m$. HRM analysis makes use of melt curve normalization and comparison software that allows a user to determine whether two similar melt curves differ from one another.

A melting temperature analysis can be performed on any instrument that includes a melt program. A melt program is usually performed after amplification of the target nucleic acid, such as DNA. A typical melt program includes three segments:

(i) a segment that rapidly heats the sample to a temperature high enough to denture all the DNA;

(ii) a segment that cools the samples to below the annealing temperature of the target DNA; and (iii) a segment that slowly heats the samples while measuring sample fluorescence as the target DNA melts.

The melting temperature analysis provides a melting curve of sample fluorescence versus temperature. For example, the chart may show a downward curve in fluorescence for the samples as they melt. Several instruments are commercially available that are capable of performing real-time PCR and HRM analysis, for example, the ABI 7900 and 7900HT instruments.

Hybridization: The ability of complementary single-stranded DNA or RNA to form a duplex molecule (also referred to as a hybridization complex). Nucleic acid hybridization techniques can be used to form hybridization complexes between a primer (or probe) and a nucleic acid, such as a *C. psittaci* nucleic acid. For example, a primer (such as any of SEQ ID NOs: 3-8) having some homology to a *C. psittaci* nucleic acid molecule will form a hybridization complex with a *C. psittaci* nucleic acid molecule (such as any of SEQ ID NOs: 11-13). Hybridization occurs between a single stranded primer and a single stranded target nucleic acid (such as a *C. psittaci* nucleic acid), as illustrated in FIG. 1. When the target nucleic acid is initially one strand of a duplex nucleic acid the duplex must be melted (at least partially) for the primer to hybridize. This situation is also illustrated in FIG. 1.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (detects sequences that share at least 80% identity)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (detects sequences that share at least 50% identity)

Hybridization: 6×SSC at RT to 55° C. for 16-20 hours

Wash at least twice: 2×-3×SSC at RT to 55° C. for 20-30 minutes each.

The primers disclosed herein can hybridize to *C. psittaci* nucleic acids under low stringency, high stringency, and very high stringency conditions. Generally, the primers hybridize to a *C. psittaci* nucleic acid under very high stringency conditions.

Isolated: An "isolated" biological component (such as a nucleic acid) has been substantially separated or purified away from other biological components in which the component naturally occurs, such as other chromosomal and extra-chromosomal DNA, RNA, and proteins. Nucleic acids that have been "isolated" include nucleic acids purified by standard purification methods. The term also embraces nucleic acids prepared by recombinant expression in a host cell as well as chemically synthesized nucleic acids, such as probes and primers. Isolated does not require absolute purity, and can include nucleic acid molecules that are at least 50% isolated, such as at least 75%, 80%, 90%, 95%, 98%, 99% or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

LUX™ primers: FIG. 1 illustrates an oligonucleotide primer with a reporter fluorophore, such as 6-carboxyfluorescein (FAM) or 6-carboxy-4',5'-dichloro-2',7'-dimethoxyfluorescein (JOE) and a self quenching moiety. In one embodiment, the LUX™ primer includes a 3' reporter fluorophore, such as FAM or JOE and a 5' self quenching moiety, such as a hairpin structure. In the LUX™ primer, energy is released from the fluorophore in the form of light, upon extension of the primer during PCR. LUX™ fluorogenic primers are generally produced as a pair of two primers. The first primer is labeled with a fluorophore, i.e. FAM (6-carboxyfluorescin), and the second primer is unlabeled. Due to the specific conformation of the labeled primer (as a "hairpin" structure) prior to annealing to a target DNA sequence, interior fading of the fluorophore occurs (self-quenching). Annealing of the labeled primer to the target DNA sequence results in extension of the labeled primer and leads to an enhancement of fluorophore fluorescence during PCR.

LUX™ primers can be used in real-time quantitative PCR and RT-PCR to quantify 100 or fewer copies of a target sequence (or gene) in as little as 1 pg of template DNA or RNA. LUX™ primers have a broad dynamic range of 7-8 orders. For example, multiplex applications can be prepared using separate FAM and JOE-labeled primer sets to detect two different genes in the same sample. Typically, a custom-designed FAM-labeled primer set is used to detect the gene of interest, and a JOE-labeled Certified LUX™ primer set is used to detect a housekeeping gene as an internal control.

LUX™ primers are compatible with a wide variety of real-time PCR instruments, including but not limited to the ABI PRISM® 7700, 7000, and 7900 and GeneAmp® 5700; the Bio-Rad iCycler™; the Stratagene Mx4000™ and Mx3000™; the Cepheid SMART CYCLER®; the Corbett Research Rotor-Gene; and the Roche LIGHTCYCLER®.

Nucleic acid (molecule or sequence): A deoxyribonucleotide or ribonucleotide polymer including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can also include analogs of natural nucleotides, such as labeled nucleotides. In one example, a nucleic acid is a *C. psittaci* nucleic acid, which can include nucleic acids purified from *C. psittaci* bacterium as well as the amplification products of such nucleic acids. A nucleic acid molecule for detection includes probes or primers that are capable of hybridizing to the complementary sequence of a tagert nucleic acid molecule of interest.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. (herein incorporated by reference).

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine amongst others.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme which catalyzes the 5' to 3' elongation of a primer strand complementary to a nucleic acid template. Examples of polymerases that can be used to amplify a nucleic acid molecule include, but are not limited to the *E. coli* DNA polymerase I, specifically the Klenow fragment which has 3' to 5' exonuclease activity, Taq polymerase, reverse transcriptase (such as human immunodeficiency virus-1 reverse transcriptase (HIV-1 RT)), *E. coli* RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Probes and Primers: Nucleic acid molecules for detection. Nucleic acid probes and primers can be readily prepared based on the nucleic acid molecules provided in this invention, and therefore provide a substantial utility for the disclosed sequences. A probe comprises an isolated nucleic acid capable of hybridizing to a complementary sequence of a target nucleic acid (such as a portion of a *C. psittaci* nucleic acid), and a detectable label or reporter molecule can be attached to a probe. A primer comprises a short nucleic acid molecule, such as a DNA oligonucleotide, for example sequences of at least 15 nucleotides, which can be annealed to a complementary target nucleic acid molecule by nucleic acid hybridization to form a hybrid complex between the primer and the target nucleic acid strand. A primer can be extended along the target nucleic acid molecule by a polymerase enzyme such as a PCR technique. Therefore, primers can be used to amplify a target nucleic acid molecule (such as a portion of a *C. psittaci* nucleic acid), wherein the sequence of the primer is specific for the target nucleic acid molecule, for example so that the primer will hybridize to the target nucleic acid molecule under very high stringency hybridization conditions.

The specificity of a probe or primer increases with its length. Thus, for example, a primer that includes 30 consecutive nucleotides will anneal to a target sequence with a higher specificity than a corresponding primer of only 15 nucleotides. Thus, to obtain greater specificity, primers can be selected that include at least 15, 20, 22, 24, 26, 28, 30, 35, 40 or more consecutive nucleotides.

In particular examples, a probe or primer is at least 15 contiguous nucleotides complementary to a target nucleic acid molecule. Particular lengths of probes or primers that can be used to practice the methods of the present disclosure (for example, to amplify a region of a *C. psittaci* nucleic acid) include probes or primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40 or more contiguous nucleotides complementary to the target nucleic acid molecule (to be detected by hybridization or to be amplified), such as a primer of 15-30 nucleotides, 15-40 nucleotides.

A "set of primers" is a group of more than one primer and can be as few as a two primers, or a "primer pair." Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, ® 1991, Whitehead Institute for Biomedical Research, Cambridge, Mass.).

Methods for preparing and using probes and primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences.

In particular examples, a probe of primer (or primer pair) includes a detectable label. A detectable label or reporter molecule can be attached to a primer. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In one example, a probe or primer includes at least one fluorophore, such as an acceptor fluorophore or donor fluorophore. For example, a fluorophore can be attached at the 5'- or 3'-end of the primer. In specific examples, the fluorophore is attached to the base at the 5'-end of the primer, the base at its 3'-end, the phosphate group at its 5'-end or a modified base, such as a thymidine internal to the primer. In one example, a primer pair includes a single-labeled fluorogenic primer and a corresponding unlabeled primer, such as a D-LUX™ or LUX™ primer pair. In a further embodiment, the labeled primer includes a 5'-carboxyfluorescin (FAM) labeled primer and a self-quenching moiety, such as a hairpin structure.

Quantitating a nucleic acid molecule: Determining or measuring a quantity (such as a relative quantity) of nucleic acid molecules present, such as the number of amplicons or the number of nucleic acid molecules present in a sample. In particular examples, it is determining the relative amount or actual number of nucleic acid molecules present in a sample.

Quenching of fluorescence: A reduction of fluorescence. For example, quenching of a fluorophore's fluorescence occurs when a quencher molecule (such as the fluorescence quenchers listed above) is present in sufficient proximity to the fluorophore that it reduces the fluorescence signal (for example, prior to the binding of a primer to a *C. psittaci* nucleic acid sequence, when the primer contains a fluorophore and a self-quenching moiety).

Real-Time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as a *C. psittaci* nucleic acid) and/or quantitate the initial amounts of a target nucleic acid sequence. In some examples, real-time PCR is real-time reverse transcriptase PCR (rt RT-PCR).

In some examples, the amount of amplified target nucleic acid (such as a *C. psittaci* nucleic acid) is detected using a labeled probe, such as a probe labeled with a fluorophore, for example a TAQMAN® probe. In this example, the increase in fluorescence emission is measured in real-time, during the course of the real-time PCR. This increase in fluorescence emission is directly related to the increase in target nucleic acid amplification (such as *C. psittaci* nucleic acid amplification). In some examples, the change in fluorescence (dRn) is calculated using the equation $dRn=Rn^{+}-Rn^{-}$, with $Rn^{+}$ being the fluorescence emission of the product at each time point and $Rn^{-}$ being the fluorescence emission of the baseline. The dRn values are plotted against cycle number, resulting in amplification plots for each sample In another example, the amount and identification of an amplified target nucleic acid (such as a *C. psittaci* nucleic acid) is detected using a labeled primer, such as a primer labeled with a fluorophore, for example a LUX™ primer (Invitrogen, CA). In this example, an increase in fluorescence emission is observed and measured upon exposure of the sample to real-time PCR conditions as the labeled primer transitions from a single stranded conformation to a double stranded product/primer duplex. An increase in fluorescence emission is directly related to hybridization of the labeled primer to the target nucleic acid amplification product (such as *C. psittaci* nucleic acid amplification products) and the characteristics of the amplification product, for example, G/C content, and sequence length. Conversely, a decrease in fluorescence emission of the amplified nucleic acids upon incremental temperature increases as part of a melt curve analysis is the result of the labeled primer separating from the amplification product, and transitioning back to a single-stranded conformation, where minimal fluorescence is observed as a result of self-quenching of the fluorophore moiety. With reference to FIGS. 3A-3C and 5A-5B, the threshold value is the PCR cycle number at which the fluorescence emission (dRn) exceeds a chosen threshold ($Rn^-$), which is typically 10 times the standard deviation of the baseline (this threshold level can, however, be changed if desired).

Sample: A sample, such as a biological sample, is a sample obtained from an animal subject. As used herein, biological samples include all clinical samples useful for detection of *C. psittaci* infection in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; bronchoalveolar levage; tracheal aspirates; sputum; nasopharyngeal aspirates; pharyngeal swabs, oropharyngeal aspirates; and saliva. In particular embodiments, the biological sample is obtained from an animal subject, such as in the form of tracheal aspirates, sputum, nasopharyngeal aspirates, pharyngeal swabs, oropharyngeal aspirates, and saliva.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N8O5, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 15 consecutive nucleotides from an identified sequence as follows contains a region that shares 75 percent sequence identity to that identified sequence (i.e., 15÷20*100=75).

```
                          1                  20
Target Sequence:          atggtggacccggtgggctt   (SEQ ID NO: 1)
                          | || ||| |||| |||| |
Identified Sequence:      acgggggatccggcgggcct   (SEQ ID NO: 2)
```

One indication that two nucleic acid molecules are closely related is that the two molecules hybridize to each other under stringent conditions. Stringent conditions are sequence-dependent and are different under different environmental parameters.

The primers disclosed herein are not limited to the exact sequences shown, as those skilled in the art will appreciate that changes can be made to a sequence, and not substantially affect the ability of the primer to function as desired. For example, sequences having at least 80%, at least 90%, at least 95%, at least 96%, at least 97%, at least 98%, or at least 99% sequence identity to any of SEQ ID NOS:3-8 and SEQ ID NOS:16-17 are provided herein. One of skill in the art will appreciate that these sequence identity ranges are provided for guidance only; it is possible that primers can be used that fall outside these ranges.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA such as viral RNA), the amplification of which is intended. Purification or isolation of the target nucleic acid molecule, if needed, can be conducted by methods known to those in the art, such as by using a commercially available purification kit or the like. In one example, a target nucleic molecule is a chlamydophila nucleic acid sequence. In another example, the chlamydophila nucleic sequence is a *C. psittaci, C. caviae* or *C. abortus* nucleic acid. In several examples, a target nucleic molecule is a *C. psittaci* nucleic acid sequence.

III. Overview Of Several Embodiments

Outbreaks of psittacosis in poultry farms and zoonotic infections in workers who are in close proximity with infected birds raise public health concerns. Additionally, the importation of companion birds infected with virulent bacterial infections poses an increased risk of infection for individuals involved with the sale, transportation and ownership of these animals. Methods are needed to readily detect and identify *C. psittaci*, for example to rapidly diagnose or determine the potential of bacteria samples, such as those obtained from a subject infected or believed to be infected with *C. psittaci*. Additionally, it would be particularly advantageous to be able to detect and discriminate between *Chlamydophila* species.

Disclosed herein are methods for the universal detection of *C. psittaci* as well as for the identification of *C. psittaci* genotypes. Furthermore, the methods allow for the discrimination between closely related *Chlamydophila* species such as *C. abortus* and *C. caviae*. The methods have been developed in one embodiment with a unique set of nucleic acid primers that are surprisingly effective at detecting and discriminating between *Chlamydophila* species. In another embodiment, the nucleic acid primers are surprisingly effective at detecting and discriminating between genotypes of *C. psittaci*. This ability to rapidly screen and identify a *Chlamydophila* species or *C. psittaci* genotype provides a significant public health advantage.

In particular examples, the methods for the detection and identification of *Chlamydophila* involve direct dection of a hybridized primer or probe, such as by Southern blot or dot blot analysis. In other examples, hybridized primers or probes are further used to direct amplification of a target *Chlamydophila* nucleic acid, which is then detected using a label such as a self-quenching fluororophore.

As disclosed herein, using sequence alignments of *Chlamydophila* and *C. psittaci* sequences, previously unknown regions of high sequencing homology were discovered amongst individual *Chlamydophila* species and strains. These regions were used to create the primers shown in Table 1. Using these highly homologous regions as a starting point the disclosed primers were designed such that they were surprisingly effective at recognizing genetically similar isolates within *Chlamydophila* and within *C. psittaci* genotypes. In an effort to reduce false positive reactions amongst *Chlamydophila* species, sets of primers were designed that allowed for the specific amplification of *C. psittaci* nucleic acids. In a further development, primer sets were designed that allowed for the specific amplification of an individual *C. psittaci* genotype. Additionally, elimination of false positive reactions among similar genetic strains of *Chlamydophila* was achieved using primer sets that allowed for the specific amplification of *C. caviae* nucleic acids. The latter primer set was surprisingly effective at recognizing and identifying *C. caviae* nucleic acids in a sample.

Primers and Probes

Primers and probes that can hybridize to and direct the amplification of *Chlamydophila* target nucleic acids are disclosed. The primers and probes disclosed herein are between 15 to 40 nucleotides in length, such as 15, 16, 17, 18, 19, 20, 21, 22, 23, 24, 25, 26, 27, 28, 29, 30, 31, 32, 33, 34, 35, 36, 37, 38, 39, or even 40 nucleotides in length. In several embodiments, the primer or probe is capable of hybridizing under very high stringency conditions to a complementary sequence of a *Chlamydophila* nucleic acid sequence set forth as SEQ ID NO: 11, SEQ ID NO: 12, SEQ ID NO: 13, SEQ ID NO: 14, or SEQ ID NO: 15, and directing the amplification of the *Chlamydophila* nucleic acid. In some embodiments, the primer or probe is capable of hybridizing under very high stringency conditions to the complementary sequence of a *C. psittaci* nucleic acid sequence set forth as SEQ ID NO: 11, SEQ ID NO: 12, or SEQ ID NO: 13, and directing the amplification of the *C. psittaci* nucleic acid. In another embodiment, the primer is capable of hybridizing under very high stringency conditions to the complementary sequence of a *C. caviae* nucleic acid sequence set forth as SEQ ID NO: 14 and directing the amplification of the *C. caviae* nucleic acid. In yet another embodiment, the primer is capable of hybridizing under very high stringency conditions to the complementary sequence of a *C. abortus* nucleic acid sequence set forth as SEQ ID NO: 15 and directing the amplification of the *C. abortus* nucleic acid.

In several embodiments, the primer or probe capable of hybridizing to and directing the amplification of a *C. psittaci* nucleic acid is 15 to 40 nucleotides in length and includes a nucleic acid sequence that is at least 95% identical such as at least 96%, at least 97%, at least 98%, at least 99%, or even 100% identical to the nucleic acid sequence set forth as SEQ ID NO: 3, SEQ ID NO: 4, SEQ ID NO: 5, SEQ ID NO: 6, SEQ ID NO: 7, or SEQ ID NO: 8. In several embodiments, the primer capable of hybridizing to and directing the amplification of a *C. psittaci* nucleic acid consists essentially of, or consists of a nucleic acid sequence set forth as SEQ ID NO: 3, SEQ ID NO: 4, SEQ ID NO: 5, SEQ ID NO: 6, SEQ ID NO: 7, or SEQ ID NO: 8.

In one embodiment, the primer is capable of hybridizing under very high stringency conditions to and directing the amplification of a *C. caviae* nucleic acid contains a nucleic acid sequence that is at least 95% identical such as at least 96%, at least 97%, at least 98%, at least 99%, or even 100% identical to the nucleic acid sequence set forth as SEQ ID NO: 16, or SEQ ID NO: 17. In another embodiment, the primer capable of hybridizing to and directing the amplification of a *C. caviae* nucleic acid consists essentially of, or consists of a nucleic acid sequence set forth as SEQ ID NO: 16, or SEQ ID NO: 17.

In several embodiments, the primer is a *C. psittaci* genotype-specific primer. In one example, a *C. psittaci* genotype-specific primer is capable of hybridizing under stringent conditions (such as high stringency, or very high stringency conditions) to a complementary *C. psittaci* nucleic acid from a specific genotype, such as *C. psittaci* genotype A, B, C, D, E or F. In one embodiment, a primer that is *C. psittaci* genotype-specific for *C. psittaci* genotype F is not specific for the amplification and hybridization of any other *C. psittaci* genotype. Likewise, a primer that is genotype-specific for the amplification and hybridization of *C. psittaci* genotype A is not specific for the amplification and hybridization of *C. psittaci* genotype F. In other words, in the above two instances, a nucleic acid primer that specifically hybridizes to a *C. psittaci* genotype F nucleic acid (such as a nucleic acid that is at least a portion of the ompA gene from *C. psittaci*, for example the nucleic acid sequence set forth as SEQ ID NOs: 11-13) does not amplify and hybridize to nucleic acids of another *C. psittaci* genotype. Conversely, a nucleic acid primer that specifically hybridizes to *C. psittaci* genotype E and/or B nucleic acids does not specifically hybridize to *C. psittaci* genotype F nucleic acids; such nucleic acids would be genotype-specific primers for *C. psittaci* genotypes B and/or E. Thus, in some embodiments, genotype-specific primers can be used to specifically amplify a nucleic acid from *C. psittaci* genotype F or from *C. psittaci* genotypes E/B, but not both.

In some embodiments, the primer is capable of hybridizing under very high stringency conditions to a complementary nucleic acid from *Chlamydophila*, for example the amplification and hybridization of a *C. caviae* nucleic acid from the ompA gene of *C. caviae* set forth as SEQ ID NO: 14. In yet another embodiment, the primer is capable of hybridizing under very high stringency conditions to a complentary nucleic acid from *Chlamydophila*, for example the amplification and hybridization of a *C. abortus* nucleic acid from the ompA gene of *C. abortus* set forth as SEQ ID NO: 15.

In several embodiments, the primer is capable of hybridizing and amplifying under very high stringency conditions to one or more *C. psittaci* genotypes. In one example, a *C. psittaci* specific primer is capable of hybridizing under stringent conditions (such as high stringency, or very high stringency conditions) to the complementary sequence of any *C. psittaci* nucleic acid, for example, genotypes A, B, C, D, E, F or E/B. For example, a primer specific for the amplification and hybridization of *C. psittaci* can detect any *C. psittaci* genotype and is not limited to the detection of a single *C. psittaci* genotype. In other words, a nucleic acid primer that specifically hybridizes to a complementary sequence of a *C. psittaci* nucleic acid (such as a nucleic acid that is at least a portion of the ompA gene from *C. psittaci* such as SEQ ID NOs: 11-13) does not hybridize to a *C. caviae* or *C. abortus* nucleic acid; such primers would be specific for the detection of *C. psittaci*.

In some embodiments, the primer is capable of distinguishing between *C. psittaci* genotypes. In some embodiments, the primer specific for the hybridization and amplification of a *C. psittaci* nucleic acid includes a nucleic acid sequence at least 95% identical such as at least 96%, at least 97%, at least 98%, at least 99%, or even 100% identical to SEQ ID NO:3 or SEQ ID NO: 4. In a specific example, the primer that discriminates between *C. psittaci* genotypes contains a nucleic acid sequence at least 95% identical such as at least 96%, at least 97%, at least 98%, at least 99%, or even 100% identical to SEQ ID NO: 5 or SEQ ID NO: 6. In another embodiment, a primer capable of hybridizing under very high stringency conditions to *C. psittaci* genotype F includes a nucleic acid sequence at least 95% identical such as at least 96%, at least 97%, at least 98%, at least 99%, or even 100% identical to SEQ ID NO: 7 or SEQ ID NO: 8.

In some embodiments, the primer is specific for the amplification of *C. psittaci* genotypes A, B, C, D or E, such as the nucleic acid sequence set forth as SEQ ID NO: 5 or SEQ ID NO: 6. In a specific example, a primer specific for *C. psittaci* genotypes A, B, C, D or E includes a nucleic acid sequence at least 95% identical such as at least 96%, at least 97%, at least 98%, at least 99%, or even 100% identical to SEQ ID NO:5 or SEQ ID NO: 6. In another embodiment, a primer specific for *C. psittaci* genotypes A, B, C, D or E consists essentially of, or consists of a nucleic acid set forth as SEQ ID NO:5 or SEQ ID NO: 6. In some examples, the primer is specific for the amplification of *C. psittaci* genotype F, such as the nucleic acid sequence set forth as SEQ ID NO: 7 or SEQ ID NO: 8. In a specific example, a primer specific for the amplification of *C. psittaci* genotype F includes a nucleic acid sequence at least 95% identical such as at least 96%, at least 97%, at least 98%, at least 99%, or even 100% identical to SEQ ID NO: 7 or SEQ ID NO: 8. In another embodiment, a primer specific for *C. psittaci* genotype F consists essentially of a nucleic acid set forth as SEQ ID NO: 7 or SEQ ID NO: 8.

In certain embodiments the primers are a set of primers, such as a pair of primers, capable of hybridizing to and amplifying a *Chlamydophila* nucleic acid. Such a set of primers includes at least one forward primer and at least one reverse primer, where the primers are specific for the amplification of a *Chlamydophila* nucleic acid in a sample. In some examples, the set of primers includes a pair of primers that is specific for the amplification of *C. psittaci, C. caviae* or *C. abortus.*

In certain examples, the pair of primers is specific for the amplification of a *C. psittaci* nucleic acid and includes a forward primer at least 95% identical such as at least 96%, at least 97%, at least 98%, at least 99%, or even 100% identical to SEQ ID NO: 5 and a reverse primer at least 95% identical such as at least 96%, at least 97%, at least 98%, at least 99%, or even 100% identical to SEQ ID NO: 6. In another example, the pair of primers specific for the amplification of a *C. caviae* nucleic acid includes a forward primer at least 95% identical such as at least 96%, at least 97%, at least 98%, at least 99%, or even 100% identical to SEQ ID NO: 17 and a reverse primer at least 95% identical such as at least 96%, at least 97%, at least 98%, at least 99%, or even 100% identical to SEQ ID NO: 16.

In another example, a set of primers specific for the amplification of a *C. psittaci* nucleic acid includes one or more forward primers 15 to 40 nucleotides in length including a nucleic acid sequence at least 95% identical such as at least 96%, at least 97%, at least 98%, at least 99%, or even 100% identical to SEQ ID NO: 3, SEQ ID NO: 5, or SEQ ID NO: 7; and one or more reverse primers 15 to 40 nucleotides in length including a nucleic acid sequence at least 95% identical such as at least 96%, at least 97%, at least 98%, at least 99%, or even 100% identical to SEQ ID NO: 4, SEQ ID NO: 6, or SEQ ID NO: 8. In one example, the pair of primers is specific for the amplification of nucleic acids from at least one *C. psittaci* genotype. In another example, the set of primers is specific for the amplification of nucleic acids from at least one *C. psittaci* genotype selected from A, B, C, D, E or F. In a further embodiment, the set of primers is specific for the amplification of *C. psittaci* genotypes A, B, C, and E. In yet another embodiment, the set of primers is specific for the amplification of *C. psittaci* genotype F nucleic acids.

In yet another example, a set of primers specific for the amplification of a *C. caviae* nucleic acid includes one or more forward primers 15 to 40 nucleotides in length including a nucleic acid sequence at least 95% identical such as at least 96%, at least 97%, at least 98%, at least 99%, or even 100% identical to SEQ ID NO: 17 and one or more reverse primers 15 to 40 nucleotides in length including a nucleic acid sequence at least 95% identical such as at least 96%, at least 97%, at least 98%, at least 99%, or even 100% identical to SEQ ID NO: 16.

Although exemplary primers are provided in SEQ ID NOs: 3-10, one skilled in the art will appreciate that the primer sequence can be varied slightly by moving the primers a few nucleotides upstream or downstream from the nucleotide positions that they hybridize to on the *C. psittaci* nucleic acid, provided that the primer is still specific for the *C. psittaci* sequence, meaning that the primer retains species- or strain-specificity for *C. psittaci*. For example, the primer is specific for the hybridization to a complementary sequence of a *C. psittaci* nucleic acid set forth as SEQ ID NO: 11, SEQ ID NO: 12, or SEQ ID NO: 13. In another example, one of skill in the art will appreciate that by analyzing the consensus sequences shown in FIGS. 4A and 4B that variations of the primers disclosed as SEQ ID NOs: 3-8 can be made by "sliding" the primers a few nucleotides 5' or 3' from their positions, and that such variation will still be specific for *C. psittaci*. Thus, in some examples, the primer sequence is 2-5 nucleotides 5' of SEQ ID NOs: 3-8 and/or 2-5 nucleotides 3' if SEQ ID NOs: 3-8 using the sequences presented in FIGS. 4A and 4B. Thus, the primers can be 2, 3, 4 or 5 nucleotides 5' of SEQ ID NOs: 3-8 and/or 2, 3, 4 or 5 nucleotides 3' if SEQ ID NOs: 3-8.

Also provided by the present application are primers that include variations to the nucleotide sequences shown in any of SEQ ID NOs: 3-8, as long as such variations permit detection of the *C. psittaci* nucleic acid, such as a *C. psittaci* genotype. For example, a primer can have at least 95% sequence identity such as at least 96%, at least 97%, at least 98%, at least 99% to a nucleic acid containing the sequence shown in any of SEQ ID NOs: 3-8. In such examples, the number of nucleotides does not necessarily change, but the nucleic acid sequence shown in any of SEQ ID NOs: 3-8 can vary at a few nucleotides, such as changes at 1, 2, 3, or 4 nucleotides, for example by changing the nucleotides as shown in the primer binding location of FIGS. 4A and 4B.

The present application also provides primers that are slightly longer or shorter than the nucleotide sequences shown in any of SEQ ID NOs: 3-8, as long as such deletions or additions permit detection of the desired *C. psittaci* nucleic acid, such as specific *C. psittaci* genotypes. For example, a primer can include a few nucleotide deletions or additions at the 5'- or 3'-end of the primer shown in any of SEQ ID NOs: 3-8, such as addition or deletion of 1, 2, 3, or 4 nucleotides from the 5'- or 3'-end, or combinations thereof (such as a deletion from one end and an addition to the other end). In such examples, the number of nucleotides changes. One of skill in the art will appreciate that the consensus sequences shown in FIGS. 4A and 4B provide sufficient guidance as to what additions and/or subtractions can be made, while still maintaining specificity for the detection of *C. psittaci* and/or *C. psittaci* genotype nucleic acids.

In several embodiments, the primer is detectably labeled, either with an isotopic or non-isotopic label, alternatively the target nucleic acid (such as a *C. psittaci* nucleic acid) is labeled. Non-isotopic labels can, for instance, comprise a fluorescent or luminescent molecule, biotin, an enzyme or enzyme substrate or a chemical. Such labels are preferentially chosen such that the hybridization of the primer with target nucleic acid (such as a *C. psittaci* nucleic acid) can be detected. In some examples, the primer is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the primer includes both a donor fluorophore and an accepter fluorophore. In other examples, the primer includes a fluorophore and a self quenching moiety. In one example, the primer includes a fluorophore on a modified nucleotide (such as a T within the primer), and the labeled primer further includes a self-quenching moiety, such as a hairpin structure. Appropriate donor/acceptor fluorophore pairs can be selected using routine methods. In one example, the donor emission wavelength is one that can significantly excite the acceptor, thereby generating a detectable emission from the acceptor.

In particular examples, the self quenching moiety (a fluorescence quencher) is attached to the 5' end of the primer and the donor fluorophore is attached to a 3' end of the primer. In another particular example, the self quenching moiety (such as a fluorescence quencher) is attached to the 3' end of the primer and the donor fluorophore is attached to the 5' end of the primer.

Detection and Identification of *Chlamydophila* and *Chlamydophila psittaci*

The *Chlamydophila* and *C. psittaci* specific primers disclosed herein can be used for the detection, identification and genotyping of *Chlamydophila* and *C. psittaci* in a sample, such as a biological sample obtained from a subject that has or is suspected of having a *Chlamydophila* and/or *C. psittaci* infection. Thus, the disclosed methods can be used to diagnose if a subject has a *Chlamydophila* and/or a *C. psittaci* infection and/or discriminate between the bacterial species and/or strain the subject is infected with. An example of the methods of identifying *Chlamydophila* species is shown in FIG. 6A.

In particular examples, the methods for the detection and identification of *Chlamydophila* involve direct dection of a hybridized primer or probe, such as by Southern blot or dot blot analysis. In other examples, hybridized primers or probes are further used to direct amplification of a target *Chlamydophila* nucleic acid, which is then detected using a label such as a self-quenching fluororophore. In particular examples, amplification is carried out usings pairs of the particular primers disclosed herein. In other examples, amplification is carried our using a specific forward or reverse primer disclosed herein, in combination with a universal reverse or forward primer (respectively). Any universal primer known to the art that will hybridize to a common repeat sequence and direct the amplification of DNA will be suitable for the methods described herein. In particular examples, the nucleic acid sample for the subject is pretreated to add a repeat nucleotide sequence that can serve as a target sequence for a universal amplification primer.

In one embodiment, a method for diagnosing a *Chlamydophila psittaci* infection in a subject suspected of having a *C. psittaci* infection includes obtaining a nucleic acid sample from the subject and contacting the sample with one or more of the probes or primers specific for *C. psittaci* as disclosed herein (such as SEQ ID NOs: 3-8), and detecting hybridization or amplification of the one or more *C. psittaci* specific primers in the sample. Detection of hybridization or amplification indicates that the subject is infected with *C. psittaci*. The amplified nucleic acid can be detected by a detectable label, such as a fluorescent moiety conjugated to one the amplification primers. In another embodiment, the method further includes discriminating and/or distinguishing between a *C. psittaci* infection and a *C. caviae* infection by contacting the sample suspected of having a *C. psittaci* or *C. caviae* infection with one or more primers set forth as SEQ ID NO: 16 or SEQ ID NO: 17, and detecting hybridization to or amplification of the sample. Detection of hybridization or amplification indicates that the subject is infected with *C. caviae*. In yet another embodiment, the method further includes discriminating and/or distinguishing between a *C. psittaci* infection and a *C. abortus* infection by contacting the sample suspected of having a *C. psittaci* or *C. abortus* infection with one or more primers set forth as SEQ ID NO: 5 or SEQ ID NO: 6, and detecting hybridization to or amplification of the sample. Detection of hybridization or amplification indicates that the subject is infected with *C. psittaci*. The absence of hybridization or amplification indicates that the subject is infected with *C. abortus*.

Methods for the detection of *Chlamydophila* nucleic acids are disclosed, for example to determine if a subject is infected with *Chlamydophila* bacteria. Methods also are provided for determining the species and/or genotype of the *Chlamydophila* nucleic acid, for example to determine which species and/or genotype of *Chlamydophila* bacteria a subject is infected with.

The methods described herein may be used for any purpose for which detection of *Chlamydophila* or *C. psittaci* is desirable, including diagnostic and prognostic applications, such as in laboratory and clinical settings. Appropriate samples include any conventional environmental or biological samples, including clinical samples obtained from a human or veterinary subject, such as a bird or mammal. Suitable samples include all biological samples useful for detection of bacterial infection in subjects, including, but not limited to, cells, tissues (for example, lung, liver and kidney), bone marrow aspirates, bodily fluids (for example, blood, serum, urine, cerebrospinal fluid, bronchoalveolar levage, tracheal aspirates, sputum, nasopharyngeal aspirates, oropharyngeal aspirates, saliva), eye swabs, cervical swabs, vaginal swabs, rectal swabs, stool, and stool suspensions. Particularly suitable samples include samples obtained from bronchoalveolar levage, tracheal aspirates, sputum, nasopharyngeal aspirates, oropharyngeal aspirates, or saliva. Standard techniques for acquisition of such samples are available. See for example, Schluger et al., *J. Exp. Med.* 176:1327-1333, 1992; Bigby et al., *Am. Rev. Respir. Dis.* 133:515-518, 1986; Kovacs et al., *NEJM* 318:589-593, 1988; and Ognibene et al., *Am. Rev. Respir. Dis.* 129:929-932, 1984.

In some embodiments, detecting a *Chlamydophila* nucleic acid in a sample involves contacting the sample with at least one of the *Chlamydophila* specific primers or probes disclosed herein that is capable of hybridizing to a complementary *Chlamydophila* nucleic acid under conditions of very high stringency (such as a nucleic acid primer or probe capable of hybridizing under very high stringency conditions to a complementary sequence of a *Chlamydophila* nucleic acid sequence set forth as SEQ ID NOs: 11-15; for example a primer or probe with a nucleic acid sequence at least 95% identical, such as at least 96%, at least 97%, at least 98%, at least 99%, or even 100% identical to the nucleotide sequence set forth as one of SEQ ID NO: 3, SEQ ID NO: 4, SEQ ID NO: 5, SEQ ID NO: 6, SEQ ID NO: 7, SEQ ID NO: 8, SEQ ID NO: 16, and SEQ ID NO: 17), and detecting hybridization between the sample and the primer or probe. Detection of hybridization between the primer or probe and the sample indicates the presence of a *Chlamydophila* nucleic acid in the sample.

By using *Chlamydophila* species-specific primers or probes, the disclosed methods can be used to detect the presence of *Chlamydophila* species in a sample. For example, by contacting the sample with a *C. psittaci* species-specific primer or probe as disclosed herein, such as a primer or probe capable of hybridizing under very high stringency conditions to a complementary sequence of a *C. psittaci* nucleic acid sequence set forth as SEQ ID NOs: 11-13; for example, a primer with a nucleic acid sequence of at least 95% identical to SEQ ID NO: 5 or SEQ ID NO: 6. Detection of hybridization of the *C. psittaci* species-specific primer or probe to the sample indicates the presence of *C. psittaci* nucleic acids in the sample.

In another embodiment, *Chlamydophila* species-specific primers can be used to discriminate between species of *Chlamydophila* in a sample. For example, by contacting the sample with the *Chlamydophila* species-specific primer or probe as disclosed herein, such as a primer or probe capable of hybridizing under very high stringency conditions to a complementary sequence of a *C. psittaci* nucleic acid, a *C. abortus* nucleic acid, or a *C. caviae* nucleic acid; for example, a primer with a nucleic acid sequence of at least 95% identical to SEQ ID NO: 5, SEQ ID NO: 6 (primers specific for *C. psittaci* and *C. caviae* but not *C. abortus*) or SEQ ID NO: 16, SEQ ID NO: 17 (primers specific for *C. caviae*). Detection of hybridization of the *Chlamydophila* species-specific primers (SEQ ID NO: 5 or SEQ ID NO: 6) to the sample indicates the presence of *Chlamydophila* nucleic acids in the sample. Furthermore, hybridization between primers SEQ ID NO: 16 or SEQ ID NO: 17 is indicative of the presence of *C. caviae* in the sample. Alternatively, the absence of hybridization in the sample with either of the above primer sets (SEQ ID NO: 5/SEQ ID NO: 6 or SEQ ID NO: 16/SEQ ID NO: 17) is indicative of the absence of *C. psittaci* and *C. caviae* in the sample. However, detection of hybridization or amplification of SEQ ID NOs: 3 or 4 but not SEQ ID NOs: 5 and 6 is indicative of a *C. abortus* infection.

Additionally, the primers or probes disclosed herein can be used to detect the presence of and discriminate between genotypes of *C. psittaci*. For example, contacting a sample with a primer or probe specific for *C. psittaci* genotype F nucleic acids, such as a primer or probe capable of hybridizing under very high stringency conditions to a complementary sequence of a *C. psittaci* genotype F nucleic acid such as the sequence set forth as SEQ ID NOs: 11-13, for example a primer or probe with a nucleic acid sequence of at least 95% identical to SEQ ID NO: 7 or SEQ ID NO: 8 can be used to detect *C. psittaci* genotype F nucleic acids in the sample. Detection of hybridization between the *C. psittaci* genotype F-specific primer or probe and the sample indicates the presence of *C. psittaci* genotype F nucleic acids in the sample. Thus, the disclosed methods can be used discriminate between genotypes of *C. psittaci* in a sample.

In another example, a primer specific for *C. psittaci* genotype A, B, C, D or E, such as a primer or probe capable of hybridizing under very high stringency conditions to a complementary sequence of a *C. psittaci* nucleic acid sequence set forth as SEQ ID NOs: 11-13, for example a nucleic acid set forth as SEQ ID NO: 5 or SEQ ID NO: 6, may be used to detect hybridization between the primer or probe and a sample suspected to contain *C. psittaci*. Detection of hybridization is indicative that at least one genotype from *C. psittaci* genotype A, B, C, D, E, or F is present in the sample. In one embodiment, the primer or probe includes a nucleic acid sequence at least 95% identical, such as at least 96%, at least 97%, at least 98%, at least 99%, or even 100% identical to the nucleotide sequence set forth as SEQ ID NO: 5 or SEQ ID NO: 6.

In yet another example, contacting a sample with a primer or probe specific for *C. psittaci* genotype F, such as a primer or probe capable of hybridizing under very high stringency conditions to a complementary sequence of a *C. psittaci* nucleic acid sequence set forth as SEQ ID NOs: 11-13, for example a nucleic acid set forth as SEQ ID NO: 7 or SEQ ID NO: 8, and detecting the hybridization between the primer or probe and the *C. psittaci* nucleic acid indicates the presence of *C. psittaci* genotype F. In one embodiment, the primer or probe includes a nucleic acid sequence at least 95% identical, such as at least 96%, at least 97%, at least 98%, at least 99%, or even 100% identical to the nucleotide sequence set forth as SEQ ID NO: 7 or SEQ ID NO: 8. In a further embodiment, the primer or probe consists essentially of the nucleotide sequence set forth as SEQ ID NO: 7 or SEQ ID NO: 8.

In one example, contacting a sample with a primer or probe specific for *C. caviae*, such as a primer capable of hybridizing under very high stringency conditions to a complementary sequence of a *C. caviae* nucleic acid sequence set forth as SEQ ID NO: 14, for example a nucleic acid set forth as SEQ ID NO: 16 or SEQ ID NO: 17, and detecting the hybridization between the primer and the sample suspected of containing a *C. caviae* nucleic acid indicates the presence of *C. caviae*. In one embodiment, the primer or probe specific for *C. caviae* includes a nucleic acid sequence at least 95% identical to the nucleotide sequence set forth as SEQ ID NO: 16 or SEQ ID NO: 17. In another embodiment, the primer or probe specific for *C. caviae* consists essentially of the nucleotide sequence set forth as SEQ ID NO: 16 or SEQ ID NO: 17.

In yet another example (and as shown in FIG. 6A), a primer or probe specific for the detection of *C. abortus* or *C. psittaci* can be used to distinguish between these two *Chlamydophila* species in a biological sample. In this example, a primer or probe capable of hybridizing under very high stringency conditions, for example a nucleic acid set forth as SEQ ID NO: 3 or SEQ ID NO: 4, is used to detect hybridization between the primer or probe and the sample suspected of containing a *Chlamydophila* nucleic acid. Detection of hybridization and amplification of the sample by the primers or probes set forth as SEQ ID NO: 3 or SEQ ID NO: 4 suggests the presence of *C. psittaci, C. abortus*, or *C. caviae* in the sample. In this example, the presence of *C. abortus* is confirmed by detecting a lack of hybridization and amplification using the primers set forth as SEQ ID NO: 5 or SEQ ID NO: 6 and the sample. A failure to detect hybridization or amplification is indicative of the presence of *C. abortus* in the sample. In contrast, detection of amplification using SEQ ID NO: 5 or SEQ ID NO: 6 in the above example is indicative of the presence of *C. psittaci*. Additional *C. psittaci* strain-specific primers may be used to determine the genotype of *C. psittaci* as already described. Following amplication with SEQ ID NO: 3 or SEQ ID NO: 4 or SEQ ID NO: 5 or SEQ ID NO: 6, HRM analysis can then be performed to distinguish between the presence of *C. psittaci* and *C. caviae* in the sample In some embodiments, detecting the presence of a *Chlamydophila* or a *C. psittaci* nucleic acid sequence in a sample includes the extraction of *Chlamydophila* and/or *C. psittaci* RNA. RNA extraction relates to releasing RNA from a latent or inaccessible form in an environment such as a virion, cell or sample and allowing the RNA to become freely available. In such a state, it is suitable for effective detection and/or amplification of the *Chlamydophila* and/or *C. psittaci* nucleic acid. Releasing RNA may include steps that achieve the disruption of bacterial cells containing RNA. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular or viral components, wherein such components may be either particulate or dissolved.

One of ordinary skill in the art will know suitable methods for extracting RNA from a sample; such methods will depend upon, for example, the type of sample in which the *Chlamydophila* and *C. psittaci* RNA is found. For example, the RNA may be extracted using guanidinium isothiocyanate, such as the single-step isolation by acid guanidinium isothiocyanate-phenol-chloroform extraction of Chomczynski et al., *Anal. Biochem.* 162:156-59, 1987. The sample can be used directly or can be processed, such as by adding solvents, preservatives, buffers, or other compounds or substances. Bacterial RNA can be extracted using standard methods. For instance, rapid RNA preparation can be performed using a commercially available kit (such as the SIGMA-ALDRICH® GenElute Bacterial Total RNA Purification Kit, All-In-One Purification Kit (NORGEN BIOTEC CORPORATION), TRIzol® MAX™ Bacterial RNA Isolation Kit (Invitrogen™), MESSEGEAMP™ II-Bacteria RNA Amplification Kit (AMBION®) or RNEASY® Protect Bacteria Mini Kit (QIAGEN). Alternatively, *Chlamydophila* bacteria may be disrupted by a suitable detergent in the presence of proteases and/or inhibitors of ribonuclease activity.

In some embodiments, the primer is detectably labeled, either with an isotopic or non-isotopic label; in alternative embodiments, the *Chlamydophila* nucleic acid is labeled. Non-isotopic labels can, for instance, comprise a fluorescent or luminescent molecule, or an enzyme, co-factor, enzyme substrate, or hapten. The primer is incubated with a single-stranded or double-stranded preparation of RNA, DNA, or a mixture of both, and hybridization determined. In some examples, hybridization results in a detectable change in signal such as in increase or decrease in signal, for example from the labeled primer. Thus, detecting hybridization includes detecting a change in signal from the labeled primer during hybridization relative to signal from the labeled primer before hybridization. In another embodiment, detecting hybridization includes detecting a change in signal from the labeled primer after hybridization relative to signal from the labeled primer before hybridization. In some examples, detecting hybridization further includes performing high-resolution melt analysis of an amplified product in a sample and determining the signal from the labeled primer relative to signal from the labeled primer before amplification. In other instances, detecting hybridization includes performing high-resolution melt analysis of an amplified product in a sample and determining a change in signal from the labeled primer during the high-resolution melt analysis. As already discussed, a change in conformation of the labeled primer (such as a LUX™ primer) from single-stranded conformation to double-stranded conformation, for example, as a result of amplification will result in an increase of fluorescence. Conversely, a shift in conformation of the labeled primer (such as a LUX™ primer) from double-stranded to single-stranded conformation or a hairpin structure will result in a significant decrease in fluorescence, and will therefore be detected as a decrease in signal. One of ordinary skill in the art will appreciate that other means for detecting hybridization are commercially available and are readily applicable to the proposed methods. While the method for detecting hybridization is not critically important, the ability to detect a change in signal relative to the initial starting material (e.g., labeled primer alone) is necessary.

In some embodiments, *Chlamydophila* nucleic acids present in a sample are amplified prior to using a hybridization primer or probe for detection. For instance, it can be advantageous to amplify a portion of the *Chlamydophila* or *C. psittaci* nucleic acid, then detect the presence of the amplified *Chlamydophila* or *C. psittaci* nucleic acid. For example, to increase the number of nucleic acids that can be detected, thereby increasing the signal obtained. *Chlamydophila* or *C. psittaci* specific nucleic acid primers can be used to amplify a region that is at least about 50, at least about 60, at least about 70, at least about 80, at least about 90, at least about 100, at least about 200, or more base pairs in length to produce amplified *Chlamydophila* or *C. psittaci* nucleic acids. Any nucleic acid amplification method can be used to detect the presence of *Chlamydophila* or *C. psittaci* in a sample. In one specific, non-limiting example, polymerase chain reaction (PCR) is used to amplify the *Chlamydophila* or *C. psittaci* nucleic acid sequences. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the *Chlamydophila* or *C. psittaci* nucleic acid. In a specific example, the *Chlamydophila* or *C. psittaci* nucleic acid is amplified by rt RT-PCR. Techniques for nucleic acid amplification are well-known to those of skill in the art.

Typically, at least two primers are utilized in the amplification reaction, however it is envisioned that one primer can be utilized, for example to reverse transcribe a single stranded nucleic acid such as a single-stranded *Chlamydophila* or *C. psittaci* RNA, followed by hybridization with a *Chlamydophila* or *C. psittaci* primer or probe.

Amplification of a *Chlamydophila* or a *C. psittaci* nucleic acid involves contacting the *Chlamydophila* or *C. psittaci* nucleic acid with one or more primers that are capable of hybridizing to and directing the amplification of the *Chlamydophila* or *C. psittaci* nucleic acid (such as a nucleic acid capable of hybridizing under very high stringency conditions to the complementary *Chlamydophila* or *C. psittaci* nucleic acid). In one embodiment, amplification of a *Chlamydophila* or a *C. psittaci* nucleic acid involves contacting the *Chlamydophila* or *C. psittaci* nucleic acid with one or more primers that are capable of hybridizing to and directing the amplification of the *Chlamydophila* or *C. psittaci* nucleic acid, such as a nucleic acid capable of hybridizing under very high stringency conditions to a complementary sequence of a *Chlamydophila* or *C. psittaci* nucleic acid set forth as SEQ NOs: 11-15, for example a primer that is 15-40 nucleotides long and is at least 95% identical, such as at least 96%, at least 97%, at least 98%, at least 99%, or even 100% identical to the nucleotide sequence set forth as SEQ ID NO: 3, SEQ ID NO: 4, SEQ ID NO: 5, SEQ ID NO: 6, SEQ ID NO: 7, SEQ ID NO: 8, SEQ ID NO: 16, or SEQ ID NO: 17. In some embodiments, the sample is contacted with at least one primer that is specific for a *C. psittaci* genotype, such as those disclosed herein.

In some embodiments, the sample is contacted with at least one pair of primers that include a forward and reverse primer that both hybridize to a *Chlamydophila* nucleic acid specific for *C. psittaci* and/or a *C. psittaci* genotype, such as *C. psittaci* genotype A, B, C, D, E, or F. Examples of suitable primer pairs for the amplification of *Chlamydophila* and/or *C. psittaci* and/or *C. psittaci* genotype-specific nucleic acids are described above.

In one example, the sample is contacted with a pair of primers capable of hybridizing to and amplifying a complementary sequence of a *C. psittaci* nucleic acid including at least one forward primer 15-40 nucleotides long that is at least 95% identical to the nucleotide sequence set forth as SEQ ID NO: 3, SEQ ID NO: 5, or SEQ ID NO: 7, and at least one reverse primer 15-40 nucleotides longs that is at least 95% identical, such as at least 96%, at least 97%, at least 98%, at least 99%, or even 100% identical to the nucleotide sequence set forth as SEQ ID NO: 4, SEQ ID NO: 6, or SEQ ID NO: 8. In another example, the forward and reverse primers include multiple forward and reverse primers that are specific for *Chlamydophila* psittaci and include nucleic acid sequences 15-40 nucleotides longs that are at least 95% identical, such as at least 96%, at least 97%, at least 98%, at least 99%, or even 100% identical to the nucleotide sequences set forth as SEQ ID NOs: 3-8. In yet another example, the forward and reverse primers are specific for *Chlamydophila* psittaci genotypes A, B, C, D or E, and include a nucleic acid sequence at 15-40 nucleotides longs that is least 95% identical, such as at least 96%, at least 97%, at least 98%, at least 99%, or even 100% identical to the nucleotide sequences set forth as SEQ ID NO: 5 or SEQ ID NO: 6. In one embodiment, primers specific for the amplification of *Chlamydophila psittaci* genotype F include a nucleic acid sequence at 15-40 nucleotides longs that is least 95% identical to the nucleotide sequence set forth as SEQ ID NO: 7 or SEQ ID NO: 8.

In instances where hybridization results in a detectable change in signal, for example from the labeled primer, hybridization can be determined for example by high-resolution melt analysis of the amplified PCR product. In this example, the amplified PCR product is subjected to high temperature, for example between 70° C. and 85° C., resulting in separation of the double-stranded amplified PCR product into a single-stranded conformation. For example, a LUX™ primer that hybridizes to nucleic acids in a sample can be extended during amplification, for example using PCR techniques, to form a double-stranded amplification product; this in turn can be separated into a single-stranded amplification product upon exposure to high temperature, thereby resulting in a decrease in fluorescence of the LUX™ primer label. In some instances, high-resolution melt analysis is performed on the amplified product at a temperature of about 75° C.-85° C. in 0.1° C. increments. In another embodiment, high-resolution melt analysis is performed on the amplified product at a temperature of about 75° C.-85° C. in 0.05° C. increments. In yet another embodiment, the high-resolution melt analysis includes two normalization regions, the first between about 75° C. and about 77° C., before separation of the amplified product, and a second between about 83° C. and 85° C., after separation of the amplified product. The inclusion of normalization regions is particularly useful when comparing unrelated samples. The incorporation of normalization regions into the high-resolution melt analysis allows a user to eliminate variations in the melt analysis that may occur as a result of an artifact in the test system.

Figure 6B:
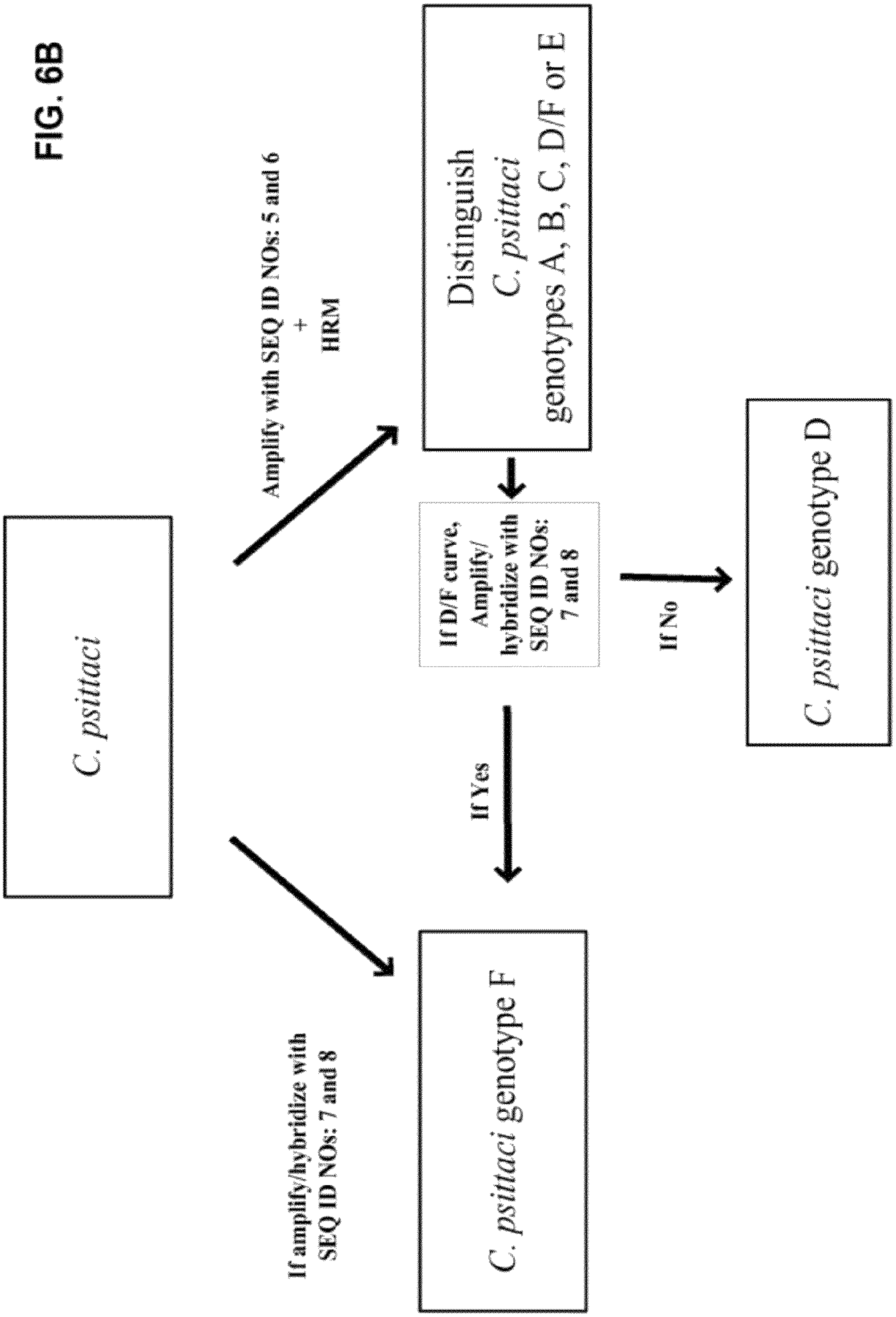
FIG. 6 is a flow chart showing an example of the detection of *Chlamydophila* species (FIG. 6A) and the differentiation of *Chlamydophila psittaci* genotypes A-F (FIG. 6B).

An example of the differentiation of *C. psittaci* genotypes is shown in FIG. 6B. In one embodiment, the amplification of sample nucleic acids by SEQ ID NOs: 5 and 6, followed by HRM analysis of the amplified products can be used to identify the presence of *C. psittaci* genotypes A-F or *C. caviae* in the sample. In such embodiments, distinct melt curves are established herein to determine the presence of *C. psittaci* genotypes A, B, C, E as well as *C. caviae*. The melt curves of *C. psittaci* genotypes D and F are indistinguishable. Thus, in particular examples, following detection of the distinct genotype D/F curve in a sample, nucleic acid amplification with or hybridization of the primers set forth as SEQ ID NOs: 7 and 8 is necessary to differentiate between genotype D and genotype F. The ability to amplify or detect nucleic acids in the sample with the primers set forth as SEQ ID NOs: 7 and 8 is indicative of *C. psittaci* genotype F. The absence of amplification or detection is indicative of *C. psittaci* genotype D.

Any type of thermal cycler apparatus can be used for the amplification of the *Chlamydophila* and *C. psittaci* nucleic acids and/or the determination of hybridization. Examples of suitable apparatuses include a PTC-100® Peltier Thermal Cycler (MJ Research, Inc.; San Francisco, Calif.), a ROBOCYCLER® 40 Temperature Cycler (Stratagene; La Jolla, Calif.), or a GENEAMP® PCR System 9700 (Applied Biosystems; Foster City, Calif.). For real-time PCR, any type of real-time thermocycler apparatus can be used. For example, a ROTOR-GENE Q®, (QIAGEN; Germantown, Md.), a Bio-Rad ICYCLER IQ™, LIGHTCYCLER™ (Roche; Mannheim, Germany), a 7700 SEQUENCE DETECTOR® (Perkin Elmer/Applied Biosystems; Foster City, Calif.), ABI™ systems such as the 7000, 7500, 7700, or 7900 systems (Applied Biosystems; Foster City, Calif.), or an MX4000™, MX3000™ or MX3005™ (Stratagene; La Jolla, Calif.), and Cepheid SMARTCYCLER™ can be used to amplify nucleic acid sequences in real-time.

The amplified *Chlamydophila* or *C. psittaci* nucleic acid, for example a *Chlamydophila* species or *C. psittaci* genotype specific nucleic acid, can be detected in real-time, for example by real-time PCR such as real-time RT-PCR, in order to determine the presence, the identity, and/or the amount of a *Chlamydophila* or *C. psittaci* genotype specific nucleic acid in a sample. In this manner, an amplified nucleic acid sequence, such as an amplified *Chlamydophila* or *C. psittaci* nucleic acid sequence, can be detected using a primer specific for the product amplified from the *Chlamydophila* or *C. psittaci* sequence of interest, such as any of the *Chlamydophila* primers or probes that are specific for *C. psittaci* genotypes A, B, C, D, E, or F discussed herein. Detecting the amplified product includes the use of labeled primers that are sufficiently complementary and hybridize to the nucleic acid sequence of interest, whereupon the primers are extended during PCR amplification. Thus, the presence, amount, and/or identity of the amplified product can be detected by hybridizing a labeled primer, such as a fluorescently labeled primer, complementary to the amplified product. In one embodiment, the detection of a nucleic acid sequence of interest includes the combined use of PCR amplification and a labeled primer such that the product is measured using real-time RT-PCR. In another embodiment, the detection of an amplified nucleic acid sequence of interest includes high-resolution melt analysis of the amplified nucleic acid sequence, such as a melt curve, for example a melt curve with normalization regions that separate the amplified product under high temperature and record the change in fluorescence of the labeled primer as compared to the level of fluorescence of the amplified product prior to high-resolution melt analysis. In yet another embodiment, the detection of an amplified nucleic acid sequence of interest includes the hybridization and amplification of the nucleic acid to primers disclosed herein and separation of the labeled primer and amplified product under high-resolution melt analysis, where a shift in fluorescence as compared to the amplified product indicates a change in conformation of the labeled primer. In some embodiments, detection of the change in signal from the labeled primer occurs after amplification of the sample. In another embodiment, detection of the change in signal from the labeled primer occurs after high-resolution melt analysis of the sample.

In one embodiment, the fluorescently-labeled primers rely upon fluorescence resonance energy transfer (FRET), or in a change in the fluorescence emission wavelength of a sample, as a method to detect hybridization of a DNA primer to the amplified target nucleic acid in real-time. For example, FRET that occurs between fluorogenic labels on different probes or primers (for example, using HYBPROBES®) or between a fluorophore and a non-fluorescent quencher on the same probe or primer (for example, using a molecular beacon, LUX™ primer or a TAQMAN® probe) can identify a probe or primer that specifically hybridizes to the DNA sequence of interest and in this way, using *Chlamydophila* or *C. psittaci* specific probes or primers, can detect the presence, identity, and/or amount of a *Chlamydophila* or a *C. psittaci* in a sample. In one embodiment, the fluorescently-labeled DNA primers used to identify amplification products have spectrally distinct emission wavelengths, thus allowing them to be distinguished within the same reaction tube.

In another embodiment, a melting curve analysis of the amplified target nucleic acid can be performed subsequent to the amplification process. The $T_m$ of a nucleic acid sequence depends on, for example, the length of the sequence, its G/C content and its G/C distribution. Thus, the identification of the $T_m$ for a nucleic acid sequence can be used to identify the amplified nucleic acid.

Kits

The nucleic acid primers disclosed herein can be supplied in the form of a kit for use in the detection, identification, and/or genotyping of *Chlamydophila* or *C. psittaci*. In several embodiments, the nucleic acid primers disclosed herein discriminate between *Chlamydophila* species. In another example, the nucleic acid primers disclosed herein distinguish between strains of *C. psittaci*. In yet another embodiment, the nucleic acid primers disclosed discriminate between a *C. psittaci* and a *C. caviae* nucleic acid. In yet another embodiment, the nucleic acid primers disclosed herein discriminate between a *C. psittaci* and a *C. abortus* nucleic acid. In some embodiments, the nucleic acid primers disclosed herein discriminate between genotypes of *C. psittaci.*

The nucleic acid primers disclosed herein can be supplied in the form of a kit for use in the detection, identification, and/or genotyping of *Chlamydophila* or *C. psittaci* in a sample. In such a kit, an appropriate amount of one or more of the nucleic acid primers disclosed herein is provided in one or more containers or held on a substrate. A nucleic acid primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid primers for use in detection, identification, and genotyping of *Chlamydophila* or *C. psittaci* nucleotide sequences.

In some applications, one or more primers (as described above), such as pairs of primers, may be provided in premeasured single use amounts in individual, typically disposable, tubes or equivalent containers. With such an arrangement, the sample to be tested for the presence of *Chlamydophila* or *C. psittaci* nucleic acids can be added to the individual tubes and amplification carried out directly. In one embodiment, hybridization of the primers to nucleic acids in a sample is determined by PCR techniques. In another embodiment, hybridization of the primers to nucleic acids in a sample is determined by high-resolution melt analysis of the amplified PCR product. In some examples, high-resolution melt analysis is performed on the solution in the same tube in which the sample was amplified. One advantage of the above system is the ability to amplify, screen and detect amplification of nucleic acids, such as *Chlamydophila* or *C. psittaci* nucleic acids, within a single reaction vessel, thereby reducing the likelihood of contamination.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A kit may include more than two primers in order to facilitate the PCR amplification of a larger number of *Chlamydophila* or *C. psittaci* nucleotide sequences in a single test reaction.

In some embodiments, kits also may include the reagents necessary to carry out PCR amplification reactions, including DNA sample preparation reagents, appropriate buffers (such as polymerase buffer), salts (for example, magnesium chloride), and deoxyribonucleotides (dNTPs).

One or more control sequences for use in the PCR reactions also may be supplied in the kit (for example, for the detection of human RNAse P).

Particular embodiments include a kit for detecting and genotyping a *Chlamydophila* or *C. psittaci* nucleic acid based on the components described above. Such a kit includes at least one primer specific for a *Chlamydophila* or *C. psittaci* nucleic acid (as described herein) and instructions. A kit may contain more than one different primer, such as 2, 3, 4, 5, 6, 7, 8, 9, 10, 11, 12, 13, 14, 15, 20, 25, 50, 100, or more primers. The instructions may include directions for obtaining a sample, processing the sample, preparing the primers, and/or contacting each primer with an aliquot of the sample. In certain embodiments, the kit includes an apparatus for separating the different primers, such as individual containers (for example, microtubules) or an array substrate (such as, a 96-well or 384-well microtiter plate). In particular embodiments, the kit includes prepackaged primers, such as primers suspended in suitable medium in individual containers (for example, individually sealed EPPENDORF® tubes) or the wells of an array substrate (for example, a 96-well microtiter plate sealed with a protective plastic film). In other particular embodiments, the kit includes equipment, reagents, and instructions for extracting and/or purifying nucleotides from a sample both prior to, and after, amplification.

Synthesis of Oligonucleotide Primers

In vitro methods for the synthesis of oligonucleotides are well known to those of ordinary skill in the art; such methods can be used to produce primers for the disclosed methods. The most common method for in vitro oligonucleotide synthesis is the phosphoramidite method, formulated by Letsinger and further developed by Caruthers et al. (*Methods Enzymol.* 154: 287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), *Oligonucleotide Synthesis. A practical approach*, IRL Press, 1984.

In general, the synthesis reactions proceed as follows: A dimethoxytrityl or equivalent protecting group at the 5' end of the growing oligonucleotide chain is removed by acid treatment. (The growing chain is anchored by its 3' end to a solid support such as a silicon bead.) The newly liberated 5' end of the oligonucleotide chain is coupled to the 3'-phosphoramidite derivative of the next deoxynucleotide to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for example, U.S. Pat. Nos. 4,415,732, 4,458,066, 4,500,707, 4,973,679, and 5,132,418. Oligonucleotide synthesizers that employ this or similar methods are available commercially (for example, the PolyPlex oligonucleotide synthesizer from Gene Machines, San Carlos, Calif.). In addition, many companies will perform such synthesis (for example, Sigma-Genosys, The Woodlands, Tex.; Qiagen Operon, Alameda, Calif.; Integrated DNA Technologies, Coralville, Iowa; and TriLink BioTechnologies, San Diego, Calif.).

The following examples are provided to illustrate particular features of certain embodiments. However, the particular features described below should not be construed as limitations on the scope of the invention, but rather as examples from which equivalents will be recognized by those of ordinary skill in the art.

EXAMPLE 1

Materials and Methods

This example describes the materials and methods used to determine the specificity and sensitivity of the disclosed primers to detect and discriminate between species of *Chlamydophila* and strains of *C. psittaci*.

Bacterial Strains and Specimens

The disclosed primers were tested for specificity of *C. psittaci* nucleic acids using reference strain isolates DD-34 (ATCC VR-854), CP3 (ATCC VR-574), CT1, NJ1, MN (ATCC Vr-122), and VS-225 along with 169 specimens acquired from companion or aviary birds and mammals. The specimens were previously submitted to the Infectious Diseases Laboratory at the College of Veterinary Medicine, University of Georgia, and tested positive at the time of collection (2004 to 2007) for *C. psittaci* or other *Chlamydophila* species by a PCR-based assay. All specimens were obtained from a recommended specimen source: i.e., conjunctival, choanal, or cloacal swabs or whole blood.

*C. psittaci* Culture

*C. psittaci* reference strains were propagated in Vero cell monolayers grown in 25-$cm^2$ culture flasks in Eagle's minimal essential medium (MEM) supplemented with MEM nonessential amino acids, 2 μM L-glutamine, 20 μM HEPES buffer, 10% fetal calf serum, 20 μg/ml streptomycin, and 25 μg/ml vancomycin. Confluent Vero cell monolayers were inoculated by replacing the growth medium with 1 ml of stock *C. psittaci* culture diluted 1:10 in MEM containing 1 μg/ml of cycloheximide. The inoculated monolayers were placed at 37° C. for 2 hours before an additional 4 ml of MEM containing cycloheximide was added to each flask. Cultures were incubated for 7 days at 37° C. or until the monolayers demonstrated approximately 70% cytopathic effect and the remaining Vero cells were scraped from the flask into the medium. One milliliter of each culture was centrifuged at 20,000×g for 60 min, and the pellet was resuspended in nuclease-free water (Promega Co.) and used for DNA extraction using standard conditions. The remaining culture was dispensed into aliquots and frozen at −70° C. Titration of cultures was performed with 96-well flat-bottom microtiter plates containing Vero cells. Frozen *C. psittaci* cultures of 50 μl quantities at 10-fold dilutions were used to inoculate wells of Vero cells in triplicate. After incubation for 72 hours at 37° C. in a 5% $CO_2$ atmosphere, the medium was removed and the cells were fixed with methanol and stained with a *Chlamydia* genus-specific monoclonal antibody (Bio-Rad). Inclusions (inclusion forming units/ml) were counted using an inverted fluorescence microscope.

DNA Extraction for Real-Time PCR

DNA from *C. psittaci* cultures was extracted using a QiaAmp DNA minikit (Qiagen, Inc.) according to the manufacturer's instructions. The DNA was eluted into 200 μl of Qiagen elution buffer and stored at −70° C. until tested.

LUX™ Primer Design and Optimization

Primer sets targeting the variable regions of the *C. psittaci* ompA gene were designed. LUX™ chemistry (Invitrogen, CA) utilizes a 5-carboxyfluorescein (FAM)-labeled primer and a corresponding unlabeled primer. All primer sets were designed using the *C. psittaci* 6BC ompA gene (GENBANK® Accession no. X56980), the 90/105 ompA gene (GENBANK® Accession no. AY762608), and the 7778B15 ompA gene (GENBANK® Accession no. AY762612). *C. psittaci* primer sequences and expected amplicon sizes are listed in Table 1. Primer set Ppac was designed to amplify all *C. psittaci* genotypes, while primer set GTpc was designed to specifically amplify only *C. psittaci* genotypes. The Ppac assay demonstrated 96% efficiency, while the GTpc assay displayed 99% efficiency, calculated using a standardized dilution series of quantitated DNA of *C. psittaci* tested in triplicate over 6 logs (200 pg to 2 fg). The average for this data is reported as the square of the coefficient of regression values (efficiency); both assays (Ppac and GTpc) had a lower limit of detection of at least 200 fg. A specific *C. caviae* marker targeting the ompA gene of *C. caviae* (GENBANK® Accession no. AF269282) was designed using the above-described primer chemistry with unlabeled C.cav-F (5'-CCGTTGCA-GACAGGAATAACA-3', SEQ ID NO: 17) and FAM-labeled C.cav-R (5'-cacaaaGCTAAGAAAGCCGCGTTTG"t"G-3', SEQ ID NO: 16) (the 5' lowercase letters are not part of the primer but correspond to a self-quenching complementary tail; "t" represents the FAM binding location). The expected amplicon size using the *C. caviae* specific primers is 78 bp.

Real-Time PCR and HRM Analysis

For development of the methods disclosed herein, novel oligonucleotide primers were designed based on previously published ompA gene sequences and sequences available in GENBANK® using D-LUX™ design software (Invitrogen, CA). The primers for the LUX™ real-time PCR assay were designed to amplify the ompA gene of *C. psittaci*. The *C. psittaci* forward real-time PCR primers were 3'-labeled with 6-carboxy-fluorescein (FAM) and possessed a 5' self quenching moiety (hairpin structure). *C. caviae* primers were 3'-labeled with 6-carboxy-fluorescein (FAM) and possessed a 5'-self quenching moiety (hairpin structure). The corresponding reverse primers were designed and were used along with the labeled forward primer to amplify the target nucleic acid. A full list of primer sequences are provided in Table 1.

increments, with fluorescence normalization regions between 75.5° C. and 76° C., before separation and at 84° C. to 84.5° C. after the separation. All isolates were tested in triplicate. All specimens (avian and mammalian) were screened for the presence of *C. psittaci*, followed by genotyping, if applicable.

High-resolution melt (HRM) curves are derived by selecting two normalization regions, one occurring prior to the melting of the double-stranded product and one following complete separation of the two strands. Each region is generated by default by the software associated with the instrument performing the high-resolution melt analysis, but may be manipulated manually to achieve optimum results. The normalization regions function to normalize the florescence of the melt curves from the raw channel by averaging all starting and ending fluorescence values such that the end point value of each sample is identical to the average. This allows for the melting profile of each isolate to be analyzed relative to other isolates, which is particularly useful when compared unrelated samples.

Sequencing

Amplification of the ompA gene from isolate strains (DD34, CP3, CT1, NJ1, Vr-122 and VS-225) and specimens (3, 5, 25, 30, 31 and 83) was performed using previously

TABLE 1

Real-time PCR primers[a]

| Oligonucleotide | Sequence | Amplicon size |
|---|---|---|
| Ppac forward, Labeled | 5'-gaacccTATTGTTTGCCGCTACGGGT"t"C-3' (SEQ ID NO: 3) | 109 |
| Ppac reverse, unlabeled | 5'-TCCTGAAGCACCTTCCCACA-3' (SEQ ID NO: 4) | |
| GTpc forward, Labeled | 5'-gaactcaTGTGCAACTTTAGGAGCTGAG"t"TC-3' (SEQ ID NO: 5) | 274 |
| GTpc reverse, unlabeled | 5'-GCTCTTGACCAGTTTACGCCAATA-3' (SEQ ID NO: 6) | |
| GT-F forward, Labeled | 5'-gacgcCATTCGTGAACCACTCAGCG"t"C-3' (SEQ ID NO: 7) | 98 |
| GT-F reverse, unlabeled | 5'-CTCCTACAGGAAGCGCAGCA-3' (SEQ ID NO: 8) | |
| C. cav-reverse, labeled | (5'-cacaaaGCTAAGAAAGCCGCGTTTG"t"G-3' (SEQ ID NO: 16) | 78 |
| C. cav-forward, unlabeled | 5'-CCGTTGCAGACAGGAATAACA-3' (SEQ ID NO: 17) | |

[a]The 5' lowercase letters are not part of the primer itself but correspond to a self-quenching, complementary tail.
b, "t" represents the FAM binding location.

Utilization of LUX™ chemistry primers and HRM analysis was performed as follows. The reaction mixture for all primer sets was prepared using a SuperMix-UDG platinum quantitative PCR kit (Invitrogen, CA) containing the following components per reaction mixture: 12.5 μl of 2× master mix, final concentrations of 100 nM each of the forward and reverse primers, 0.15 μl of platinum Taq polymerase (5 U/μl), 5 ng of a template, and nuclease-free water (Promega) added to give a final volume of 25 μl. Real-time PCR was performed with a Corbett Rotor-Gene 6000™ (Corbett Life Sciences) under the following cycling conditions: 1 cycle at 95° C. for 2 min, followed by 45 cycles at 95° C. for 5 seconds and 62° C. for 15 seconds, with data acquired at the 62° C. step in the green channel. Following amplification, high-resolution melt analysis was performed between 75° C. and 85° C. in 0.05° C.

published primers (Kaltenboeck et al., 1993, *J. Bacteriol*, 175:487-502 which is incorporated herein by reference to the extent that it discloses the previously identified primers) and newly developed primers ompA-F (5'-ACTATGTGGGAAG-GTGCT-3') (SEQ ID NO: 9) and ompA-R (5'-TAGACT-TCATTTTGTTGATCTGA-3') (SEQ ID NO: 10). The PCR mixture was prepared using a SuperMix-UDG platinum quantitative PCR kit (Invitrogen, CA) containing the following components per reaction mixture: 5 μl of 10×PCR master mix-$MgCl_2$, 1.5 μl 50 mM $MgCl_2$, final concentrations of 100 nM each of the forward and reverse primers, 0.5 μl of platinum Taq polymerase (5 U/μl), 1 μl of 10 μM PCR nucleotide mixture (Promega, CO.), 5 ng of a template, and nuclease-free water (Promega, CO) added to give a final volume of 50 μl.

A DNA engine dyad peltier thermocycler (Bio-Rad, CA.) was used for amplification under the following cycling conditions: 1 cycle at 95° C. for 2 min, followed by 50 cycles at 95° C. for 1 min, 59° C. for 1 min, and 72° C. for 2 min. Amplified samples were purified using a QIAquick gel extraction kit (Qiagen, CA) after separation on a 1% agarose gel. Sequencing was performed with an ABI 3130XL instrument (Applied Biosystems, Inc.) under standard conditions for an 80-cm capillary. Consensus sequences were generated using DNAstar Lasergene SeqMan Pro software and aligned with published ompA gene sequences for each genotype by using Clustal W software. The GENBANK® Accession numbers used for alignment are as follows: AY762608, AY762609, AF269261, AY762610, AY762611, AY762612, and AY762613.

Real-Time PCR Analytical Sensitivity and Specificity Determinations

For lower limit of detection (LLD) assessments, serial dilution over 6-logs (equivalent to 200 pg to 2 fg) of quantitated *C. psittaci* DNA was prepared and aliquots tested using the above real-time PCR protocols. Both the Ppac assay and the GTpc assay had a lower limit of detection of at least 200 fg.

EXAMPLE 2

Specificity of LUX™ Primers to Detect and Identify *C. psittaci* Nucleic Acids This example shows the ability of the newly-developed *C. psittaci*-specific primers to detect *C. psittaci*. The species-specificity of the primers is also confirmed. The use of these primers to identify *Chlamydophila* species as well as differentiate between *C. psittaci* genotypes as described in this example is shown in FIG. 6.

Three *C. psittaci* primer pairs described herein (SEQ ID NOs: 3 and 4, SEQ ID NOs: 5 and 6, and SEQ ID NOs: 7 and 8) successfully amplified sequences from Ppac, GTpc, and GT-F (respectively) from reference strains of *C. psittaci* using real-time PCR and HRM analysis. The specificity of these primers was determined by a lack of PCR amplification product using 15 ng of DNA template from a variety of bacterial and viral agents (Table 2). Human DNA was also unreactive with the tested primer pairs. The newly developed *C. psittaci*-specific primers also lacked reactivity with the four *Chlamydophila* agents tested.

Figure 3A:
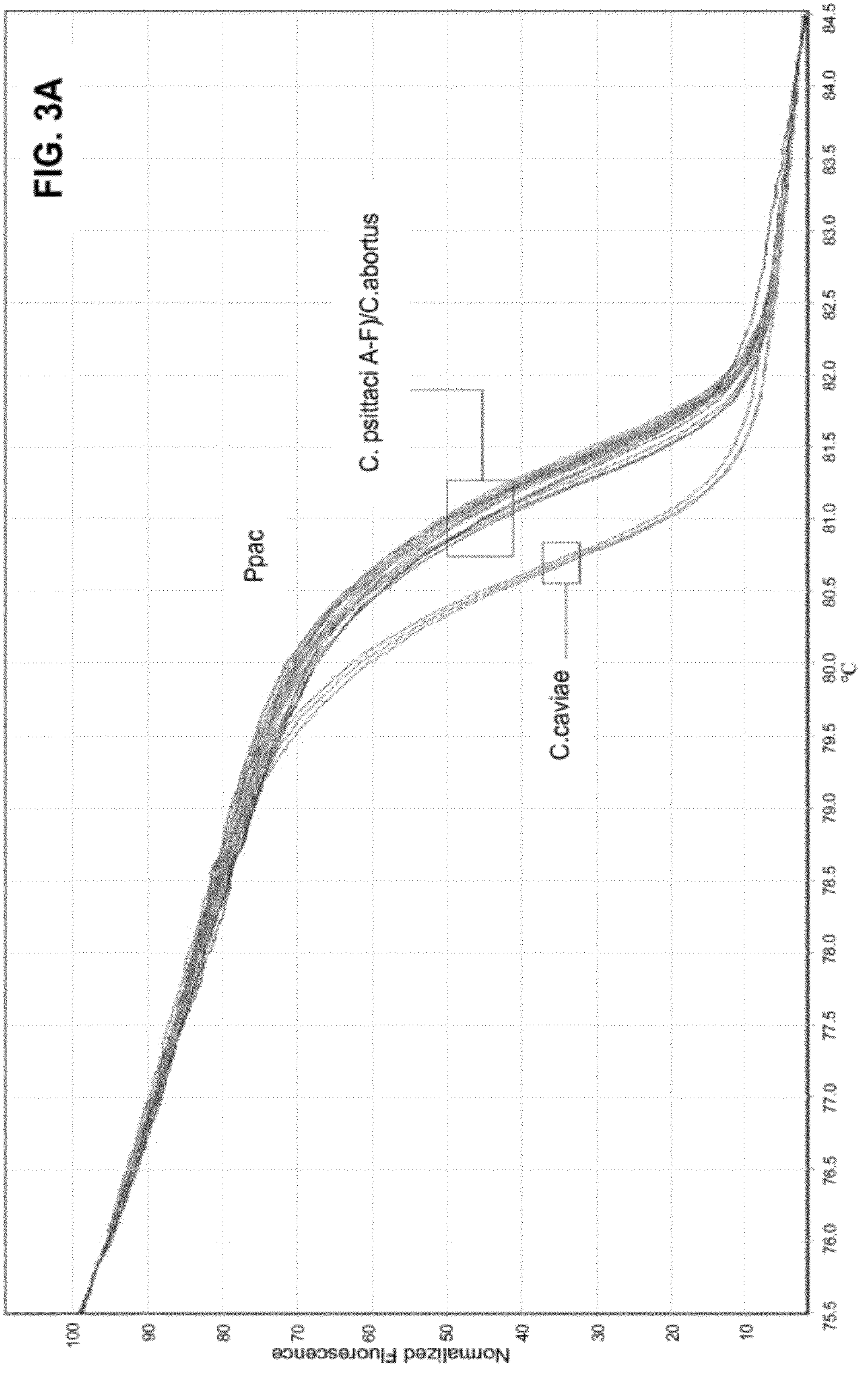
FIGS. 3A-3C are High-resolution Melt (HRM) analysis curves obtained from the melting of a sample containing *Chlamydophila* nucleic acid amplified with *Chlamydophila* specific primers.

The results of the HRM analysis using the Ppac primers yielded similar melt curves for each *C. psittaci* genotype (FIG. 3A). The Ppac primer amplified *C. caviae* but this amplification product was easily distinguishable from *C. psittaci* nucleic acids by HRM analysis. In particular, the distinction of *C. caviae* nucleic acids from *C. psittaci* nucleic acids was determined by the observation of a dissociation curve occurring prior to the dissociation curve of *C. psittaci* (FIG. 3A). In contrast, the dissociation curve of *C. abortus* obtained using the Ppac primers was indistinguishable from the corresponding dissociation curve of *C. psittaci* (FIG. 3A).

Figure 3B:
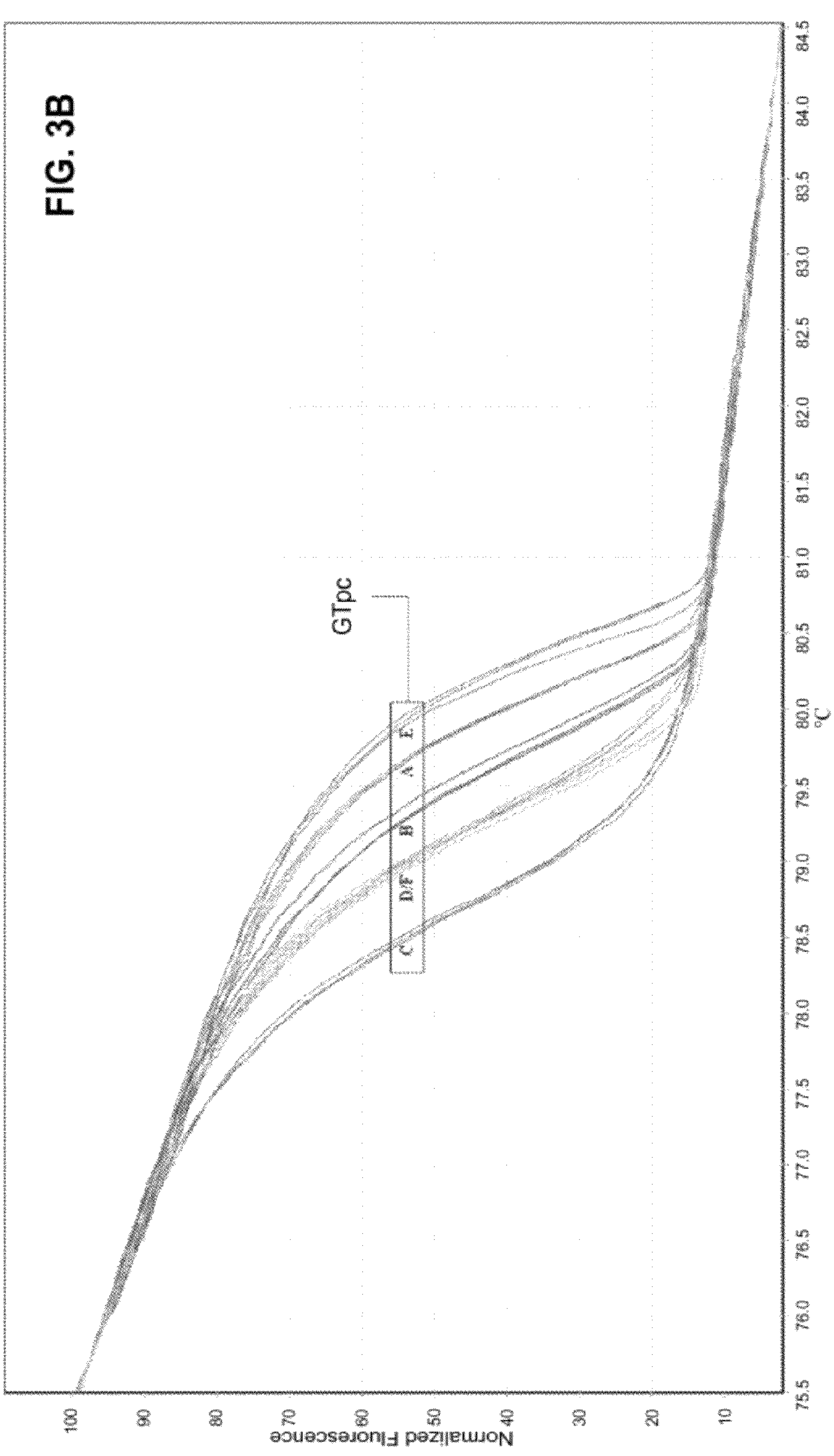
Figure 3C:
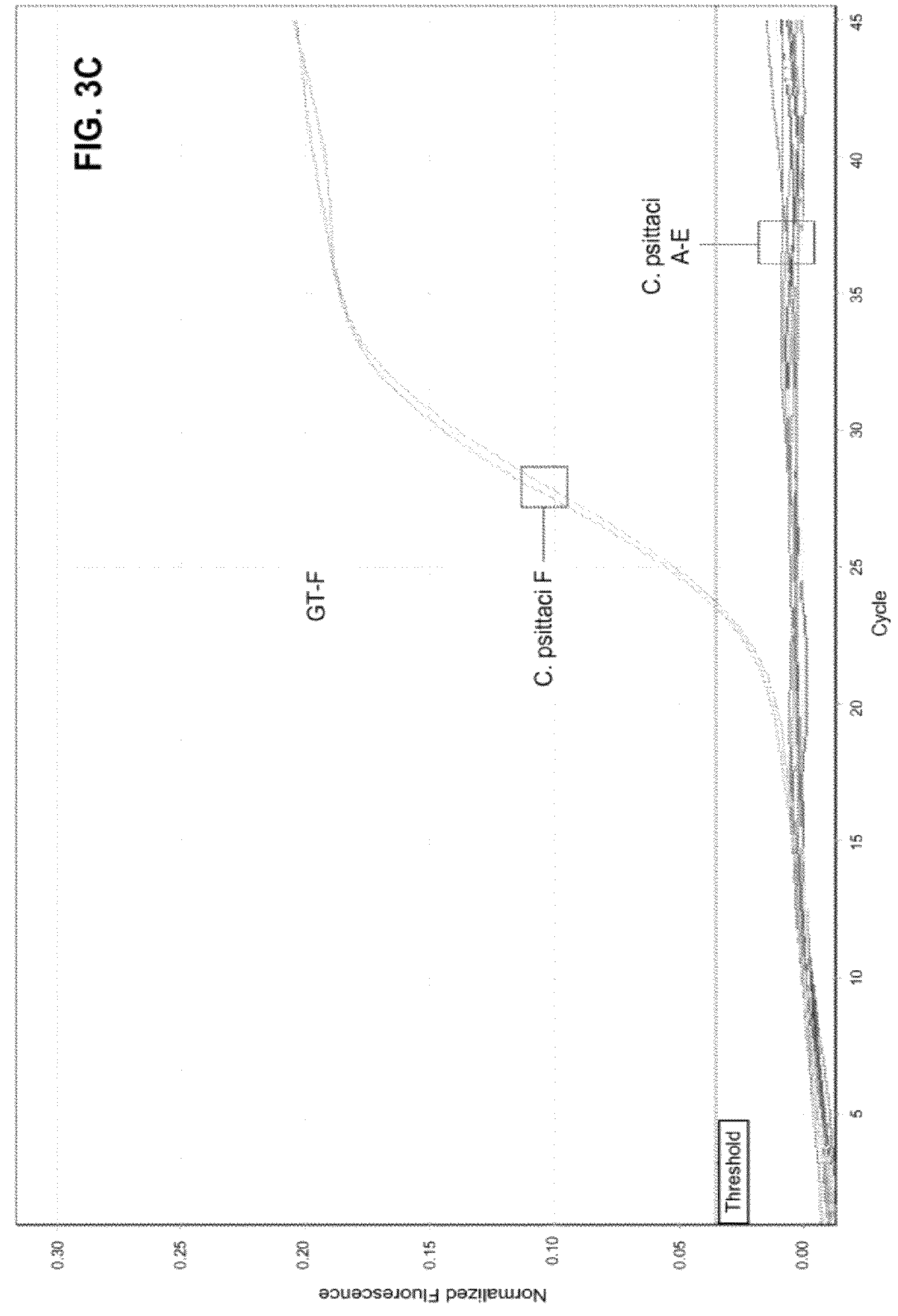

HRM analysis of the amplified product from each isolate in combination with the GTpc primer set produced a distinct melt curve profile for all *C. psittaci* genotypes except genotypes D and F, which were separated using the *C. psittaci* F genotype-specific primer, GT-F (FIG. 3C). Separation among the *C. psittaci* genotypes occurs in incremental shifts, with genotype E being farthest right (dissociating at the highest temperature), with *C. psittaci* genotypes A, B, D/F, and C all dissociating at progressively lower temperatures (FIG. 3B).

Figure 5A:
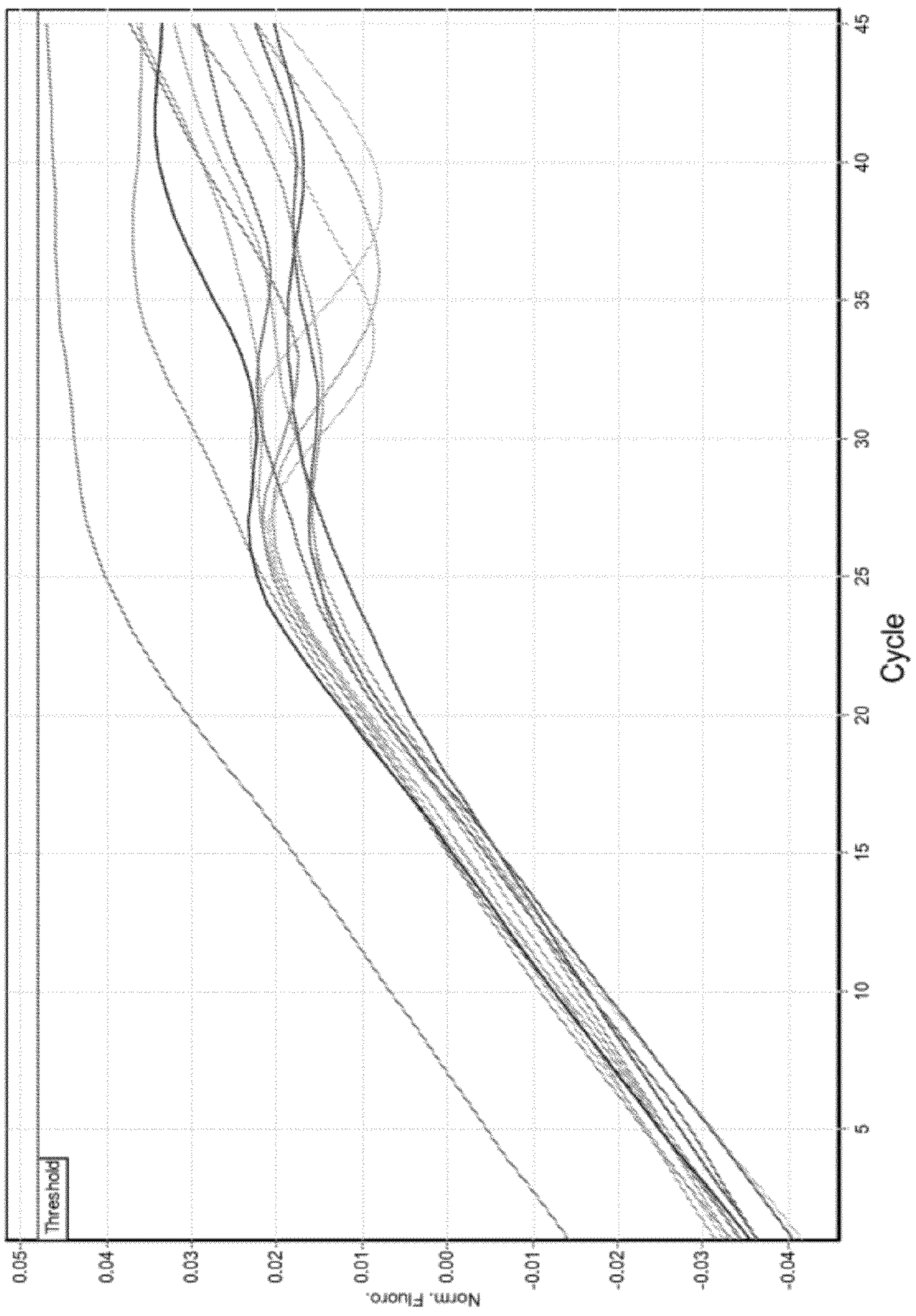
FIGS. 5A-5B are graphs of Real-Time Polymerase Chain Reaction data obtained from the amplification of samples containing *Chlamydophila psittaci* nucleic acids amplified with *Chlamydophila caviae* specific primers.

Additionally, *C. caviae* can be distinguished from *C. psittaci* genotypes using the GTpc primer set and HRM analysis. The *C. caviae* reference strain was found to melt between *C. psittaci* genotypes D/F and B; further verification was also achieved by using the additional species-specific *C. caviae* primer set under standard RT-PCT conditions (SEQ ID NO: 16 and SEQ ID NO: 17). Samples containing *C. psittaci* were amplified under real-time PCR conditions and an amplification plot disclosing the threshold value was determined (FIG. 5A). In this experiment, none of the samples containing *C. psittaci* were amplified to a sufficient extent for the sample to be positively identified as *C. caviae*.

*C. abortus* cannot be differentiated from *C. psittaci* using the Ppac primer set. However, the GTpc primer set does not amplify *C. abortus* and therefore provides a method to eliminate *C. abortus* as a suspected pathogen in a *Chlamydophila* sample, where the sample is successfully amplified using the GTpc primer set.

TABLE 2

| Specificity Panel[a] Agents screened for reactivity with primers: SEQ ID NOs: 3-8 and SEQ ID NO: 16 and 17: |
|---|
| *Candida albicans* |
| *Bordetella pertussis* |
| *Chlamydophila felis* |
| *Chlamydophila pecorum* |
| *Chlamydophila pneumoniae* |
| *Chlamydia trachomatis* |
| *Corynebacterium diphtheriae* |
| *Coxiella burnetii* |
| *Escherichia coli* |
| *Haemophilus influenzae* |
| *Lactobacillus planitarium* |
| *Legionella longbeachae* |
| *Legionella pneumophila* |
| *Moraxella catarrhalis* |
| *Mycoplasma arginini* |
| *Mycoplasma buccale* |
| *Mycoplasma faucium* |
| *Mycoplasma fermentans* |
| *Mycoplasma genitalium* |
| *Mycoplasma hominis* |
| *Mycoplasma hyorhinis* |
| *Mycoplasma lipophilum* |
| *Mycoplasma orale* |
| *Mycoplasma penetrans* |
| *Mycoplasma pirum* |
| *Mycoplasma salivarium* |
| *Mycobacterium tuberculosis* |
| *Neisseria elongata* |
| *Neisseria meningitidis* |
| *Pseudomonas aeruginosa* |
| *Staphylococcus aureus* |
| *Staphylococcus epidermidis* |
| *Streptococcus pneumoniae* |
| *Streptococcus pyogenes* |
| *Streptococcus salivarius* |
| *Ureaplasma urealyticum* |
| Human DNA |
| Adenovirus |
| Coronavirus |
| Parainfluenza virus 2 |
| Parainfluenza virus 3 |
| Rhinovirus |
| Influenza virus A |
| Influenza virus B |
| Respiratory syncytial virus A |
| Respiratory syncytial virus B |

[a]Shown are bacterial and viral species (15 ng) screened for cross-reactivity by using the disclosed real-time PCR assay.

All agents listed were undetected (no amplification).

EXAMPLE 3

Specimen Testing

This example shows the use of the disclosed primers to screen DNA specimens for the presence of *C. psittaci* and *C. caviae*. The genotypes of the *C. psittaci* identified in the specimens were also determined.

One hundred sixty-nine specimens obtained from birds and companion mammals were screened along with reference strains. Of these archived nucleic acid preparations, 107 (63.3%) were positive for chlamydial DNA, 98 (91.6%) were positive for *C. psittaci*, and 9 (8.4%) were positive for *C. caviae*. Of the positive *C. psittaci* samples, 70 (71.4%) were genotype A, 3 (3.1%) were genotype B, 4 (4.1%) were genotype E, and 21 (21.4%) were positive for *C. psittaci* (positive amplification for both Ppac and GTpc markers) but could not be typed using this assay, due to inconclusive melt curve data (Table 3). All *C. caviae* strains were obtained from guinea pig specimens.

TABLE 3

Real-time PCR and HRM genotyping results for avian and mammalian specimens[a]

| Specimen No. | Specimen Origin | Bacterial Sp.[b] | Genotype |
|---|---|---|---|
| 1 | Lovebird | * | A |
| 2 | Cockatiel | * | A |
| 3 | Macaw | * | E |
| 4 | Lovebird | * | A |
| 5 | Cockatiel | * | E |
| 6 | Sun conure | * | A |
| 7 | Sun conure | * | A |
| 8 | Sun conure | * | A |
| 9 | Sun conure | * | A |
| 10 | Sun conure | * | A |
| 11 | Sun conure | * | A |
| 12 | Sun conure | * | A |
| 13 | Cockatiel | * | A |
| 14 | Cockatiel | * | A |
| 15 | Parakeet | * | A |
| 16 | Cockatiel | * | A |
| 17 | Not given | * | A |
| 18 | Amazon | * | A |
| 19 | Macaw | * | A |
| 20 | Parakeet | * | A |
| 21 | Green cheek | * | A |
| 22 | Green cheek | * | A |
| 23 | Cockatiel | * | A |
| 24 | Pooled cockatiels | * | A |
| 25 | Cockatiel | * | A |
| 26 | Cockatiel | * | A |
| 27 | Amazon | * | A |
| 28 | Cockatiel | * | A |
| 29 | Lovebird | * | A |
| 30 | Pigeon | * | B |
| 31 | Pigeon | * | B |
| 32 | Cockatiel | * | A |
| 33 | Cockatiel | * | A |
| 34 | Cockatiel | * | A |
| 35 | Cockatiel | * | A |
| 36 | Guinea pig | *C. caviae* | |
| 37 | Yellow-naped Amazon | * | A |
| 38 | Pionus | * | A |
| 39 | Cockatiel | * | A |
| 40 | Guinea pig | *C. caviae* | |
| 41 | Cockatiel | * | A |
| 42 | Cockatiel | * | A |
| 43 | Cockatiel | * | A |
| 44 | Guinea pig | *C. caviae* | |
| 45 | Guinea pig | *C. caviae* | |
| 46 | Lori | * | B |
| 47 | Lovebird | * | A |
| 48 | Amazon | * | A |
| 49 | Hawkhead | * | A |

TABLE 3-continued

Real-time PCR and HRM genotyping results for avian and mammalian specimens[a]

| Specimen No. | Specimen Origin | Bacterial Sp.[b] | Genotype |
|---|---|---|---|
| 50 | Ringneck | * | A |
| 51 | Conure | * | A |
| 52 | Macaw | * | A |
| 53 | African gray | * | A |
| 54 | Cockatiel | * | A |
| 55 | Cockatiel | * | A |
| 56 | Cockatiel | * | A |
| 57 | Guinea pig | *C. caviae* | |
| 58 | Guinea pig | *C. caviae* | |
| 59 | Sun conure | * | A |
| 60 | Guinea pig | *C. caviae* | |
| 61 | Pigeon | * | E |
| 62 | Cockatiel | * | A |
| 63 | Guinea pig | *C. caviae* | |
| 64 | Cockatiel | * | A |
| 65 | Amazon | * | A |
| 66 | DYH Amazon | * | A |
| 67 | Cockatiel | * | A |
| 68 | Guinea pig | *C. caviae* | |
| 69 | Cockatiel | * | A |
| 70 | Cockatiel | * | A |
| 71 | Amazon | * | A |
| 72 | Amazon | * | A |
| 73 | Amazon | * | A |
| 74 | Cockatiel | * | |
| 75 | Cockatiel | * | A |
| 76 | Brown crown | * | A |
| 77 | Cockatiel | * | A |
| 78 | Lovebird | * | A |
| 79 | Cockatiel | * | A |
| 80 | Cockatiel | * | A |
| 81 | Cockatiel | * | E |
| 82 | Macaw | * | A |
| 83 | Parrotlet | * | A |
| 84 | Cockatiel | * | A |
| 85 | Amazon | * | A |
| 86 | Amazon | * | A |

[a]Results of real-time PCR testing and HRM analysis are shown for 86 *chlamydia*-positive avian and mammalian specimens.
[b]* indicates *C. psittaci*

EXAMPLE 4

Sequencing Analysis

The ompA gene was sequenced for all available reference strains and a subset of *C. psittaci*-positive specimens that contained nucleic acids in sufficient amounts and of sufficient quality, acquired from the Infectious Diseases Laboratory, University of Georgia, as described above. The data shows that methods of identifying *C. psittaci* described herein correctly identified DD34 and specimens 25 and 83 as genotype A, CP3 and specimens 30 and 31 as genotype B, CT1 as genotype C, NJ1 as genotype D, Vr-122 and specimens 3 and 5 as genotype E, and VS-225 as genotype F. The sequence alignment of the target regions for this assay within the ompA gene of *C. psittaci* genotypes A-F are shown in FIGS. 4A and 4B. Alignment of the Ppac amplicon sequences yielded the consensus sequence set forth as SEQ ID NO: 18. Of *C. psittaci* genotypes A-F, only genotype C had had a variation within the Ppac amplicon, which is set forth as SEQ ID NO: 19. Alignment of the GTpc amplicons of *C. psittaci* genotypes A-F also yielded a consensus sequence (SEQ ID NO: 20). However, considerably more divergence was observed between the six genotypes. (SEQ ID NOs: 21-26). The nucleotide sequences of the Ppac amplicon consensus, Ppac amplicons from genotype C, GTpc amplicon consensus (with nonconsensus positions indicated by "N"), and GTpc amplicons from genotypes A-F are as follows:

Ppac amplicon consensus
(SEQ ID NO: 18)
ATCGGCATTATTGTTTGCCGCTACGGGTTCCGCTCTCTCCTTACAAGCC

TTGCCTGTAGGGAACCCAGCTGAACCAAGTTTATTAATCGATGGCACTA

TGTGGGAAGGTGCTTCAGGAGA

Ppac C. psittaci genotype C amplicon
(SEQ ID NO: 19)
ATCGGCATTATTATTTGCCGCTACGGGTTCCGCTCTCTCCTTACAAGCC

TTGCCTGTAGGGAACCCAGCTGAACCAAGTTTATTAATCGATGGCACTA

TGTGGGAAGGTGCTTCAGGAGA

GTpc amplicon consensus
(SEQ ID NO: 20)
GGGAATGTGGTTGTGCAACTTTAGGAGCTGAGTTCCAATACGCTCAATC

TAATCCTAANATTGAAATGCTCAANGTNACTTCAAGCCCAGCACAATTT

GTGATTCACAAACCAAGAGGCTATAAAGGANCTNGCTCGAATTTTCCTT

TACCTATAACNGCTGGNACANNNGNNGCTACAGANACNAAATCNGCNAC

ANTNAAATANCATGAATGGCAAGTNGGNCTNGCNCTNTCTTACAGATTG

AANATGCTTGTTCCNTANATTGGCGTAAACTGGTCAAGAGCAACTTTTG

ATGCTG

GTpc C. psittaci genotype A amplicon
(SEQ ID NO: 21)
GGGAATGTGGTTGTGCAACTTTAGGAGCTGAGTTCCAATACGCTCAATC

TAATCCTAAGATTGAAATGCTCAACGTCACTTCAAGCCCAGCACAATTT

GTGATTCACAAACCAAGAGGCTATAAAGGAGCTAGCTCGAATTTTCCTT

TACCTATAACGGCTGGAACAACAGAAGCTACAGACACCAAATCAGCTAC

AATTAAATACCATGAATGGCAAGTAGGCCTCGCCCTGTCTTACAGATTG

AATATGCTTGTTCCATATATTGGCGTAAACTGGTCAAGAGCAACTTTTG

ATGCTG

GTpc C. psittaci genotype B amplicon
(SEQ ID NO: 22)
GGGAATGTGGTTGTGCAACTTTAGGAGCTGAGTTCCAATACGCTCAATC

TAATCCTAAGATTGAAATACTCAACGTCACTTCAAGCCCAGCACAATTT

GTGATTCACAAACCAAGAGGCTATAAAGGAGCTAGCTCGAATTTTCCTT

TACCTATAACGGCTGGAACAACAGAAGCTACAGACACCAAATCAGCTAC

AATTAAATACCATGAATGGCAAGTAGGCCTCGCCCTGTCTTACAGATTG

AATATGCTTGTTCCATATATTGGCGTAAACTGGTCAAGAGCAACTTTTG

ATGCTG

GTpc C. psittaci genotype C amplicon
(SEQ ID NO: 23)
GGGAATGTGGTTGCGCAACTTTAGGAGCTGAATTCCAATACGCTCAATC

TAATCCTAAAATTGAAATGTTGAATGTAATCTCCAGCCCAGCACAATTT

GTGGTTCACAAGCCTAGAGGATACAAGGGAACGTCCGCCAACTTTCCTT

TACCTGCAAATGCAGGCACAGAGGCTGCTACGGATACTAAATCTGCAAC

ACTCAAATATCATGAATGGCAAGTTGGTCTAGCACTCTCTTACAGATTG

AACATGTTAGTTCCTTACATTGGCGTAAACTGGTCACGAGCAACTTTTG

ATGCCG

GTpc C. psittaci genotype D amplicon
(SEQ ID NO: 24)
GGGAATGTGGTTGTGCGACTTTAGGAGCCGAGTTCCAATACGCTCAATC

TAATCCTAAAATTGAAATGCTCAATGTAACTTCAAGCCCAGCACAATTT

GTGATTCACAAACCAAGAGGCTATAAAGGAACTGGCTCGAATTTTCCTT

TACCTATAGACGCGGGTACAGAGGCTGCTACAGATACTAAGTCTGCAAC

ACTCAAATATCATGAATGGCAAGTTGGTCTAGCACTCTCTTACAGATTG

AACATGCTTGTTCCTTACATTGGCGTAAACTGGTCAAGAGCAACTTTTG

ATGCTG

GTpc C. psittaci genotype E amplicon
(SEQ ID NO: 25)
GGGAATGTGGTTGTGCAACTTTAGGAGCTGAGTTCCAATACGCTCAATC

TAATCCTAAGATTGAAGTGCTCAACGTCACTTCAAGCCCAGCACAATTT

GTGATTCACAAACCAAGAGGCTATAAAGGAGCTAGCTCGAATTTTCCTT

TACCTATAACGGCTGGAACAACAGAAGCTACAGACACCAAATCAGCTAC

AATTAAATACCATGAATGGCAAGTAGGCCTCGCCCTGTCTTACAGATTG

AATATGCTTGTTCCATATATTGGCGTAAACTGGTCAAGAGCAACTTTTG

ATGCTG

GTpc C. psittaci genotype F amplicon
(SEQ ID NO: 26)
GGGAATGTGGTTGTGCAACTTTAGGAGCTGAATTCCAGTATGCTCAATC

TAATCCTAAAATTGAAATGCTGAATGTAATCTCCAGCCCAACACAATTT

GTAGTTCACAAGCCTAGAGGATACAAGGGAACAGGATCGAACTTTCCTT

TACCTCTAACAGCTGGTACAGATGGTGCTACAGATACTAAATCTGCAAC

ACTCAAATATCATGAATGGCAAGTTGGTTTAGCGCTCTCTTACAGATTG

AACATGCTTGTTCCTTACATTGGCGTAAACTGGTCAAGAGCAACTTTTG

ATGCTG

EXAMPLE 5

Detection of *C. psittaci*, *C. abortus*, and *C. caviae* and Genotyping of *C. psittaci*

This example shows the development and implementation of a novel diagnostic method that is capable of rapidly detecting *C. psittaci*, *C. abortus*, and *C. caviae* in a sample and also rapidly genotyping *C. psittaci*. The methods used in this example are shown schematically in FIG. 6A (identification of *C. psittaci*, *C. abortus*, and *C. caviae*) and FIG. 6B (genotyping *C. psittaci*).

Three novel primer sets (Ppac (SEQ NOs: 3 and 4), GTpc (SEQ NOs: 5 and 6), and GT-F (SEQ NOs: 7 and 8)), with the use of standard cycling conditions followed by HRM, are able to reliably identify and differentiate *C. psittaci* genotypes A through F and detect the closely related *C. abortus* and *C. caviae* species. The Ppac primers (SEQ NOs: 3 and 4) serve as pan markers, able to amplify all *C. psittaci* genotypes as well as *C. caviae* and *C. abortus*, while the GTpc primers (SEQ NOs: 5 and 6) are capable of distinguishing *C. caviae* and all *C. psittaci* genotypes except D/F. The GT-F (SEQ NOs: 7 and 8) primers can be used to specifically amplify genotype F, thus providing a comprehensive algorithm for identifying and genotyping *C. psittaci* in instances where HRM analysis detects a characteristic genotype D/F melt curve. All three primer sets also demonstrate specificity for their respective nucleic targets and sensitivity to at least 200 fg with *C. psittaci* reference strain DNA.

The method was successfully used on clinical specimens and displayed 100% concordance with sequence data generated from both reference isolates and clinical extracts. Numerous avian specimens screened were positive for *C. psittaci*. Genotype A was the most frequently identified genotype, present in 71.4% of the *C. psittaci*-positive specimens that could be typed. Reportedly, genotype A is commonly identified in chlamydia-positive psittacine birds, such as parrots, cockatoos, and cockatiels and the instant findings are therefore consistent with previous reports. Both the B and the E genotypes of *C. psittaci* were rarely present in the clinical samples, accounting for only 7.2% of the specimens. Historically, these genotypes have most commonly been identified in pigeons and doves, again consistent with the results of the instant assay. Notably, *C. psittaci* genotypes C, D, and F were not found in any of the specimens tested, supporting the claim by others that the vast majority of naturally occurring genotypes belong to the A/B/E cluster. *C. caviae* was detected only in guinea pig specimens (Table 3), where it is known to exist. No specimens tested positive for *C. abortus*, an agent typically found in mammals, although a few psittacine infections have been reported. Neither *C. caviae* nor *C. abortus* is considered a classic respiratory pathogen and would not likely be present in respiratory samples being tested for *C. psittaci* in humans. However, if amplification with Ppac primers (SEQ NOs: 3 and 4) yielded a positive amplification curve while amplification of the same sample or source using the GTpc primers (SEQ NOs: 5 and 6) provided a negative result, *C. abortus* should be considered as the potential pathogen and ompA sequencing should be performed for verification. Similarly, amplification with both Ppac primers (SEQ NOs: 3 and 4) and the *C. caviae* specific primer pair (SEQ ID NOs: 16 and 17) indicates the presence of *C. caviae.*

Figure 5B:
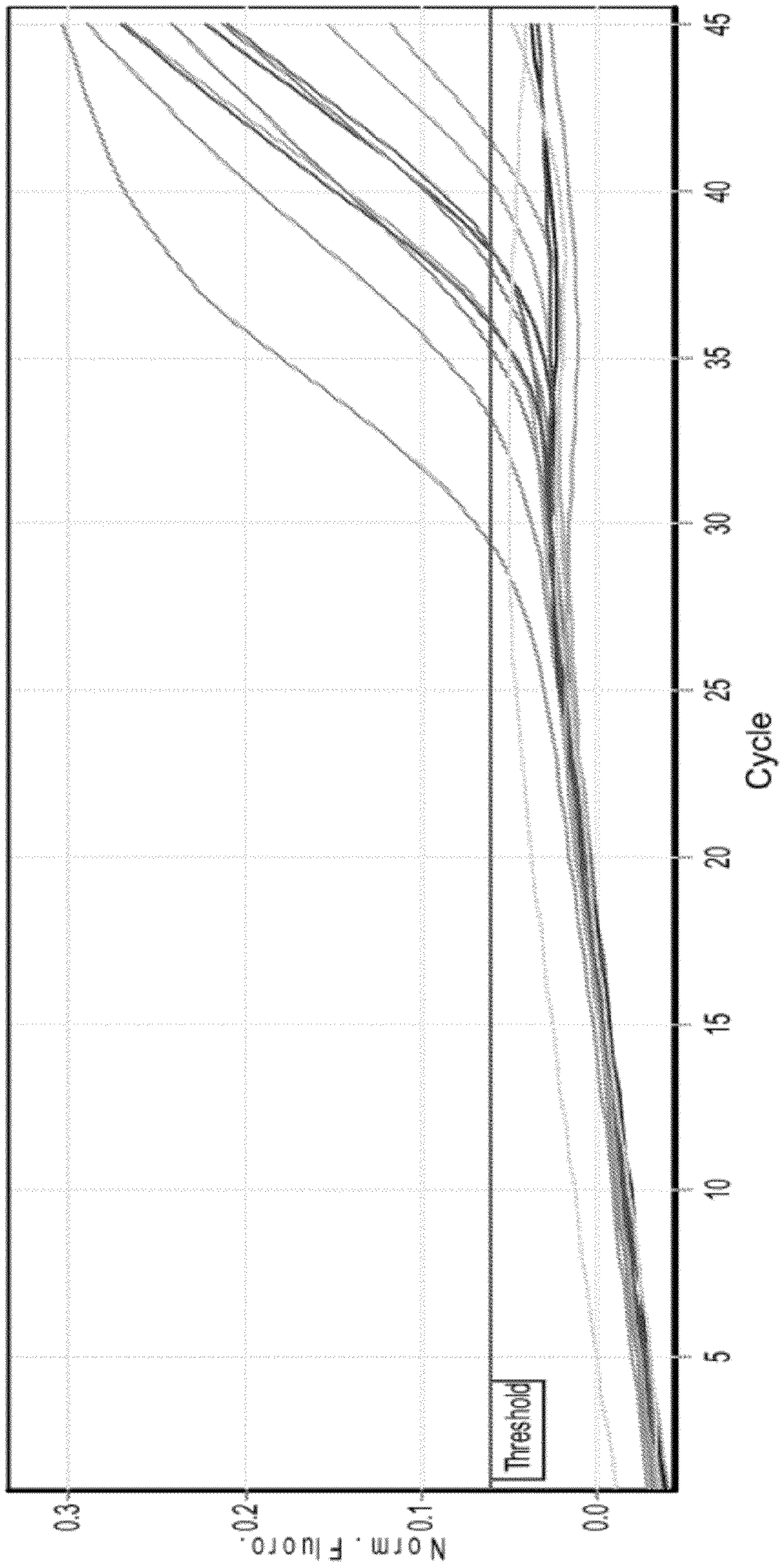

The reliability of HRM analysis is dependent upon both sufficient quantity and sufficient quality of the starting template. As such, specimens with amplification curves that are not sigmoidal or have threshold cycle values of 40 or above should use melt curve data. If possible, these samples should be concentrated and retested for verification. When threshold cycle values of less than 40 are achieved, the HRM data was found to be remarkably consistent, reproducible, and reliable, as evidenced by the substantially identical melt curves generated in each of the triplicate samples assayed on numerous occasions and verified by subsequent sequence analysis. The quality and amount of template nucleic acid are inherent limitations in any real-time PCR assay but are particularly important when HRM analysis is performed. These limitations may account for the 21% of the specimens that were unable to be definitively genotyped using the disclosed methods since some older specimens may not have been properly stored after submission. FIG. 5B is an amplification plot of samples provided by the University of Georgia that tested *C. psittaci* positive on initial examination. In this experiment, the archived samples were subjected to standard real-time PCR conditions and a threshold value determined. As seen in FIG. 5B, the majority of the nucleic acid samples were positive for the amplification of *C. psittaci* nucleic acids. The samples below the threshold are *C. psittaci* negative.

EXAMPLE 6

Amplification of *Chlamydophila* Nucleic Acids with a Specific and a Universal Primer Sequence The above examples describe indirect detection of a *Chlamydophila* species by amplification of *Chlamydophila* nucleic acids using the defined primer disclosed herein. This example describes amplification of *Chlamydophila* nucleic acids using a one defined primer and one universal primer.

To amplify *C. psittaci* nucleic acids with one defined and one universal primer, the nucleic acids in the sample from a subject may be pretreated to add a repeat sequence to the end of the DNA in the sample, for example, using terminal transferase to add a repeat sequence to the 3' end of the DNA in the sample. Then one forward primer comprising for example SEQ ID NO: 3 is used in conjunction with a universal primer that is complementary to the repeat sequence added by terminal transferase tp amplify the nucleic acids in the sample. The detection of amplified nucleic acids indicates the presence of *C. psittaci* in the sample.

EXAMPLE 7

Direct Detection of a *Chlamydophila* Infection

Methods of indirect detection of *Chlamydophila* species in a sample by PCR amplification of *C. psittaci, C. abortus*, and *C. caviae* nucleic acids in a sample are described above. This example illustrates direct detection of *C. psittaci, C. abortus*, and *C. caviae* by hybridization of a labeled primer to a target nucleic acid in a sample.

To directly detect a *C. psittaci* infection in a subject, a nucleic acid sample from a subject containing or suspected of containing *C. psittaci* is contacted with at least one labeled primer comprising the sequence of any one of SEQ ID NOs: 3-8 under very high stringency hybridization conditions. The sample may be contacted by the labeled probe in any hybridization assay known to the art, such as a dot blot assay. Detection of hybridization of the probe to target nucleic acids in the sample will indicate the presence of *C. psittaci* nucleic acids in the sample and positively diagnose an *C. psittaci* infection.

One of skill will recognize that this technique can also be used to identify a *C. caviae* infection (detection of hybridization of probes comprising SEQ ID NOs: 16 or 17), a *C. psittaci* genotype F infection (detection of hybridization of probes comprising SEQ ID NOs: 7 or 8), or a *C. abortus* infection (detection of hybridization of probes comprising SEQ ID NOs: 3 or 4 but not SEQ ID NOs: 5 or 6).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for diagnosing a *Chlamydophila psittaci, Chlamvdophila caviae*, or *Chlamvdophila abortus* infection in a subject suspected of having a *Chlamydophila psittaci, Chlamvdophila caviae*, or *Chlamvdophila abortus* infection, comprising:

obtaining from the subject a sample comprising nucleic acids;

contacting the sample with a first primer pair comprising a forward primer consisting of the nucleic acid sequence set forth as SEQ ID NO: 3 and a label and a reverse primer consisting of the nucleic acid sequence set forth as SEQ ID NO: 4 and a second primer pair comprising a forward primer consisting of the nucleic acid sequence set forth as SEQ ID NO: 5 and a label and a reverse primer consisting of the nucleic acid sequence set forth as SEQ ID NO: 6;

amplifying nucleic acids in the sample using said first and second primer pair to form amplified *Chlamydophila* nucleic acids; and detecting the amplified *Chlamydophila* nucleic acids and identifying the presence or absence of amplified *Chlamydophila psittaci, Chlamydophila caviae*, or *Chlamydophila abortus* nucleic acids in the amplified *Chlamydophila* nucleic acids, thereby diagnosing a *Chlamydophila psittaci, Chlamydophila caviae*, or *Chlamydophila abortus* infection in the subject.

2. The method of claim 1, further comprising amplifying nucleic acids in the sample using a third primer pair comprising a forward primer consisting of the nucleic acid sequence set forth as SEQ ID NO: 7 and a label and a reverse primer consisting of the nucleic acid sequence set forth as SEQ ID NO: 8;

and detecting the presence or absence of amplified nucleic acids, wherein the presence of amplified nucleic acids indicates that the subject is infected with *Chlamydophila psittaci* genotype F, and wherein the absence of amplified nucleic acids indicates that the subject is infected with *Chlamydophila psittaci* genotype D.

3. The method of claim 1, further comprising discriminating between a *Chlamydophila psittaci* infection and a *Chlamydophila caviae* infection by a process comprising:

contacting the sample with a *Chlamydophila caviae*-specific primer that hybridizes under very high stringency conditions to the complement of a *Chlamydophila caviae* nucleic acid sequence set forth as SEQ ID NO: 16 and a *Clamydophila caviae*-specific primer that hybridizes under very high stringency conditions to the complement of a *Chlamydophila caviae* nucleic acid sequence set forth as SEQ ID NO: 17, amplifying *Chlamydophila caviae* nucleic acids in the sample to form amplified *Chlamydophila caviae* nucleic acids; and detecting the amplified *Chlamydophila caviae* nucleic acids, wherein detection of the amplified *Chlamydophila caviae* nucleic acids indicates that the subject is infected with *Chlamydophila caviae.*

4. The method of claim 1, further comprising contacting the sample with a primer pair comprising a forward primer consisting of the nucleic acid sequence set forth as SEQ ID NO: 16 and a label and a reverse primer consisting of the nucleic acid sequence set forth as SEQ ID NO: 17;

amplifying *Chlamydophila caviae* nucleic acids in the sample to form amplified *Chlamydophila caviae* nucleic acids; and detecting the amplified *Chlamydophila caviae* nucleic acids, wherein detection of the amplified *Chlamydophila caviae* nucleic acids indicates that the subject is infected with *Chlamydophila caviae.*

5. The method of claim 1, further comprising discriminating between a *Chlamydophila psittaci* infection and a *Chlamydophila caviae* infection by a process comprising:

performing high resolution melt analysis of the amplified nucleic acids; and detecting the presence of a *Chlamydophila caviae*-specific amplification product with the high resolution melt analysis, wherein the presence of the *Chlamydophila caviae*-specific amplification product is indicative of a *Chlamydophila caviae* infection.

6. The method of claim 1, further comprising distinguishing between *Chlamydophila psittaci* genotypes A, B, C, D/F and E, by a process comprising:

performing high resolution melt analysis of the amplified nucleic acids; and detecting the presence of a *Chlamydophila psittaci* genotype A, B, C, or E-specific amplification product with the high resolution melt analysis, wherein the presence of the *Chlamydophila psittaci* genotype A, B, C, or E-specific amplification product indicates that the subject is infected with *Chlamydophila psittaci* genotype A, B, C, or E, respectively.

7. The method of claim 6, further comprising distinguishing between *Chlamydophila psittaci* genotypes D and F by a process comprising:

contacting the sample with a third primer pair comprising a forward primer consisting of the nucleic acid sequence set forth as SEQ ID NO: 7 and a label and a reverse primer consisting of the nucleic acid sequence set forth as SEQ ID NO: 8;

amplifying *Chlamydophila psittaci* genotype F nucleic acid in the sample to form amplified *Chlamydophila psittaci* genotype F nucleic acids; and detecting the amplified *Chlamydophila psittaci* genotype F nucleic acids, wherein detection of the amplified *Chlamydophila psittaci* genotype F nucleic acids indicates that the subject is infected with *Chlamydophila psittaci* genotype F, and wherein a lack of amplified *Chlamydophila psittaci* genotype F nucleic acids indicates that subject is infected with *Chlamydophila psittaci* genotype D.

8. The method of claim 1, wherein the subject is an avian subject or a mammalian subject.

9. The method of claim 8, wherein the mammalian subject is a human subject.

* * * * *

SEQUENCE LISTING

```
<160> NUMBER OF SEQ ID NOS: 26

<210> SEQ ID NO 1
```

-continued

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
atggtggacc cggtgggctt 20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
acgggggatc cggcgggcct 20

<210> SEQ ID NO 3
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 3
gaaccctatt gtttgccgct acgggttc 28

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
tcctgaagca ccttcccaca 20

<210> SEQ ID NO 5
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 5
gaactcatgt gcaactttag gagctgagtt c 31

<210> SEQ ID NO 6
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 6
gctcttgacc agtttacgcc aata 24

<210> SEQ ID NO 7
<211> LENGTH: 27
<212> TYPE: DNA
<213> ORGANISM: Artificial equence
<220> FEATURE:
<223> OTHER INFORMATION: Synthetic oligonucleotide

<400> SEQUENCE: 7
gacgccattc gtgaaccact cagcgtc 27

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ctcctacagg aagcgcagca 20

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 9
actatgtggg aaggtgct 18

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 10
tagacttcat tttgttgatc tga 23

<210> SEQ ID NO 11
<211> LENGTH: 1660
<212> TYPE: DNA
<213> ORGANISM: Chlamydophila psittaci

<400> SEQUENCE: 11
ttacactctt ctacgagggt aattccaact tattctaagt ggcataagaa ataaaaatgt 60
gtacaaaaat ctgatagctc ttttattagc aagtataagg agttattgct tgaaatctat 120
gcctgaaaac agtctttttt cttatcgtct ttactataat aagaaaagtt tgttatgttt 180
tcgaataatg aactgtatgt tcatgcttaa ggctgttttc acttgcaaga cactcctcaa 240
agccattaat tgcctacagg atatcttgtc tggctttaac ttggacgtgg tgccgccaga 300
agagcaaatt agaatagcga gcacaaaaag aaaagatact aagcataatc tttagaggtg 360
agtatgaaaa aactcttgaa atcggcatta ttgtttgccg ctacgggttc cgctctctcc 420
ttacaagcct tgcctgtagg gaacccagct gaaccaagtt tattaatcga tggcactatg 480
tgggaaggtg cttcaggaga tccttgcgat ccttgcgcta cttggtgtga cgccattagc 540
atccgcgcag gatactacgg agattatgtt ttcgatcgtg tattaaaagt tgatgtgaat 600
aaaactttta gcggcatggc tgcaactcct acgcaggcta caggtaacgc aagtaatact 660
aatcagccag aagcaaatgg cagaccgaac atcgcttacg gaaggcatat gcaagatgca 720
gagtggtttt caaatgcagc cttcctagcc ttaaacattt gggatcgctt cgacattttc 780
tgcaccttag ggcatccaa tggatacttc aaagcaagtt cggctgcatt caacttggtt 840
gggttaatag ggttttcagc tgcaagctca atctctaccg atcttccaat gcaacttcct 900
aacgtaggca ttacccaagg tgttgtggaa ttttatacag acacatcatt ttcttggagc 960

-continued

```
gtaggtgcac gtggagcttt atgggaatgt ggttgtgcaa ctttaggagc tgagttccaa   1020

tacgctcaat ctaatcctaa gattgaaatg ctcaacgtca cttcaagccc agcacaattt   1080

gtgattcaca aaccaagagg ctataaagga gctagctcga attttccttt acctataacg   1140

gctggaacaa cagaagctac agacaccaaa tcagctacaa ttaaatacca tgaatggcaa   1200

gtaggcctcg ccctgtctta cagattgaat atgcttgttc catatattgg cgtaaactgg   1260

tcaagagcaa cttttgatgc tgatactatc cgcattgctc aacctaaatt aaaatcggag   1320

attcttaaca ttactacatg gaacccaagc cttataggat caaccactgc tttgcccaat   1380

aatagtggta aggatgttct atctgatgtc ttgcaaattg cttcgattca gatcaacaaa   1440

atgaagtcta gaaaagcttg tggtgtagct gttggtgcaa cgttaatcga cgctgacaaa   1500

tggtcaatca ctggtgaagc acgcttaatc aatgaaagag ctgctcacat gaatgctcaa   1560

ttcagattct aaggatttag tttatactat cctaactttt taaaccgcta tcagaacctg   1620

ggagtctccg ggttctgatt ttttaaatac cacccttttc                          1660
```

<210> SEQ ID NO 12
<211> LENGTH: 1098
<212> TYPE: DNA
<213> ORGANISM: Chlamydophila psittaci

<400> SEQUENCE: 12

```
atgaaaaaac tcttgaaatc ggcattattg tttgccgcta cgggttccgc tctctcctta     60

caagccttgc ctgtagggaa cccagctgaa ccaagtttat taatcgatgg cactatgtgg    120

gaaggtgctt caggagatcc ttgcgatcct tgcgctactt ggtgtgacgc cattagcatc    180

cgcgcaggat actacggaga ttatgttttc gatcgtgtat taaaagttga tgtgaataaa    240

acttttagcg gcatggctgc aactcctacg caggctacag gtaacgcaag taatactaat    300

cagccagaag caaatggcag accgaacatc gcttacggaa ggcatatgga agatgcagag    360

tggttttcaa atgcagcctt cctagcctta aacatttggg atcgcttcga cattttctgc    420

accttagggg catccaatgg atacttcaaa gcaagttcgg ctgcattcaa cttggttggg    480

ttaatagggt tttcagctgc aagctcaatc tctaccgatc ttccaacgca acttcctaac    540

gtaggcatta cccaaggtgt tgtggaattt tatacagaca catcattttc ttggagcgta    600

ggtgcacgtg gagctttatg ggaatgtggt tgtgcaactt taggagctga gttccaatac    660

gctcaatcta atcctaagat tgaaatgctc aacgtcactt caagcccagc acaatttgtg    720

attcacaaac caagaggcta taaaggagct agctcgaatt ttcctttacc tataacggct    780

ggaacaacag aagctacaga caccaaatca gctacaatta aataccatga atggcaagta    840

ggcctcgccc tgtcttacag attgaatatg cttgttccat atattggcgt aaactggtca    900

agagcaactt ttgatgctga tactatccgc attgctcaac ctaaattaaa atcggagatt    960

cttaacatta ctacatggaa cccaagcctt ataggatcaa ccactgcttt gcccaataat   1020

agtggtaagg atgttctatc tgatgtcttg caaattgctt cgattcagat caacaaaatg   1080

aagtctagaa aagcttgt                                                 1098
```

<210> SEQ ID NO 13
<211> LENGTH: 1065
<212> TYPE: DNA
<213> ORGANISM: Chlamydophila psittaci

<400> SEQUENCE: 13

```
atgaaaaaac tcttgaaatc ggcattattg tttgccgcta cgggttccgc tctctcctta     60
```

-continued

```
caagccttgc ctgtagggaa cccagctgaa ccaagtttat taatcgatgg cactatgtgg    120
gaaggtgctt caggagatcc ttgcgatcct tgcgctactt ggtgtgacgc cattagcatc    180
cgcgcaggat actacggaga ttatgttttc gatcgtgtat taaaagttga tgtgaataaa    240
actatcagcg gtatgggtgc agctcctaca ggaagcgcag cagccgatta caaaactcct    300
acagatagac ccaacatcgc ttatggcaaa cacttgcaag acgctgagtg gttcacgaat    360
gcagctttcc tcgcattaaa tatctgggat cgctttgata ttttctgcac attaggtgct    420
tccaatgggt acttcaaagc tagttctgct gcattcaacc tcgttggttt gattggtgtt    480
aaaggaacct ccgtagcagc tgatcaactt ccaaacgtag gcatcactca aggtattgtt    540
gagttttaca cagatacaac attctcttgg agcgtaggtg cacgtggtgc tttatgggaa    600
tgtggttgtg caactttagg agctgaattc cagtatgctc aatctaatcc taaaattgaa    660
atgctgaatg taatctccag cccaacacaa tttgtagttc acaagcctag aggatacaag    720
ggaacaggat cgaactttcc tttacctcta acagctggta cagatggtgc tacagatact    780
aaatctgcaa cactcaaata tcatgaatgg caagttggtt tagcgctctc ttacagattg    840
aacatgcttg ttccttacat tggcgtaaac tggtcaagag caacttttga tgctgactct    900
atccgcatcg ctcaacctaa attagccgct gctgttttga acttgaccac atggaaccca    960
actcttttag ggaagctac agctttagat gctagcaaca aattctgcga cttcttacaa   1020
atcgcttcga ttcagatcaa caaaatgaag tctagaaaag cttgt                  1065
```

<210> SEQ ID NO 14
<211> LENGTH: 1482
<212> TYPE: DNA
<213> ORGANISM: Chlamydophila caviae

<400> SEQUENCE: 14

```
tttttcttat cgtctttact ataataagaa aagtttgtta tgttttcgat taatgaactg     60
tatgttcatg cttaaggctg ttttcacttg caagacactc ctcaaagcca ttaattgcct    120
acaggatatc ttgtctggct ttaacttgga cgtggtgccg ccagaagagc aatttagaat    180
agcgagcaca aaaagaaaag atactaagca taatctttag aggtgagtat gaaaaaactc    240
ttgaaatcgg cattattgtt tgccactacg ggttccgctc tctccttaca agccttgcct    300
gtagggaatc cagctgaacc aagtttatta attgatggca ctatgtggga aggcgcttca    360
ggcgatcctt gtgatccttg ctctacttgg tgtgatgcta tcagcatccg cgcagggtac    420
tacggagatt atgttttcga tcgcatctta aaagttgatg ttaataaaac tatcagcatg    480
ggacagctc caactggtaa tgcagctgct gactttaaaa ccgttgcaga caggaataac    540
atagcctacg gcaaacatat gcaagatgca gaatggtcca caaacgcggc tttcttagca    600
ttaaacattt gggatcgttt tgatgtcttc tgcacattag ggcatctaa cggctatctc    660
aaagcaaatg ctgcagcttt caatctagtc ggcttacttg ggtaacagg aacagatctt    720
caaggccaat atccaaacgt agccatctct caaggccttg tagagcttta tactgacaca    780
accttctctt ggagcgttgg tgcgcgtgga gctttatggg aatgtggttg cgcaacttta    840
ggagcagagt tccaatatgc gcagtctaat cctaagatcg aaatgcttaa tgtaatttct    900
agcccaacac aatttgtgat tcataagcct agaggatata aagggacagc ggccaacttc    960
cctctgcctt taaccgctgg aacagagagc gctactgata ctaaatcagc tacaattaag   1020
tatcatgaat ggcaaattgg tttagctctt tcttatagat tgaacatgct cgttccatat   1080
```

-continued

```
attggagtaa actggtccag agctacattt gatgctgact ctatccgcat tgctcagcct   1140

aaattaccta cggccatttt aaacctaact acatggaacc ctactttatt aggggaggct   1200

actactataa acactggagc aaattatgct gaccagttac aaattgcttc gcttcaaatc   1260

aacaaaatga agtctagaaa agcttgtggt attgctgttg gtgcaacctt aattgatgct   1320

gacaaatggt cgatcactgg tgaagctcgc ttaatcaacg aaagagctgc tcacgtaaac   1380

gctcaattca gattctaagg atttagttta tactatccta actttttgtc ccgctatcag   1440

aacctaggag cgtctgggtt ctgatttttt atttaaagcc cc                     1482
```

<210> SEQ ID NO 15
<211> LENGTH: 1170
<212> TYPE: DNA
<213> ORGANISM: Chlamydophila abortus

<400> SEQUENCE: 15

```
ttagaatctg aattgagcat tcatgtgagc ggctctttca ttgattaagc gtgcttcacc     60

agtgattgac catttgtcag cgtcgattaa cgttgcacca acagctacac cacaagcttt    120

tctagacttc attttgttga tctgaatcga agcaatttgc aagaagtcag cgaatttgtt    180

gctagtatct aaagctgtag cttctcctaa aagggttggg ttccatgtgg tcaagtttaa    240

cacagcagca gctaatttag gttgagcgat gcggatagcg tcagcatcaa aagttgctcg    300

tgaccagttt acgctaatgt aaggaacaag catgttcaat cgataagaga gcgctaaacc    360

aacttgccat tcgtggtatt taattgtagc cgacttagtg tcagttgcct gatcagtacc    420

agctgttaga ggtaaaggaa atgctgttcc cttgtatcct ctaggcttgt gaaccacaaa    480

ttgtgctggg ctggagacta cattcaacat ttcaatttta ggattagact gagcgtattg    540

gaactctgct cctaaagtcg cacaaccaca ctcccataaa gctccgcgtg cacctacact    600

ccaagagaat gttgtatctg tataaaattc aacgattcct tgagtgatgc ctacattggg    660

aagctgatca gctgctatgg aggatccttt aacaccaatc aaaccaacga ggttgaatgc    720

cgcagaacta gctttgaagt acccattaga agcgcctaat gtgcagaaaa tatcaaagcg    780

atcccagata ttcaatgcga ggaaagctgc attggtgaac cattcggcgt cttgtaagtg    840

tttgccgtaa gcgatgttgg gtctatccgt aggagttttg taattagctg ctgcggttcc    900

tgtaggaact gcacccatgc cggtgatagt tttattcaca tcaactttta atacacgatc    960

gaaaacataa tctccgtagt atcctgcgcg gatgctgata gcatcacacc aagtagagca   1020

aggatcgcaa ggatcacctg aagcaccttc ccacatagtg ccatcgatta ataaacttgg   1080

ttcagctggg ttccctacag gcaaggcttg taaggagaga gcggaacccg tagcggcaaa   1140

caataatgcc gatttcaaga gtttttcat                                     1170
```

<210> SEQ ID NO 16
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 16

```
cacaaagcta agaaagccgc gtttgtg                                         27
```

<210> SEQ ID NO 17
<211> LENGTH: 21
<212> TYPE: DNA
<213> ORGANISM: Artificial sequence

```
<220> FEATURE:
<223> OTHER INFORMATION: Synthetic oligonucleotide

<400> SEQUENCE: 17

ccgttgcaga caggaataac a                                             21


<210> SEQ ID NO 18
<211> LENGTH: 120
<212> TYPE: DNA
<213> ORGANISM: Artificial sequence
<220> FEATURE:
<223> OTHER INFORMATION: Ppac amplicon consensus sequence

<400> SEQUENCE: 18

atcggcatta ttgtttgccg ctacgggttc cgctctctcc ttacaagcct tgcctgtagg     60

gaacccagct gaaccaagtt tattaatcga tggcactatg tgggaaggtg cttcaggaga    120


<210> SEQ ID NO 19
<211> LENGTH: 120
<212> TYPE: DNA
<213> ORGANISM: Artificial sequence
<220> FEATURE:
<223> OTHER INFORMATION: Ppac amplicon of Genotype C

<400> SEQUENCE: 19

atcggcatta ttatttgccg ctacgggttc cgctctctcc ttacaagcct tgcctgtagg     60

gaacccagct gaaccaagtt tattaatcga tggcactatg tgggaaggtg cttcaggaga    120


<210> SEQ ID NO 20
<211> LENGTH: 300
<212> TYPE: DNA
<213> ORGANISM: Artificial sequence
<220> FEATURE:
<223> OTHER INFORMATION: GTpc amplicon consensus sequence
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (64)..(64)
<223> OTHER INFORMATION: n is A or G
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (91)..(91)
<223> OTHER INFORMATION: n is T or C
<220> FEATURE:
<221> NAME/KEY: misc_feature
<222> LOCATION: (94)..(94)
<223> OTHER INFORMATION: n is A or C
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
```

-continued

<221> NAME/KEY: misc_feature
<222> LOCATION: (161)..(161)
<223> OTHER INFORMATION: n is A or G
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (165)..(165)
<223> OTHER INFORMATION: n is A, T, or G
<220> FEATURE:
<221> NAME/KEY: misc_feature
<222> LOCATION: (168)..(170)
<223> OTHER INFORMATION: n is a, c, g, or t
<220> FEATURE:
<221> NAME/KEY: misc_feature
<222> LOCATION: (172)..(173)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (193)..(193)
<223> OTHER INFORMATION: n is A, C, G, or T
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (200)..(200)
<223> OTHER INFORMATION: n is A, C, or T
<220> FEATURE:
<221> NAME/KEY: misc_feature
<222> LOCATION: (200)..(200)
<223> OTHER INFORMATION: n is A, C, or T
<220> FEATURE:
<221> NAME/KEY: misc_feature
<222> LOCATION: (204)..(206)
<223> OTHER INFORMATION: n is A, C, G, or T
<220> FEATURE:
<221> NAME/KEY: misc_feature
<222> LOCATION: (209)..(210)
<223> OTHER INFORMATION: n is A, C, G, or T
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (230)..(230)
<223> OTHER INFORMATION: n is C or T
<220> FEATURE:
<221> NAME/KEY: misc_feature
<222> LOCATION: (233)..(233)
<223> OTHER INFORMATION: n is C or T

```
<220> FEATURE:
<221> NAME/KEY: misc_feature
<222> LOCATION: (240)..(240)
<223> OTHER INFORMATION: n is A or T
<220> FEATURE:
<221> NAME/KEY: misc_feature
<222> LOCATION: (243)..(243)
<223> OTHER INFORMATION: n is A or T
<220> FEATURE:
<221> NAME/KEY: misc_feature
<222> LOCATION: (247)..(247)
<223> OTHER INFORMATION: n is A or C
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (249)..(249)
<223> OTHER INFORMATION: n is T or C
<220> FEATURE:
<221> NAME/KEY: misc_feature
<222> LOCATION: (256)..(256)
<223> OTHER INFORMATION: n is T or C
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (273)..(273)
<223> OTHER INFORMATION: n is T or A
<220> FEATURE:
<221> NAME/KEY: misc_feature
<222> LOCATION: (276)..(276)
<223> OTHER INFORMATION: n is T or C
<220> FEATURE:
<221> NAME/KEY: misc_feature
<222> LOCATION: (279)..(279)
<223> OTHER INFORMATION: n is A or C
<220> FEATURE:
<221> NAME/KEY: misc_feature
<222> LOCATION: (282)..(282)
<223> OTHER INFORMATION: n is A, C, or G
<220> FEATURE:
<221> NAME/KEY: misc_feature
<222> LOCATION: (286)..(286)
<223> OTHER INFORMATION: n is C or G
<220> FEATURE:
<221> NAME/KEY: misc_feature
<222> LOCATION: (312)..(312)
<223> OTHER INFORMATION: n is T or C
<220> FEATURE:
<221> NAME/KEY: misc_feature
<222> LOCATION: (325)..(325)
<223> OTHER INFORMATION: n is A or T
<220> FEATURE:
<221> NAME/KEY: misc_feature
<222> LOCATION: (329)..(329)
<223> OTHER INFORMATION: n is C or T

<400> SEQUENCE: 20

gggaatgtgg ttgtgcaact ttaggagctg agttccaata cgctcaatct aatcctaana      60

ttgaaatgct caangtnact tcaagcccag cacaatttgt gattcacaaa ccaagaggct     120

ataaagganc tngctcgaat tttcctttac ctataacngc tggnacannn gnngctacag     180

anacnaaatc ngcnacantn aaatancatg aatggcaagt nggnctngcn ctntcttaca     240

gattgaanat gcttgttccn tanattggcg taaactggtc aagagcaact tttgatgctg     300

<210> SEQ ID NO 21
```

-continued

<211> LENGTH: 300
<212> TYPE: DNA
<213> ORGANISM: Artificial sequence
<220> FEATURE:
<223> OTHER INFORMATION: GTpc amplicon of Genotype A

<400> SEQUENCE: 21
gggaatgtgg ttgtgcaact ttaggagctg agttccaata cgctcaatct aatcctaaga 60
ttgaaatgct caacgtcact tcaagcccag cacaatttgt gattcacaaa ccaagaggct 120
ataaaggagc tagctcgaat tttcctttac ctataacggc tggaacaaca gaagctacag 180
acaccaaatc agctacaatt aaataccatg aatggcaagt aggcctcgcc ctgtcttaca 240
gattgaatat gcttgttcca tatattggcg taaactggtc aagagcaact tttgatgctg 300

<210> SEQ ID NO 22
<211> LENGTH: 300
<212> TYPE: DNA
<213> ORGANISM: Artificial sequence
<220> FEATURE:
<223> OTHER INFORMATION: GTpc amplicon of Genotype B

<400> SEQUENCE: 22
gggaatgtgg ttgtgcaact ttaggagctg agttccaata cgctcaatct aatcctaaga 60
ttgaaatact caacgtcact tcaagcccag cacaatttgt gattcacaaa ccaagaggct 120
ataaaggagc tagctcgaat tttcctttac ctataacggc tggaacaaca gaagctacag 180
acaccaaatc agctacaatt aaataccatg aatggcaagt aggcctcgcc ctgtcttaca 240
gattgaatat gcttgttcca tatattggcg taaactggtc aagagcaact tttgatgctg 300

<210> SEQ ID NO 23
<211> LENGTH: 300
<212> TYPE: DNA
<213> ORGANISM: Artificial sequence
<220> FEATURE:
<223> OTHER INFORMATION: GTpc amplicon of Genotype C

<400> SEQUENCE: 23
gggaatgtgg ttgcgcaact ttaggagctg aattccaata cgctcaatct aatcctaaaa 60
ttgaaatgtt gaatgtaatc tccagcccag cacaatttgt ggttcacaag cctagaggat 120
acaagggaac gtccgccaac tttcctttac ctgcaaatgc aggcacagag gctgctacgg 180
atactaaatc tgcaacactc aaatatcatg aatggcaagt tggtctagca ctctcttaca 240
gattgaacat gttagttcct tacattggcg taaactggtc acgagcaact tttgatgccg 300

<210> SEQ ID NO 24
<211> LENGTH: 300
<212> TYPE: DNA
<213> ORGANISM: Artificial sequence
<220> FEATURE:
<223> OTHER INFORMATION: GTpc amplicon of Genotype D

<400> SEQUENCE: 24
gggaatgtgg ttgtgcgact ttaggagccg agttccaata cgctcaatct aatcctaaaa 60
ttgaaatgct caatgtaact tcaagcccag cacaatttgt gattcacaaa ccaagaggct 120
ataaaggaac tggctcgaat tttcctttac ctatagacgc gggtacagag gctgctacag 180
atactaagtc tgcaacactc aaatatcatg aatggcaagt tggtctagca ctctcttaca 240
gattgaacat gcttgttcct tacattggcg taaactggtc aagagcaact tttgatgctg 300

-continued

```
<210> SEQ ID NO 25
<211> LENGTH: 300
<212> TYPE: DNA
<213> ORGANISM: Artificial sequence
<220> FEATURE:
<223> OTHER INFORMATION: GTpc amplicon of Genotype E

<400> SEQUENCE: 25

gggaatgtgg ttgtgcaact ttaggagctg agttccaata cgctcaatct aatcctaaga      60

ttgaagtgct caacgtcact tcaagcccag cacaatttgt gattcacaaa ccaagaggct     120

ataaaggagc tagctcgaat tttcctttac ctataacggc tggaacaaca gaagctacag     180

acaccaaatc agctacaatt aaataccatg aatggcaagt aggcctcgcc ctgtcttaca     240

gattgaatat gcttgttcca tatattggcg taaactggtc aagagcaact tttgatgctg     300


<210> SEQ ID NO 26
<211> LENGTH: 300
<212> TYPE: DNA
<213> ORGANISM: Artificial sequence
<220> FEATURE:
<223> OTHER INFORMATION: GTpc amplicon of Genotype F

<400> SEQUENCE: 26

gggaatgtgg ttgtgcaact ttaggagctg aattccagta tgctcaatct aatcctaaaa      60

ttgaaatgct gaatgtaatc tccagcccaa cacaatttgt agttcacaag cctagaggat     120

acaagggaac aggatcgaac tttcctttac ctctaacagc tggtacagat ggtgctacag     180

atactaaatc tgcaacactc aaatatcatg aatggcaagt tggtttagcg ctctcttaca     240

gattgaacat gcttgttcct tacattggcg taaactggtc aagagcaact tttgatgctg     300
```